United States Patent
Barrett et al.

(10) Patent No.: US 11,278,498 B2
(45) Date of Patent: Mar. 22, 2022

(54) SUSTAINED RELEASE SOLID DOSAGE FORMS FOR MODULATING THE COLONIC MICROBIOME

(71) Applicant: Axial Therapeutics, Inc., Waltham, MA (US)

(72) Inventors: Ryan Barrett, Acton, MA (US); Hitesh Bhagat, Framingham, MA (US); Anthony Stewart Campbell, Framingham, MA (US)

(73) Assignee: Axial Therapeutics, Inc., Waltham, MA (US)

(*) Notice: Subject to any disclaimer, the term of this patent is extended or adjusted under 35 U.S.C. 154(b) by 0 days.

(21) Appl. No.: 17/089,956

(22) Filed: Nov. 5, 2020

(65) Prior Publication Data

US 2021/0052503 A1 Feb. 25, 2021

Related U.S. Application Data

(63) Continuation of application No. PCT/US2020/031718, filed on May 6, 2020.

(60) Provisional application No. 62/844,016, filed on May 6, 2019, provisional application No. 62/844,013, filed on May 6, 2019, provisional application No. 62/844,006, filed on May 6, 2019.

(51) Int. Cl.
| | |
|---|---|
| *A61K 9/20* | (2006.01) |
| *A61K 9/28* | (2006.01) |
| *A61K 9/48* | (2006.01) |
| *A61K 9/50* | (2006.01) |
| *A61K 31/353* | (2006.01) |

(52) U.S. Cl.
CPC .......... *A61K 9/2013* (2013.01); *A61K 9/2009* (2013.01); *A61K 9/2018* (2013.01); *A61K 9/2027* (2013.01); *A61K 9/2054* (2013.01); *A61K 9/2813* (2013.01); *A61K 9/2826* (2013.01); *A61K 9/2846* (2013.01); *A61K 9/2866* (2013.01); *A61K 9/485* (2013.01); *A61K 9/4858* (2013.01); *A61K 9/4866* (2013.01); *A61K 9/501* (2013.01); *A61K 9/5015* (2013.01); *A61K 9/5026* (2013.01); *A61K 9/5042* (2013.01); *A61K 31/353* (2013.01)

(58) Field of Classification Search
CPC .. A61K 9/2013; A61K 9/2009; A61K 9/2018; A61K 9/2027; A61K 9/2054; A61K 9/2813; A61K 9/2826; A61K 9/2846; A61K 9/2866; A61K 9/485; A61K 9/4858; A61K 9/4866; A61K 9/501; A61K 9/5015; A61K 9/5026; A61K 9/5042; A61K 31/353

See application file for complete search history.

(56) References Cited

U.S. PATENT DOCUMENTS

| | | | | |
|---|---|---|---|---|
| 5,120,548 | A * | 6/1992 | McClelland | A61K 9/2866 424/424 |
| 5,354,556 | A * | 10/1994 | Sparks | A61P 11/08 424/419 |
| 5,639,476 | A * | 6/1997 | Oshiack | A61K 9/5078 424/468 |
| 5,674,533 | A * | 10/1997 | Santus | A61P 11/14 424/493 |
| 8,642,087 | B1 * | 2/2014 | Dziubla | C08F 220/06 424/487 |
| 2002/0176898 | A1 * | 11/2002 | Morre | A61K 31/353 424/729 |
| 2003/0105030 | A1 | 6/2003 | Liao et al. | |
| 2003/0215509 | A1 * | 11/2003 | Rao | A61K 31/19 424/468 |
| 2004/0221868 | A1 * | 11/2004 | Chang | A61K 9/2866 132/321 |
| 2006/0068021 | A1 * | 3/2006 | Kuhrts | A61K 9/1694 424/490 |
| 2007/0292506 | A1 | 12/2007 | Goldenberg et al. | |
| 2013/0129809 | A1 * | 5/2013 | Srivastava | A61K 31/352 424/450 |
| 2014/0099281 | A1 | 4/2014 | Zasloff | |
| 2017/0190657 | A1 | 7/2017 | Gallop et al. | |
| 2018/0015074 | A1 * | 1/2018 | Kellogg | A61K 9/0014 |

OTHER PUBLICATIONS

International Search Report and Written Opinion for Application No. PCT/US2020/031718 dated Jul. 29, 2020.

* cited by examiner

*Primary Examiner* — Robert A Wax
*Assistant Examiner* — Olga V. Tcherkasskaya
(74) *Attorney, Agent, or Firm* — Wolf, Greenfield & Sacks, P.C.

(57) ABSTRACT

Described are sustained-release solid dosage forms of epigallocatechin gallate (EGCG) or aminosterol compositions. In one aspect of the invention the sustained-release solid dosage forms of EGCG or an aminosterol are capsules comprising a plurality of coated solid particulates. Another aspect of the invention relates to methods of inhibiting, ameliorating, reducing the likelihood of, delaying the onset of, treating or preventing an amyloid disorder, comprising the step of administering to a subject in need a therapeutically effective amount of the solid dosage form. In certain aspects, the amyloid disorder is Parkinson's Disease.

16 Claims, 34 Drawing Sheets

SUSTAINED RELEASE SOLID DOSAGE FORMS FOR MODULATING THE COLONIC MICROBIOME

RELATED APPLICATIONS

This application is a continuation-in-part of, and claims priority under 35 U.S.C. § 120 to, PCT Application Number PCT/US2020/031718, filed May 6, 2020, which claims priority under 35 U.S.C. § 119(e) to U.S. Provisional Application No. 62/844,006, filed May 6, 2019; U.S. Provisional Application No. 62/844,013, filed May 6, 2019; and U.S. Provisional Application No. 62/844,016, filed May 6, 2019. The entire contents of each of these applications are incorporated herein by reference.

FIELD

The present disclosure relates to sustained release solid dosage forms of compositions comprising a polyphenol or an aminosterol, and related compositions and methods. Such dosage forms are useful, for example, in the treatment or prevention of neurological disorders by way of the gut-brain axis.

BACKGROUND

Many neurodegenerative diseases are associated with atypical aggregation of proteins in the brain, which lead to cell death and a resulting manifestation of many neuropathies. It is believed that disease specificity is a consequence of (i) the specific proteins involved in aggregation, (ii) the specific regions of the brain affected, and (iii) the specific neuronal cell types affected. In the case of the natural human protein α-synuclein, aberrant aggregation of this protein leads to any of over 50 "α-synucleinopathies," of which Parkinson's Disease is the most common and most widely studied. In Parkinson's Disease, α-synuclein aggregation leads to the accumulation of large precipitated aggregates called Lewy bodies, within certain neuronal cell types, most typically those that produce the neurotransmitter dopamine. When enough α-synuclein aggregate is present, neuronal death occurs and dopamine production declines. Dopamine is required for proper control of movement, and once dopaminergic neurons die off, they are not replaced. Over time, the dopamine pool declines irreversibly to a point where motor symptoms progress, eventually becoming debilitating to an afflicted subject.

There is growing evidence of the critical role that the gut-brain axis plays in α-synucleinopathies and amyloid disorders, such as Parkinson's Disease. (see, e.g., International Publication Number WO 2018/213204, incorporated herein by reference)

There are currently no curative therapies for amyloid disorders, or α-synucleinopathies, such as Parkinson's Disease, and as such there exists a substantial unmet therapeutic need, especially for modalities that utilize the gut-brain axis to deliver therapeutic relief and benefits to subjects in need thereof.

Epigallocatechin gallate (EGCG) is a polyphenolic catechin compound found in abundance in the dried leaves of green tea. PCT application PCT/US2018/032605 (International Publication Number WO 2018/213204) discloses methods and compositions for the prevention, amelioration or alleviation of neurological disorders associated with microbially-induced amyloid formation, demonstrating that EGCG is not only a potent inhibitor of α-synuclein aggregation, but is also an inhibitor of aggregation of both the bacterially-derived extracellular subunit protein CsgA, and aggregation of α-synuclein which has been seeded by bacterial CsgA protein.

Additionally, EGCG further aids in correcting gut dysbiosis, preventing obesity, improving intestinal barrier function, and limiting endotoxin translocation, and adipose inflammation (Journal of Nutritional Biochemistry, 2019, 67, pp 78-89), as well as improving regularity (Environmental Health and Preventive Medicine, May 2003, 8, pp 47-51).

EGCG and other polyphenolic compounds have demonstrated reduction in Alzheimer-like pathologies in mice (Journal of Biological Chemistry, 2018, 294, pp 2714-2731). Further reports suggest gut amyloid-producing bacteria may play a role in diabetes (Abstract for the $5^{th}$ Annual Translational Microbiome Conference, Apr. 16-18, 2019, Boston, Mass.). Traditionally, EGCG is formulated for systemic administration (see, e.g., Food Res Int. 2012 Nov.; 49(1): 112-116; J. Agric. Food Chem. 2007, 55, 8941-8949; Food Chemistry 73 (2001) 481-486; and Biotechnol. J. 2010, 5, 1050-1059) due to its tendency to be metabolized by intestinal bacteria (see, e.g., Chem. Pharm. Bull. 1997, 45(5) 888-93).

Therefore, a critical, unmet need exists for delivering, in a sustained-release or controlled-release manner, compositions comprising a polyphenol or an aminosterol to the colon, which is the site of microbiota-derived protein aggregates and/or their precursor, monomeric forms. Furthermore, there exists a need for sustained-release, solid dosage forms of compositions comprising a polyphenol or an aminosterol with high levels of compound loading, that can be manufactured with accuracy and precision, for delivery and distribution to and throughout the colon.

SUMMARY

In one aspect, described herein is a sustained-release solid dosage form, comprising a plurality of solid particulates selected from mini-tablets, beads, granules, and pellets, or an individual solid dosage form, wherein the solid particulates or individual solid dosage form each comprise:
a core, comprising an active agent, and optionally one or more release rate controlling material, wherein the release rate controlling material is selected from the group consisting of poly(methyl methacrylate), methacrylic acid-ethyl acrylate copolymer, ethyl cellulose, poly(vinyl acetate), polycarbophil, hydroxypropyl cellulose, hydroxypropyl methyl cellulose, poly(urethane), poly(siloxane), poly(vinyl alcohol), poly(ethylene), poly(vinyl pyrrolidone), poly(2-hydroxyethyl methacrylate), poly(acrylic acid), polyacrylamide, poly(ethylene-co-vinyl acetate), and poly(ethylene glycol), or a combination thereof; and optionally, a coating surrounding the core, comprising a release rate controlling material selected from the group consisting of poly(methyl methacrylate), methacrylic acid-ethyl acrylate copolymer, ethyl cellulose, poly(vinyl acetate), poly(urethane), poly(siloxane), poly(ethylene), poly(2-hydroxyethyl methacrylate), poly(acrylic acid), polyacrylamide, and poly(ethylene-co-vinyl acetate), or a combination thereof;
provided that the sustained-release dosage form comprises at least one release rate controlling material; and
wherein the active agent comprises a polyphenol or an aminosterol. In a particular embodiment, the active agent is EGCG. In a particular embodiment, the active agent is an aminosterol.

In certain embodiments, the core further comprises one or more of a diluent, a binder, a lubricant, a glidant, a plasticizer, and an insoluble or slow-dissolving polymer.

In certain embodiments, the core further comprises means for osmotic pressure controlled release of the active agent. See, e.g., "Osmotic Drug Delivery System as a Part of Modified Release Dosage Form," Keraliya et al., ISRN Pharmaceutics, Volume 2012, Article ID 528079, 9 pages.

In certain embodiments, the core comprises a matrix.

In certain embodiments, the sustained release solid dosage form is a capsule, e.g., containing a plurality of solid particulates as described herein.

In certain embodiments, the diameter of each solid particulate is about 0.1 mm to about 5 mm. In certain embodiments, the diameter of each solid particulate is about 0.3 mm to about 2 mm. In certain embodiments, the diameter of each solid particulate is about 1 mm to about 5 mm. In certain embodiments, the diameter of each solid particulate is about 1 mm. In certain embodiments, the diameter of each solid particulate is about 4 mm.

In certain embodiments, the sustained release solid dosage form comprises a coating surround the core. In certain embodiments, the weight ratio of the core to the coating is about 99:1 to about 41:9. In certain embodiments, the weight ratio is about 99:1, about 80:1, about 60:1, about 40:1, about 20:1, about 10:1, or about 5:1.

In certain embodiments, the release rate controlling material of the coating is selected from the group consisting of hydroxypropyl cellulose, hydroxypropyl methyl cellulose, polycarbophil, poly(ethylene glycol), poly(vinyl alcohol), and poly(ethylene oxide), and the release rate controlling material has a viscosity of about 3 cP to about 1,000,000 cP.

In certain embodiments, the weight percentage of the active agent in each core is about 5% to about 95%. In certain embodiments, the weight percentage of the active agent in each core is about 25% to about 75%. In certain embodiments, the weight percentage of the active agent in each core is about 40% to about 60%.

In certain embodiments, the sustained-release solid dosage form is a capsule comprising the plurality of solid particulates, wherein each solid particulate comprises an immediate release particulate and the capsule is coated with a sustained release material. In certain embodiments, the solid particulate comprises a sustained release matrix further coated by a membrane.

In certain embodiments, each core comprises one or more excipients selected from the group consisting of lactose, microcrystalline cellulose, and mannitol.

In certain embodiments, the sustained release solid dosage form comprises about 2 to about 12,000 solid particulates. In certain embodiments, the sustained release solid dosage form contains 12,000-60,000 solid particulates.

In certain embodiments, the sustained release solid dosage form comprises solid particulates that have uniform properties. In certain embodiments, the sustained release solid dosage form comprises solid particulates that have different properties. Such properties include solid particulate type, size, percentage of active agent, dose of active agent, and release profile (i.e., rate of release of active agent). In certain particular embodiments, the sustained release solid dosage form comprises solid particulates having uniform release profiles. In other particular embodiments, the sustained release solid dosage form comprises solid particulates having different release profiles.

In certain embodiments, the sustained release solid dosage form comprises a total amount of active agent in the range of about 1 mg to about 1,000 mg. In certain embodiments, the total amount of active agent is in the range of 5-100 mg, 50-100 mg, 50-200 mg, 100-300 mg, 200-400 mg, 300-500 mg, 400-600 mg, 500-700 mg, 600-800 mg, 700-900 mg, or 800-1,000 mg.

In a particular embodiment of the sustained-release solid dosage form each solid particulate or individual solid dosage form comprises:

(a) the core, comprising the active agent in about 20-50% by weight of the core; mannitol in about 24-49% by weight of the core; microcrystalline cellulose in about 24-40% by weight of the core; a lubricant and a binder together in about 0.25-5% by weight of the core; and (b) the coating surrounding the core, comprising the release rate controlling material selected from the group consisting of poly(methyl methacrylate), ethyl cellulose, poly(vinyl acetate), poly(urethane), poly(siloxane), poly(ethylene), poly(2-hydroxyethyl methacrylate), poly(acrylic acid), polyacrylamide and poly(ethylene-co-vinyl acetate), or a combination thereof; wherein the weight ratio of the coating in each solid particulate or individual solid dosage form is from about 1% to about 80% of the weight of the uncoated core.

In certain embodiments, the sustained-release solid dosage forms described herein are produced by hot melt extrusion. For example, the solid particulates of the sustained-release solid dosage forms may be produced by hot melt extrusion. See, e.g., Pharmaceutics 2019, 11(5), 218.

In certain embodiments, the invention relates to a sustained-release solid dosage form, comprising a plurality of solid particulates, wherein each solid particulate comprises:
(a) a core, comprising an active agent; and
(b) a coating, comprising ethyl cellulose and a release rate controlling polymer selected from the group consisting of hydroxypropyl cellulose and hydroxypropyl methylcellulose (HPMC);
wherein the coating surrounds the core. In certain embodiments, the active agent is a polyphenol or an aminosterol. In a particular embodiment, the active agent is EGCG. In a particular embodiment, the active agent is an aminosterol.

In certain embodiments, the subject is human.

In certain embodiments, the subject suffers from Parkinson's Disease.

In certain embodiments, the subject suffers from gastrointestinal symptoms comprising one or more of dysphagia, reduced gut motility, gastroparesis, constipation (including chronic constipation and chronic idiopathic constipation), small intestinal bacterial overgrowth (SIBO), diarrhea, abdominal pain, cramping, bloating, flatulence, and nausea. In certain embodiments, the gastrointestinal symptoms are associated with Parkinson's Disease or Parkinsonism.

In another aspect, provided herein is a sustained-release solid dosage form, comprising a plurality of solid particulates selected from mini-tablets, beads, granules, and pellets, or an individual solid dosage form, wherein the solid particulates or individual solid dosage form each comprise:

(a) a core, comprising epigallocatechin gallate (EGCG), and optionally one or more release rate controlling material; and (b) optionally, a coating surrounding the core comprising a release rate controlling material;

provided that the sustained-release dosage form comprises at least one release rate controlling material;

wherein the release rate controlling material is selected from the group consisting of ethyl cellulose, poly(ethylene-oxide) (PEO), poly(acrylic acid), methacrylic acid copolymer, methacrylic ester copolymer, and alkylammonium methacrylate copolymer.

In certain embodiments, the core comprises: (a) EGCG, (b) microcrystalline cellulose, (c) mannitol, (d) sodium stearyl fumarate, and (e) colloidal silicon dioxide. See, e.g., Example 13. In certain particular embodiments, the weight percent of (a) in the core is about 50%, the weight percent of (b) in the core is about 23.8%, the weight percent of (c) in the core is about 23.9%, the weight percent of (d) in the core is about 2%, and the weight percent of (e) in the core is about 0.3%. In certain embodiments, the dosage form comprises a coating, wherein the coating comprises (f) methacrylic ester copolymer, alkylammonium methacrylate copolymer, or a combination thereof, (g) HPMC E-5, (h) Tween 80, and (i) talc. In certain particular embodiments, (f) is EUDRAGUARD® control. In certain particular embodiments, (f) is Eudragit® NE 30 D. In certain embodiments, the weight percent of (f) in the coating is about 45.5%, the weight percent of (g) in the coating is about 4.5%, the weight percent of (h) in the coating is about 4.5%, and the weight percent of (i) in the coating is about 45.5%. In certain embodiments, the weight ratio of the coating to the core is in the range of about 8:100 to about 9.5:100.

In certain embodiments, the core comprises: (a) EGCG, (b) poly(acrylic acid), (c) colloidal silicon dioxide, and (d) magnesium stearate. See, e.g., Formulation B2. In certain particular embodiments, (b) is Carbopol 971P. In certain particular embodiments, the weight percent of (a) in the core is about 58.6%, the weight ratio of (b) in the core is about 39%, the weight ratio of (c) in the core is about 1.2%, and the weight ratio of (d) in the core is about 1.2%. In certain particular embodiments, the dosage form is compressed to a hardness of between 10 kg and 15 kg. In certain particular embodiments, the dosage form does not comprise a coating with a release rate controlling material.

In certain embodiments, the core comprises: (a) EGCG, (b) poly(ethyleneoxide), (c) colloidal silicon dioxide, and (d) sodium stearyl fumarate. See, e.g., Formulation B6. In certain particular embodiments, (b) is PEO 600K. In certain particular embodiments, the weight percent of (a) in the core is about 19.3%, the weight ratio of (b) in the core is about 77.2%, the weight ratio of (c) in the core is about 1.2%, and the weight ratio of (d) in the core is about 2.3%. In certain particular embodiments, the dosage form is compressed to a hardness of between 10 kg and 15 kg. In certain particular embodiments, the dosage form does not comprise a coating with a release rate controlling material.

In certain embodiments, the core comprises: (a) EGCG, (b) poly(acrylic acid), (c) talc, and (d) magnesium stearate. See, e.g., Formulation B8. In certain particular embodiments, (b) is Carbopol 971P. In certain particular embodiments, the weight percent of (a) in the core is about 65.3%, the weight ratio of (b) in the core is about 32.7%, the weight ratio of (c) in the core is about 1%, and the weight ratio of (d) in the core is about 1%. In certain particular embodiments, the dosage form is compressed to a hardness of between 10 kg and 15 kg. In certain particular embodiments, the dosage form does not comprise a coating with a release rate controlling material.

In certain embodiments, the core comprises: (a) EGCG, (b) methacrylic ester copolymer, alkylammonium methacrylate copolymer, or a combination thereof, (c) colloidal silicon dioxide, and (d) magnesium stearate. See, e.g., Formulation WI2. In certain particular embodiments, (b) is Eudragit RL PO. In certain particular embodiments, the weight percent of (a) in the core is about 32.7%, the weight ratio of (b) in the core is about 65.3%, the weight ratio of (c) in the core is about 1%, and the weight ratio of (d) in the core is about 1%. In certain particular embodiments, the dosage form is compressed to a hardness of between 10 kg and 15 kg. In certain particular embodiments, the dosage form does not comprise a coating with a release rate controlling material. In certain particular embodiments, the dosage form does comprise a coating with a release rate controlling material, wherein the coating comprises methacrylic ester copolymer, alkylammonium methacrylate copolymer, or a combination thereof. In certain particular embodiments, the coating comprises Eudragit RL PO. In certain particular embodiments, the weight ratio of the coating to the core is about 8:100 to about 10:100.

In certain embodiments, the core comprises: (a) EGCG, (b) methacrylic ester copolymer, alkylammonium methacrylate copolymer, or a combination thereof, (c) colloidal silicon dioxide, and (d) sodium stearyl fumarate. See, e.g., Formulation WI3. In certain particular embodiments, (b) is Eudragit RS PO. In certain particular embodiments, the weight percent of (a) in the core is about 32%, the weight ratio of (b) in the core is about 64.1%, the weight ratio of (c) in the core is about 1.3%, and the weight ratio of (d) in the core is about 2.6%. In certain particular embodiments, the dosage form is compressed to a hardness of between 10 kg and 15 kg. In certain particular embodiments, the dosage form does not comprise a coating with a release rate controlling material.

In certain embodiments, the core comprises: (a) EGCG, (b) ethyl cellulose, and (c) dibutyl sebacate. See, e.g., Formulation HME-4. In certain particular embodiments, the weight percent of (a) in the core is about 40%, the weight percent of (b) in the core is about 40%, and the weight percent of (c) in the core is about 20%. In certain particular embodiments, the core further comprises: (d) HPMC CR, and (e) propylene glycol. See, e.g., Formulation HME-5. In certain particular embodiments, the weight percent of (a) in the core is about 35%, the weight percent of (b) in the core is about 20%, the weight percent of (c) in the core is about 10%, the weight percent of (d) in the core is about 15%, and the weight percent of (e) in the core is about 20%.

In certain embodiments, the sustained-release solid dosage form is formulated to release 5-25% of the EGCG during the first 4 hours, and to release no more than 75-85% of the EGCG during the first 40 hours, after administration of the dosage form to a human subject. In certain embodiments, the sustained-release solid dosage form is formulated to release at least 25-50% of the EGCG during the first 40 hours after administration of the dosage form to the human subject.

In certain embodiments, the sustained-release solid dosage form is formulated to release 10-50% of the EGCG within 24 hours of administration of the dosage form to a human subject. In certain embodiments, the sustained-release solid dosage form is formulated to release 30-80% of the EGCG within 48 hours of administration of the dosage form to a human subject. In certain embodiments, the sustained-release solid dosage form is formulated to release at least 60% of the EGCG within 72 hours of administration of the dosage form to a human subject. In certain embodiments, the sustained-release solid dosage form is formulated to release at least 75% of the EGCG within 72 hours of administration of the dosage form to a human subject. In certain embodiments, the sustained-release solid dosage form is formulated to release 10-50% of the EGCG within 24 hours, 30-80% of the EGCG within 48 hours, and at least 60% of the EGCG within 72 hours of administration of the dosage form to a human subject.

In another aspect, provided herein is a method of inhibiting, ameliorating, reducing the likelihood of, delaying the onset of, treating, or preventing an amyloid disorder, the method comprising administering to a subject in need thereof a therapeutically effective amount of one or more sustained-release solid dosage form as described herein.

In certain embodiments, the amyloid disorder is selected from the group consisting of α-synucleinopathy, Parkinson's Disease, Lewy Body Dementia, incidental Lewy body disease, Lewy body variant of Alzheimer's disease, multiple system atrophy, or pure autonomic failure, or any combination thereof.

In certain embodiments, the amyloid disorder is intestinal dysbiosis, intestinal hyperpermeability, irritable bowel syndrome (IBS), inflammatory bowel disease (IBD), ulcerative colitis and Crohn's disease.

In certain embodiments, the total daily dose of active agent is in the range of about 1 mg to about 1,000 mg. In certain embodiments, the methods described herein further comprise the step of co-administering to the subject a therapeutically effective amount of an additional therapeutic agent. Such additional therapeutic agents may be selected from caffeine, nicotine, theophylline, theobromine, xanthine, methylxanthine, or derivatives thereof; an inhibitor of α-synuclein aggregation; L-DOPA, carbidopa, Lodosyn, levodopa, Droxidopa, Northera, Rasagiline, apomorphine hydrochloride, Bromocriptine, Rotigotine, Pramipexole, Ropinirole, Benzotropine, Trihexyphenidyl, Selegiline, Entacapone, Tolcapone, Amantadine, Pimavanersin, Rivastigmine; or any combination thereof.

In certain embodiments, said inhibiting, ameliorating, reducing the likelihood of, delaying the onset of, treating, or preventing an amyloid disorder comprises inhibiting CsgA aggregation in the subject.

In certain embodiments, wherein said inhibiting, ameliorating, reducing the likelihood of, delaying the onset of, treating, or preventing an amyloid disorder comprises inhibiting curli formation.

In another aspect, provided herein is a method of modulating colonic microbiota and/or their metabolites, the method comprising administering to a subject in need thereof a therapeutically effective amount of the sustained-release solid dosage form as described herein.

In certain embodiments, the invention relates to a method of treating an amyloid disorder, comprising the step of orally administering to a mammal in need thereof a therapeutically effective amount of any one of the aforementioned solid dosage forms.

In certain embodiments, the invention relates to a method of inducing remission of an amyloid disorder, comprising the step of orally administering to a mammal in need thereof a therapeutically effective amount of any one of the aforementioned solid dosage forms.

In certain embodiments, the invention relates to a method of maintaining remission of an amyloid disorder, comprising the step of orally administering to a mammal in need thereof a therapeutically effective amount of any one of the aforementioned solid dosage forms.

In certain embodiments, the invention relates to a method of inhibiting, ameliorating, reducing the likelihood, delaying the onset of, treating, or preventing an amyloid disorder, the method comprising administering to a subject in need thereof a therapeutically effective amount of a solid dosage form of one or more of the compositions shown and described herein.

In certain embodiments, the invention relates to a method for modulating colonic microbiota and/or their metabolites, the method comprising administering to a subject in need thereof a therapeutically effective amount of a solid dosage form of one or more of the compositions as shown and described herein.

In certain embodiments, the invention relates to any one of the aforementioned methods, wherein the amyloid disorder is an α-synucleinopathy.

In certain embodiments, the invention relates to any one of the aforementioned methods, wherein the amyloid disorder is Parkinson's Disease.

DETAILED DESCRIPTION

Figure 1:
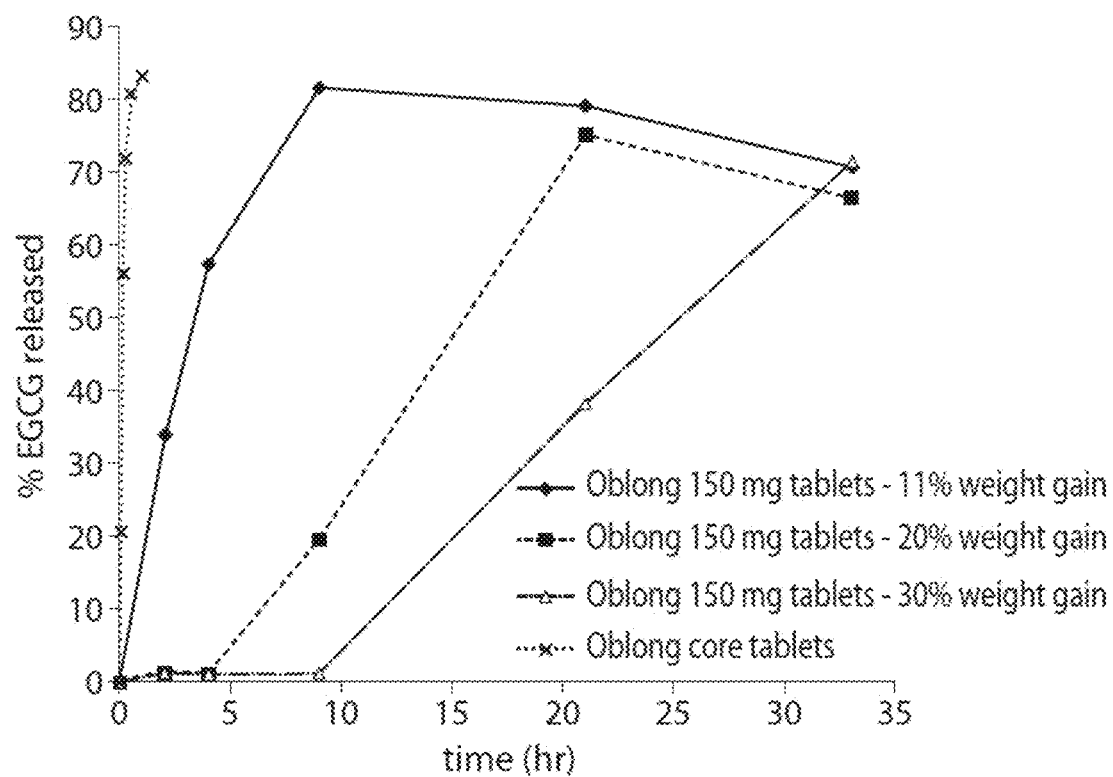
FIG. 1 shows cumulative release of EGCG from uncoated mini-tablets as well as coated tablets at different weight gains. Tables comprised a formulation containing 25% EGCG by weight, 150 mg in 600 mg weight of core tablets.
Figure 2:
FIG. 2 shows examples of mini-tablets. See, Rumondor et al., "Minitablets: Manufacturing, Characterization Methods, and Future Opportunities," American Pharmaceutical Review, Jul. 30, 2016, 190921; incorporated herein by reference.

The present disclosure relates to sustained release solid dosage forms of compositions comprising an active agent. In certain embodiments, the dosage form is for oral administration to a subject, and the dosage form is formulated to minimize systemic absorption of the active agent by the subject, and to maximize exposure to the active agent throughout the colon of a subject. For example, in certain embodiments, the dosage form releases no more than 5-25% of the active agent during the first 4 hours after administration, and not more than 75-85% of the active agent during the first 40 hours after administration. In certain embodiments, the dosage form releases no more than 5% of the active agent during the first 4 hours after administration, and not more than 75% of the active agent during the first 40 hours after administration. In certain embodiments, the dosage form releases no more than 25% of the active agent during the first 4 hours after administration, and not more than 85% of the active agent during the first 40 hours after administration.

In certain embodiments of the sustained-release solid dosage forms described herein, 30-80% (e.g., about 30%, about 40%, about 50%, about 60%, about 70%, or about 80%) of the active agent is released within 48 hours of administration a human subject. In certain embodiments, at least 60% (e.g., about 60%, about 70%, about 80%, about 90%, or about 100%) of the active agent is released within 72 hours of administration to a human subject. In certain embodiments, at least 75% (e.g., about 75%, about 80%, about 85%, about 90%, about 95%, or about 100%) of the active agent is released within 96 hours of administration to a human subject.

In certain embodiments of the sustained-release dosage forms described herein, 0-8% of the active agent is released at 4 hours following administration to a human subject, 30-60% of the active agent is released at 40 hours following administration, and at least 60% of the active agent is released at 75 hours following administration.

In certain embodiments of the sustained-release dosage forms described herein, 0-8% of the active agent is released at 4 hours following administration to a human subject, 40-80% of the active agent is released at 40 hours following administration, and at least 80% of the active agent is released at 75 hours following administration. In certain embodiments, the active agent is a polyphenol or an aminosterol.

In some embodiments of the dosage forms and methods disclosed herein, the active agent is a polyphenol. The term "polyphenol", "polyphenols", "polyphenolic" and the like, are art-recognized terms to a person of ordinary skill in the arts of organic, medicinal or pharmaceutical chemistry. In some embodiments, a polyphenol comprises a plurality of phenol moieties. In some embodiments, a polyphenol is a compound comprising a plurality of aromatic moieties which are in turn substituted by a plurality of hydroxyl and/or alkoxyl groups upon said aromatic moieties.

In some embodiments of the dosage forms and methods disclosed herein, the active agent is a polyphenol, and the polyphenol is a compound of Formula (I):

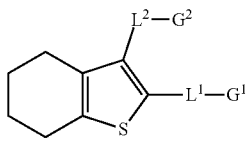

(I)

or a pharmaceutically acceptable salt thereof.

Formula (I), embodiments of Formula (I) provided herein, and pharmaceutically acceptable salts thereof, are defined as follows:

$L^1$ is a divalent moiety selected from a bond and —N($R^5$)(C=O)—.

$L^2$ is a divalent moiety selected from —(C=O)— and —(C=O)O—.

$G^1$ is a monovalent moiety selected from —N($R^5$)$_2$ and $R^6$. In certain embodiments, $G^1$ is —NH$_2$. In certain embodiments, $G^1$ is —NHR$^5$. In certain embodiments, $G^1$ is —N($R^5$)$_2$. In certain embodiments, $G^1$ is $R^6$.

$G^2$ is a monovalent moiety selected from —H, —N($R^5$)$_2$, and —N($R^5$)($R^6$). In certain embodiments, $G^2$ is —H. In certain embodiments, $G^2$ is —NH$_2$. In certain embodiments, $G^2$ is —NHR$^5$. In certain embodiments, $G^2$ is —N($R^5$)$_2$. In certain embodiments, $G^2$ is —NHR$^6$. In certain embodiments, $G^2$ is —N($R^5$)($R^6$).

Each $R^5$ is a monovalent moiety independently selected from —H and alkyl. In certain embodiments, $R^5$ is substituted $C_{1-6}$ alkyl. In certain embodiments, $R^5$ is unsubstituted $C_{1-6}$ alkyl. In certain embodiments, $R^5$ is methyl. In certain embodiments, $R^5$ is —H.

Each $R^6$ is aryl substituted with n instances of $R^7$. For each $R^6$, n is 0, 1, 2, 3, or 4. In certain embodiments, n is 0. In certain embodiments, n is 1. In certain embodiments, n is 2. In certain embodiments, n is 3. In certain embodiments, n is 4.

Each $R^7$ is independently selected from —F, —OH, and —O(alkyl). In certain embodiments, each $R^7$ is independently selected from —F, —OH, and —OCH$_3$. In certain embodiments, each $R^7$ is independently selected from —OH and —OCH$_3$. In certain embodiments, each $R^7$ is —OH. In certain embodiments, each $R^7$ is —OCH$_3$.

In certain embodiments, Formula (I) is of Formula (I-a):

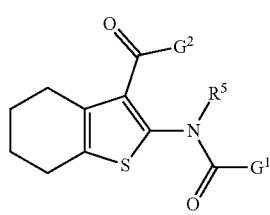

(I-a)

or a pharmaceutically acceptable salt thereof.

In certain embodiments of Formula (I-a):
$G^1$ is $R^6$;
$G^2$ is —NH$_2$ or —N($R^5$)($R^6$);
$R^5$ is —H or —CH$_3$;
$R^6$ is phenyl substituted with n instances of $R^7$;
$R^7$ is independently, for each occurrence, —F, —OH or —OCH$_3$; and
n is 0, 1, 2, 3, or 4.

In certain embodiments, Formula (I) is of Formula (I-b):

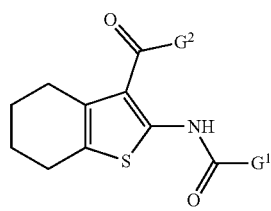

(I-b)

or a pharmaceutically acceptable salt thereof.

In certain embodiments, Formula (I-b) is of Formula (I-b-1) or Formula (I-b-2):

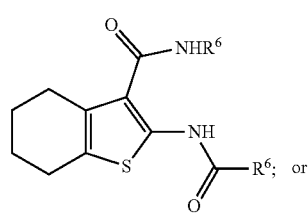

(I-b-1)

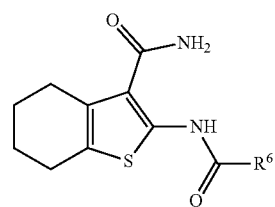

(I-b-2)

or a pharmaceutically acceptable salt thereof.

In certain embodiments, the compound of Formula (I), (I-a), (I-b), (I-b-1), or (I-b-2), or a pharmaceutically acceptable salt thereof, has 0-6 instances of $R^7$. In certain embodiments, the compound has 1-6 instances of $R^7$. In certain embodiments, the compound has 2-6 instances of $R^7$. In certain embodiments, the compound has 3-6 instances of $R^7$. In certain embodiments, the compound has 1-3 instances of $R^7$. In certain embodiments, the compound has 2-4 instances of $R^7$. In certain embodiments, the compound has 2 instances of $R^7$. In certain embodiments, the compound has 3 instances of $R^7$. In certain embodiments, the compound has 4 instances of $R^7$. In certain embodiments, the compound has 5 instances of $R^7$. In certain embodiments, the compound has 6 instances of $R^7$.

In certain embodiments of the compound of Formula (I), (I-a), (I-b), (I-b-1), or (I-b-2), or a pharmaceutically acceptable salt thereof, each $R^6$ is independently selected from:

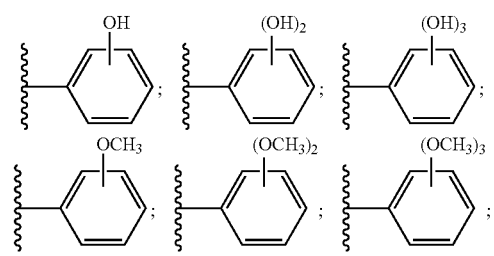

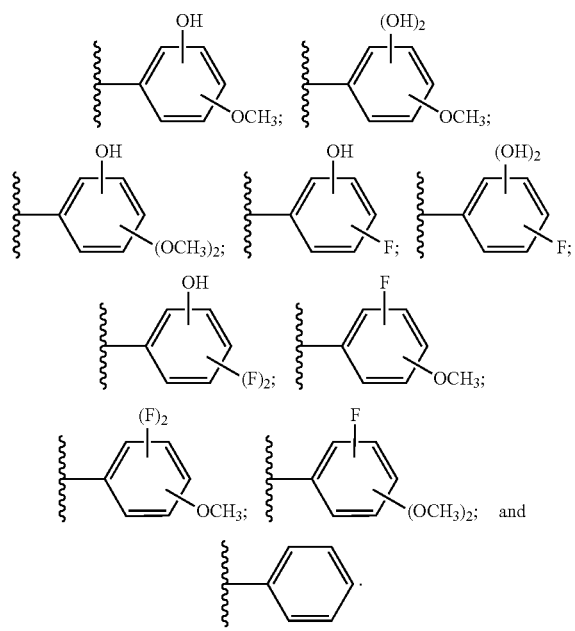

In certain embodiments of the compound of Formula (I), (I-a), (I-b), (I-b-1), or (I-b-2), or a pharmaceutically acceptable salt thereof, each $R^6$ is independently selected from:

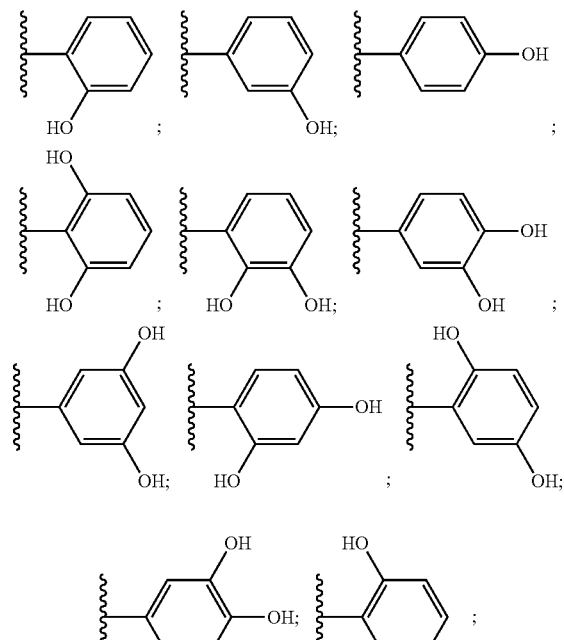

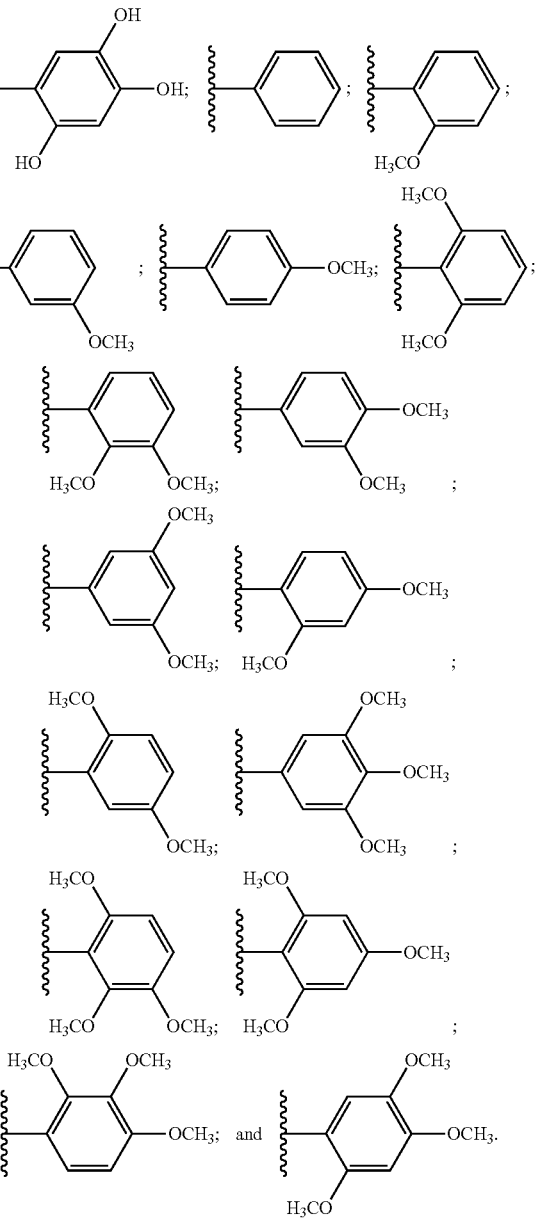

In certain embodiments, it is provided that the compound of Formula (I), (I-a), (I-b), (I-b-1), or (I-b-2):

(a) comprises at least one instance of $R^6$; and/or (b) comprises at least three instances of $R^7$; and/or (c) is not one of the following compounds:

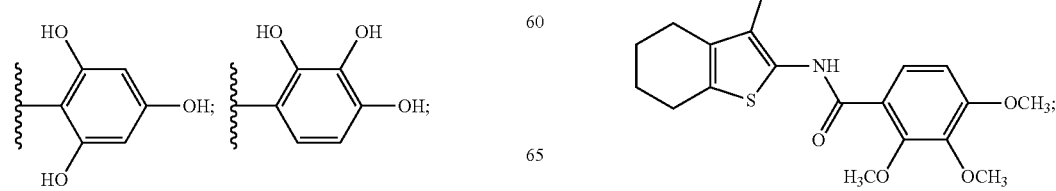

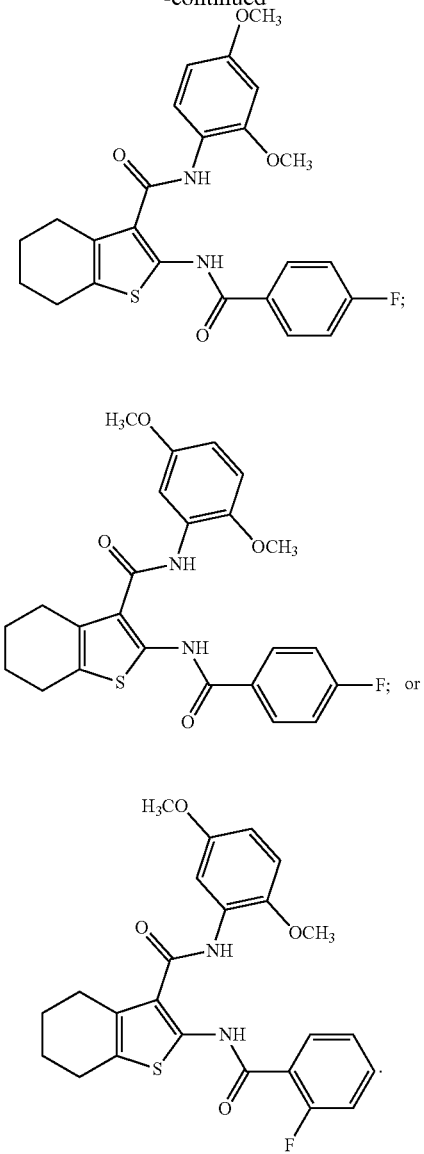
In certain embodiments, the compound of Formula (I), (I-a), (I-b), (I-b-1), or (I-b-2) is selected from the compounds of Table 1, and pharmaceutically acceptable salts thereof.
TABLE 1
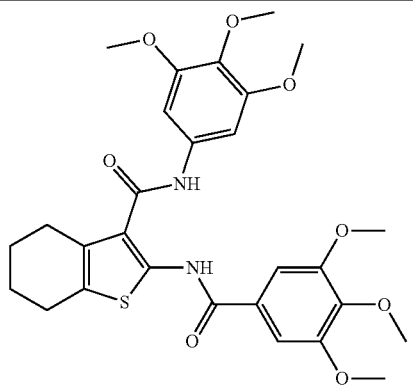
1
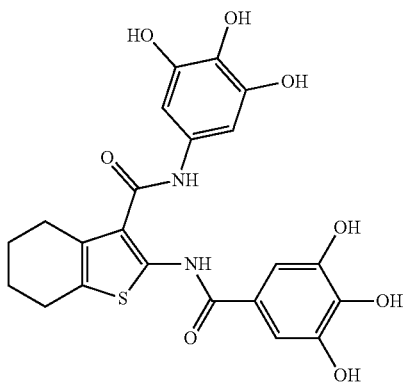 [SMILES: O=C(Nc1sc2c(c1C(=O)Nc1cc(O)c(O)c(O)c1)CCCC2)c1cc(O)c(O)c(O)c1]
2
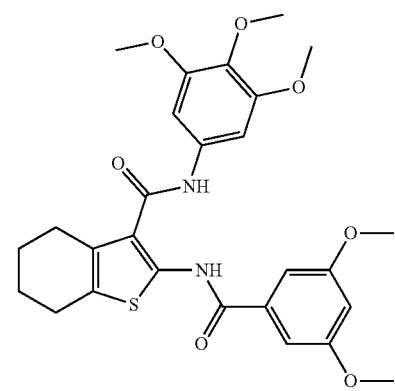 [SMILES: COc1cc(OC)cc(C(=O)Nc2sc3c(c2C(=O)Nc2cc(OC)c(OC)c(OC)c2)CCCC3)c1]
3
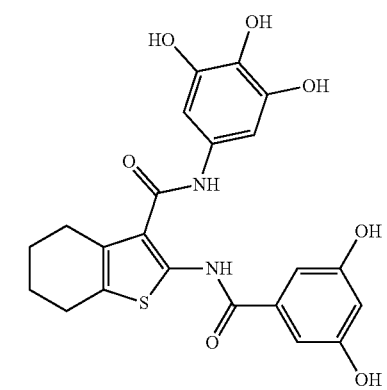 [SMILES: O=C(Nc1sc2c(c1C(=O)Nc1cc(O)c(O)c(O)c1)CCCC2)c1cc(O)cc(O)c1]
4
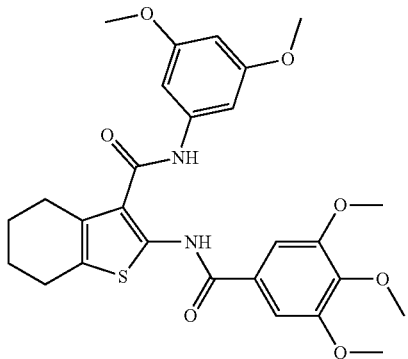 [SMILES: COc1cc(NC(=O)c2c(NC(=O)c3cc(OC)c(OC)c(OC)c3)sc3c2CCCC3)cc(OC)c1]
5

TABLE 1-continued
6
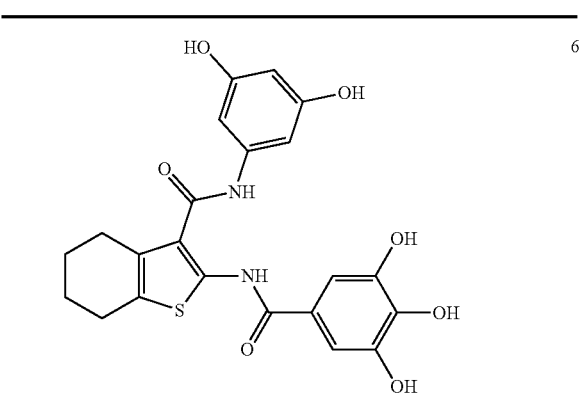
7
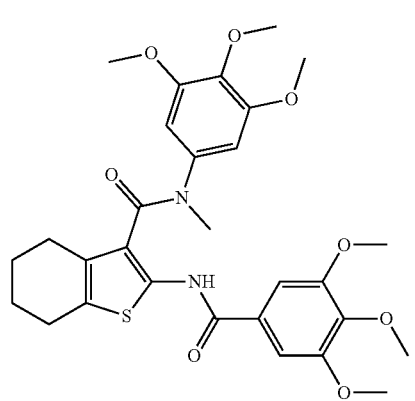 [SMILES: COc1cc(C(=O)Nc2sc3c(c2C(=O)N(C)c2cc(OC)c(OC)c(OC)c2)CCCC3)cc(OC)c1OC]
8
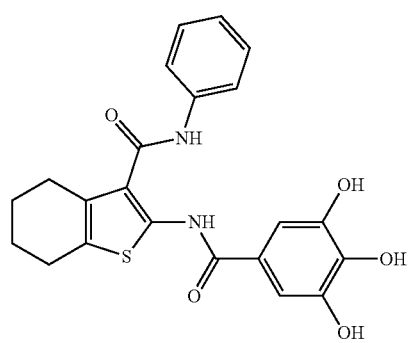 [SMILES: O=C(Nc1sc2c(c1C(=O)Nc1ccccc1)CCCC2)c1cc(O)c(O)c(O)c1]
9
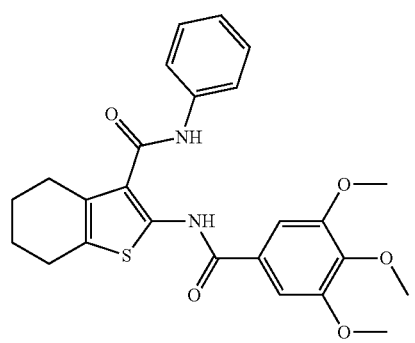 [SMILES: COc1cc(C(=O)Nc2sc3c(c2C(=O)Nc2ccccc2)CCCC3)cc(OC)c1OC]
TABLE 1-continued
10
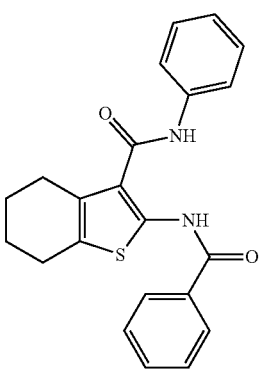 [SMILES: O=C(Nc1sc2c(c1C(=O)Nc1ccccc1)CCCC2)c1ccccc1]
11
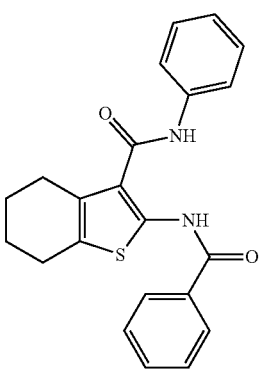 [SMILES: O=C(Nc1sc2c(c1C(=O)Nc1ccccc1)CCCC2)c1ccccc1]
12
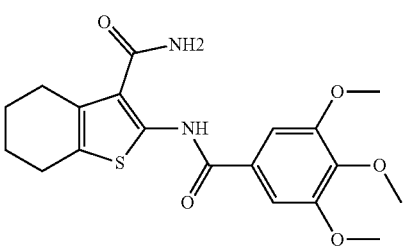 [SMILES: COc1cc(C(=O)Nc2sc3c(c2C(N)=O)CCCC3)cc(OC)c1OC]
13
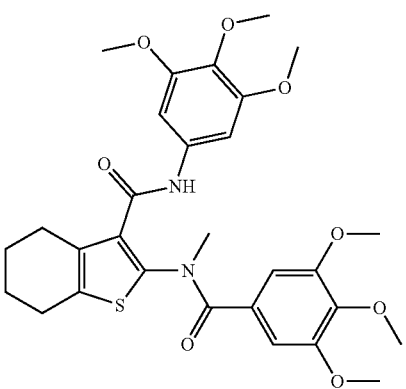 [SMILES: COc1cc(NC(=O)c2c(N(C)C(=O)c3cc(OC)c(OC)c(OC)c3)sc3c2CCCC3)cc(OC)c1OC]

TABLE 1-continued

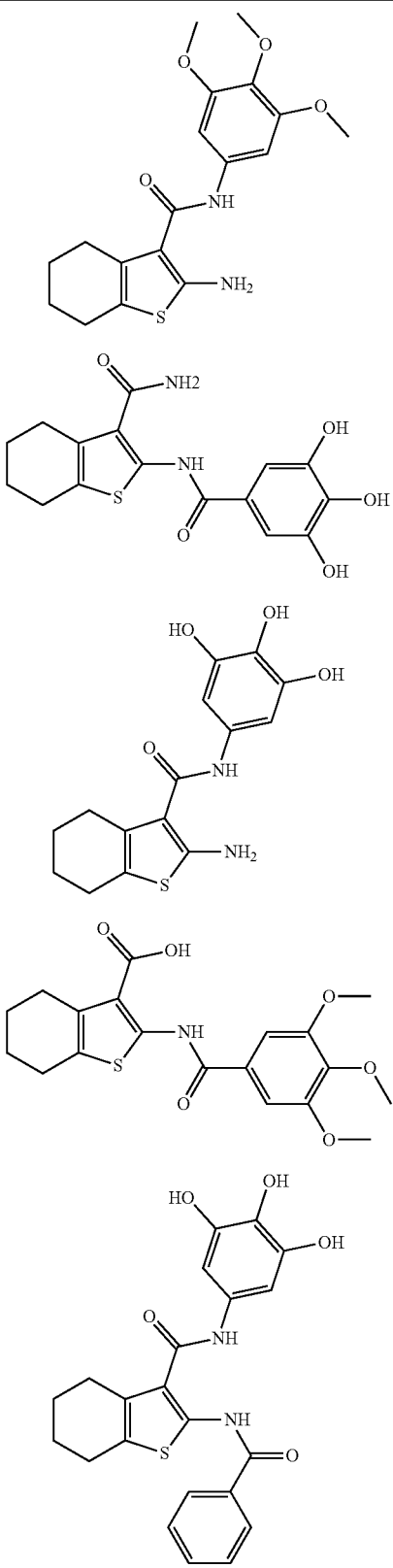

In some embodiments of the dosage forms and methods disclosed herein, the polyphenol is a compound of Formula (II):

$$\text{(II)}$$

or a pharmaceutically acceptable salt thereof.

Formula (II), embodiments of Formula (II) provided herein, and pharmaceutically acceptable salts thereof, are defined as follows.

$L^1$ is a bond.

$L^2$ is a divalent moiety selected from a bond, —CH$_2$—, —(C═O)—, —(C═O)O—, and —NR$^2$(C═O)—.

$G^1$ is a monovalent moiety selected from —H and R$^3$. In certain embodiments, $G^1$ is —H. In certain embodiments, $G^1$ is R$^3$.

$G^2$ is a monovalent moiety selected from —H, —N(R$^2$)$_2$, —N(R$^2$)(R$^3$), and R$^3$. In certain embodiments, $G^2$ is —H. In certain embodiments, $G^2$ is —N(R$^2$)$_2$. In certain embodiments, $G^2$ is —NH$_2$. In certain embodiments, $G^2$ is —N(C$_{1-6}$ alkyl)$_2$. In certain embodiments, $G^2$ is —N(R$^2$)(R$^3$). In certain embodiments, $G^2$ is R$^3$.

R is a monovalent moiety selected from —H and alkyl. In certain embodiments, R is substituted C$_{1-6}$ alkyl. In certain embodiments, R is unsubstituted C$_{1-6}$ alkyl. In certain embodiments, R is methyl. In certain embodiments, R is —H.

Each R$^1$ is independently selected from —F, —OH, and —O(alkyl). In certain embodiments, each R$^1$ is independently selected from —F, —OH, and —OCH$_3$. In certain embodiments, each R$^1$ is independently selected from —OH and —OCH$_3$. In certain embodiments, each R$^1$ is —OH. In certain embodiments, each R$^1$ is —OCH$_3$.

Each R$^2$ is a monovalent moiety independently selected from —H and alkyl. In certain embodiments, R$^2$ is substituted C$_{1-6}$ alkyl. In certain embodiments, R$^2$ is unsubstituted C$_{1-6}$ alkyl. In certain embodiments, R$^2$ is methyl. In certain embodiments, R$^2$ is —H.

Each R$^3$ is aryl substituted with n instances of R$^4$. For each R$^3$, n is 0, 1, 2, 3, or 4. In certain embodiments, n is 0. In certain embodiments, n is 1. In certain embodiments, n is 2. In certain embodiments, n is 3. In certain embodiments, n is 4.

Each R$^4$ is independently selected from —F, —OH, and —O(alkyl). In certain embodiments, each R$^4$ is independently selected from —F, —OH, and —OCH$_3$. In certain embodiments, each R$^4$ is independently selected from —OH and —OCH$_3$. In certain embodiments, each R$^4$ is —OH. In certain embodiments, each R$^7$ is —OCH$_3$.

m is 0, 1, 2, 3, or 4. In certain embodiments, m is 0. In certain embodiments, m is 1. In certain embodiments, m is 2. In certain embodiments, m is 3. In certain embodiments, m is 4.

In certain embodiments,
$L^1$ is a bond;
$L^2$ is a bond, —CH$_2$—, —(C═O)—, —(C═O)O—, or —NR$^2$(C═O)—;
$G^1$ is —H or R$^3$;
$G^2$ is —N(R$^2$)(R$^3$) or R$^3$;
R is H or —CH$_3$;
R$^1$ is —OH or —OCH$_3$;
R$^2$ is —H or —CH$_3$;

$R^3$ is phenyl substituted with m instances of $R^4$;

$R^4$ is independently, for each occurrence, —F, —OH or —OCH$_3$;

n is, for each occurrence 0, 1, 2, 3, or 4; and m is 0, 1, 2, 3, or 4.

In certain embodiments, Formula (II) is of Formula (II-a) or Formula (II-b):

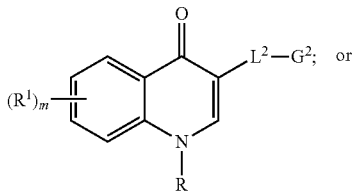
(II-a)

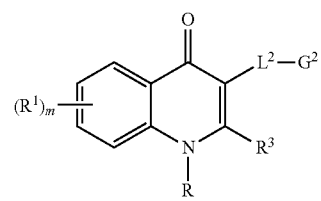
(II-b)

or a pharmaceutically acceptable salt thereof.

In certain embodiments, Formula (II-a) is of Formula (II-a-1) or Formula (II-a-2):

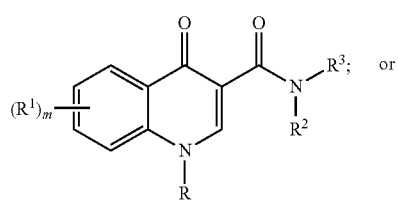
(II-a-1)

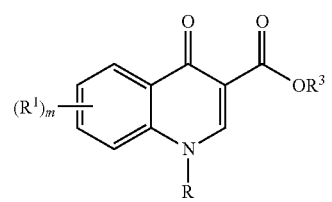
(II-a-2)

or a pharmaceutically acceptable salt thereof.

In certain embodiments, Formula (II-b) is of Formula (II-b-1) or Formula (II-b-2):

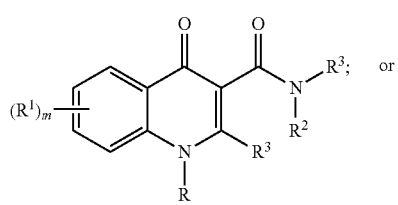
(II-b-1)

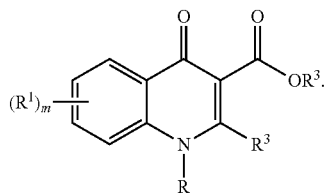
(II-b-2)

or a pharmaceutically acceptable salt thereof.

In certain embodiments, the compound of Formula (II), (II-a), (II-a-1), (II-a-2), (II-b), (II-b-1), (II-b-2), or a pharmaceutically acceptable salt thereof, has 0-6 instances of $R^4$. In certain embodiments, the compound has 1-6 instances of $R^4$. In certain embodiments, the compound has 2-6 instances of $R^4$. In certain embodiments, the compound has 3-6 instances of $R^4$. In certain embodiments, the compound has 1-3 instances of $R^4$. In certain embodiments, the compound has 2-4 instances of $R^4$. In certain embodiments, the compound has 2 instances of $R^4$. In certain embodiments, the compound has 3 instances of $R^4$. In certain embodiments, the compound has 4 instances of $R^4$. In certain embodiments, the compound has 5 instances of $R^4$. In certain embodiments, the compound has 6 instances of $R^4$.

In certain embodiments of the compound of Formula (II), (II-a), (II-a-1), (II-a-2), (II-b), (II-b-1), (II-b-2), or a pharmaceutically acceptable salt thereof, the sum of all instances of m and n is 0-9. In certain embodiments, the sum is 1-9. In certain embodiments, the sum is 2-9. In certain embodiments, the sum is 3-9. In certain embodiments, the sum is 4-9. In certain embodiments, the sum is 5-9. In certain embodiments, the sum is 6-9. In certain embodiments, the sum is 1-6. In certain embodiments, the sum is 2-6. In certain embodiments, the sum is 3-6. In certain embodiments, the sum is 1-3. In certain embodiments, the sum is 2. In certain embodiments, the sum is 3. In certain embodiments, the sum is 4. In certain embodiments, the sum is 5. In certain embodiments, the sum is 6. In certain embodiments, the sum is 7. In certain embodiments, the sum is 8. In certain embodiments, the sum is 9.

In certain embodiments of the compound of Formula (II), (II-a), (II-a-1), (II-a-2), (II-b), (II-b-1), (II-b-2), or a pharmaceutically acceptable salt thereof, each $R^3$ is independently selected from:

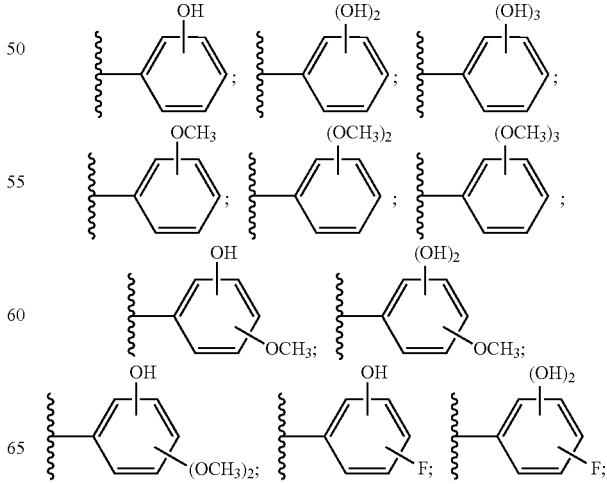

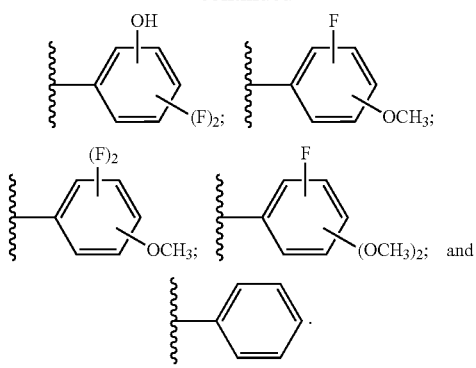

In certain embodiments of the compound of Formula (II), (II-a), (II-a-1), (II-a-2), (II-b), (II-b-1), (II-b-2), or a pharmaceutically acceptable salt thereof, each $R^3$ is independently selected from:

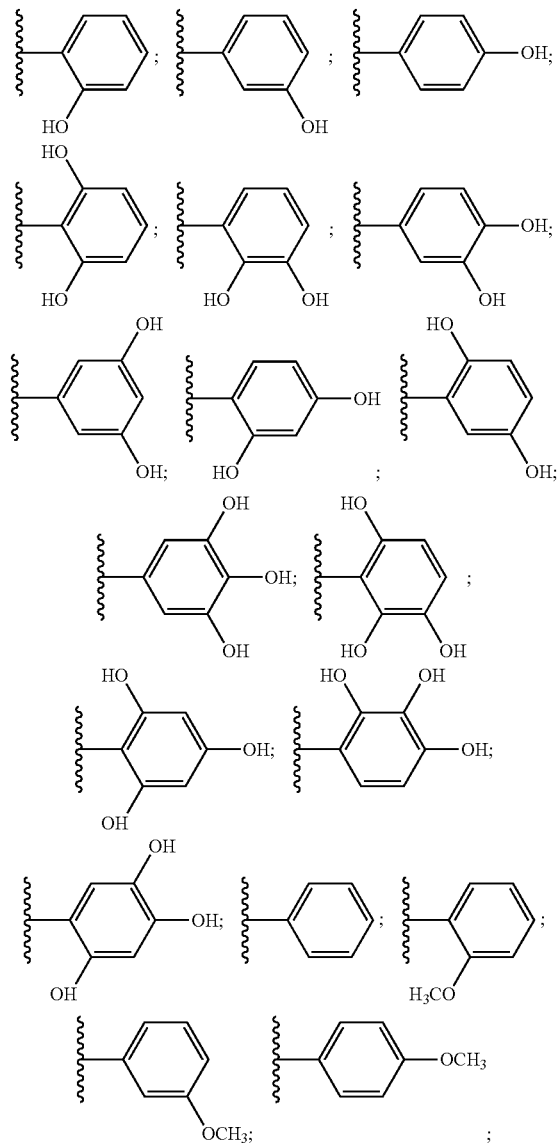

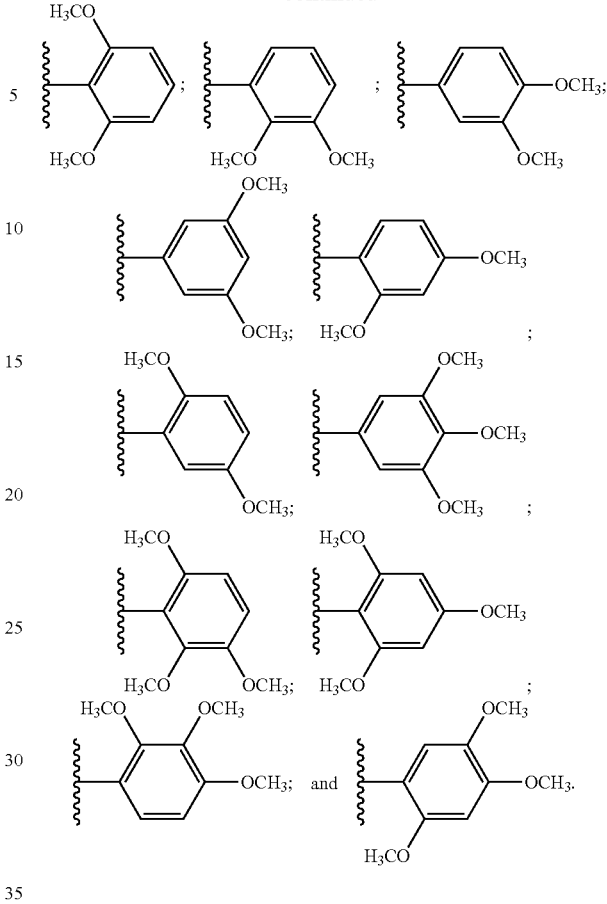

In certain embodiments of the compound of Formula (II), (II-a), (II-a-1), (II-a-2), (II-b), (II-b-1), or (II-b-2), it is provided that:

(a) the compound comprises at least one instance of $R^3$; and/or (b) the sum of all instances of m and n is at least three; and/or (c) the compound does not have the structure:

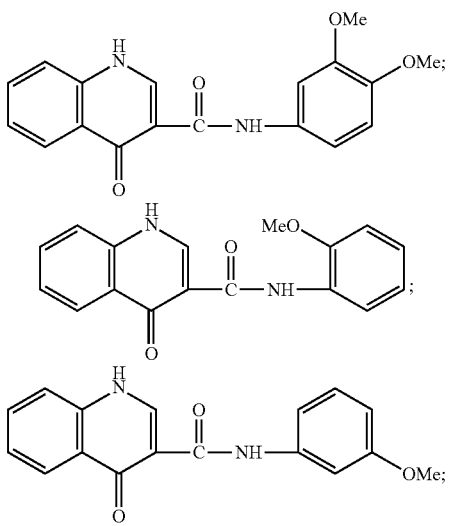

-continued
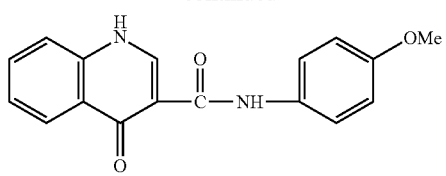
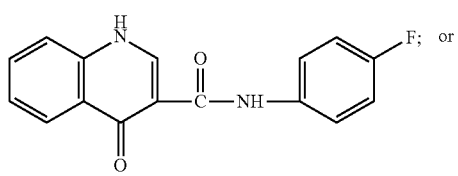
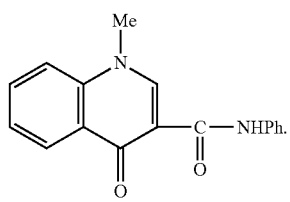
In certain embodiments, the compound of Formula (II), (II-a), (II-a-1), (II-a-2), (II-b), (II-b-1), or (II-b-2) is selected from the compounds of Table 2, and pharmaceutically acceptable salts thereof.
TABLE 2
19
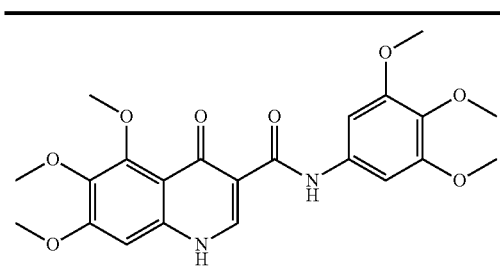
20
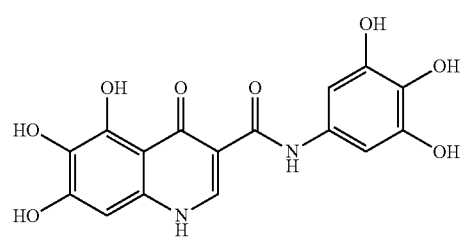 [SMILES: O=C(Nc1cc(O)c(O)c(O)c1)c1c[nH]c2cc(O)c(O)c(O)c2c1=O]
21
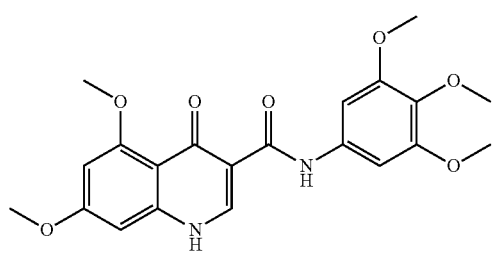
TABLE 2-continued
22
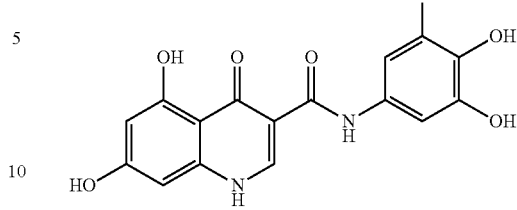
23
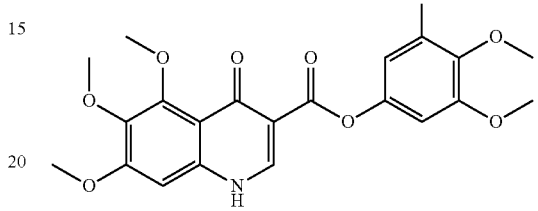
24
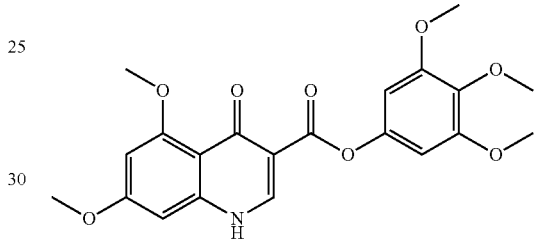
25
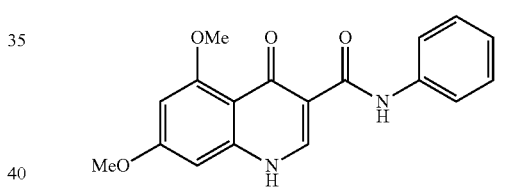
26
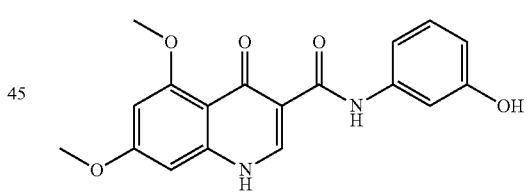
27
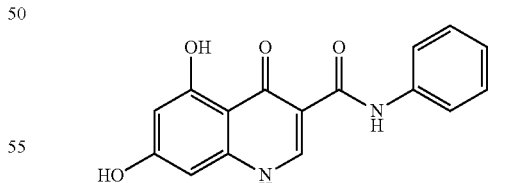
28
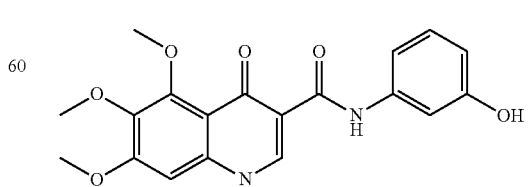

TABLE 2-continued
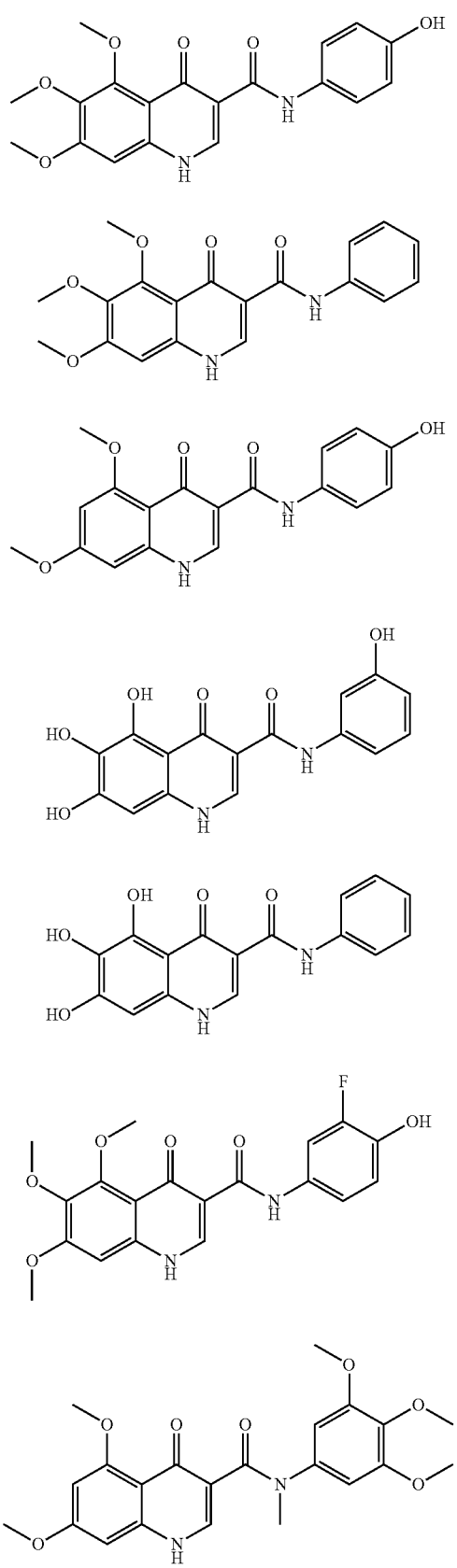
TABLE 2-continued
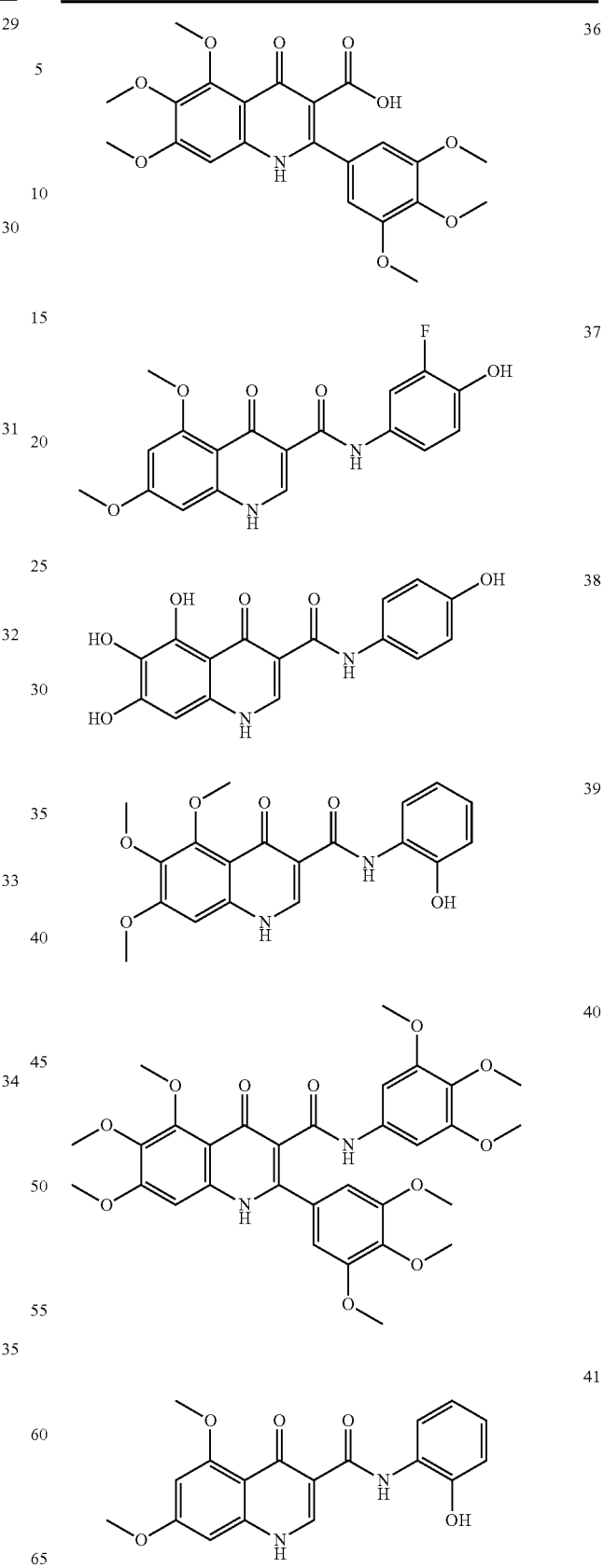

TABLE 2-continued

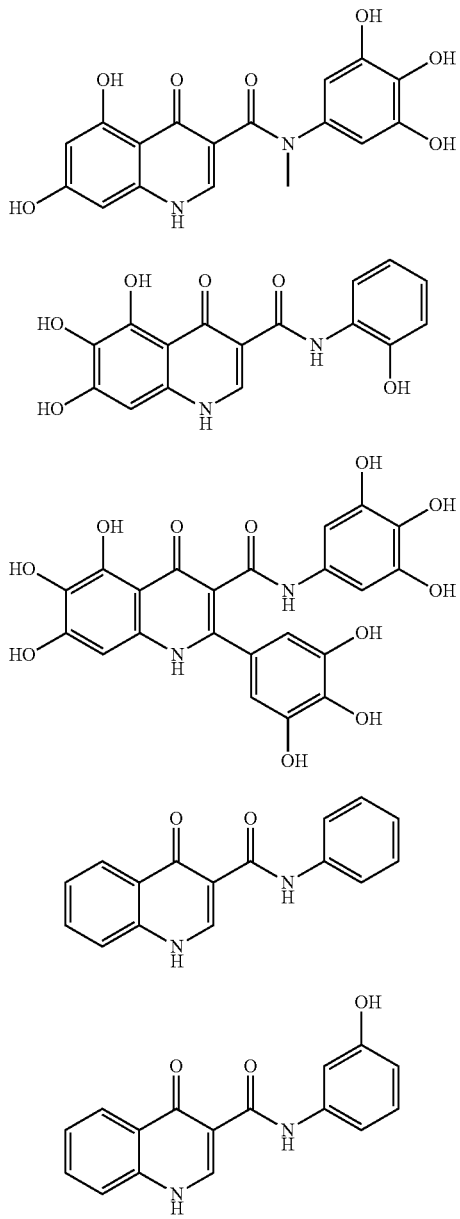

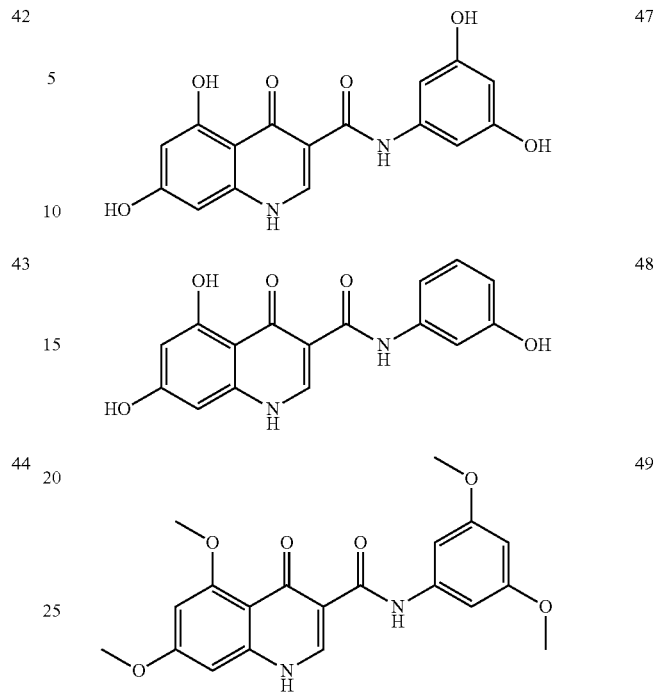

Compounds of Formulae (I) and (II), subgeneric formulae thereof, and syntheses thereof, are described in International Publication Number WO 2019/028456A1, the contents of which is incorporated by reference.

In some embodiments of the dosage forms and methods disclosed herein, the active agent is a polyphenol, and the polyphenol is epigallocatechin gallate (EGCG), or a pharmaceutically acceptable salt thereof. EGCG and related polyphenolic compounds are described in International Publication Number WO 2018/213204, the contents of which is incorporated by reference.

In some embodiments of the dosage forms and methods disclosed herein, the active agent is an aminosterol. Aminosterols (also referred to as polyamine-steroids) are compounds having a characteristic tetracyclic steroid core and two or more amine functional groups. In a particular embodiment, the aminosterol is squalamine, or a pharmaceutically acceptable salt thereof. In another particular embodiment, the aminosterol is Aminosterol 1436, or a pharmaceutically acceptable salt thereof.

For convenience, before further description of the invention, definitions of certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-10}$ alkyl (such as substituted $C_{1-6}$ alkyl, e.g., —$CH_2F$, —$CHF_2$, —$CF_3$ or benzyl (Bn)). An alkyl group may be branched or unbranched.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{1-4}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents (e.g., —F, —OH or —O($C_{1-6}$ alkyl). In certain embodiments, the aryl group is an unsubstituted $C_{6-14}$ aryl. In certain embodiments, the aryl group is a substituted $C_{6-14}$ aryl.

The articles "a" and "an" are used herein to refer to one or to more than one (i.e., to at least one) of the grammatical object of the article. By way of example, "an element" means one element or more than one element.

The terms "comprise" and "comprising" are used in the inclusive, open sense, meaning that additional elements may be included.

The term "including" is used to mean "including but not limited to." "Including" and "including but not limited to" are used interchangeably.

The term "subject" refers to a mammal in need of a particular treatment. In certain embodiments, a subject is a primate, bovine, canine, feline, porcine, or equine. In certain embodiments, a subject is a human.

The term "multiparticulate" or "multiple unit dosage forms", refers to discrete, small units of drug-containing particulates that together make up a single dose. Units may be of the same drug-containing particulates having the same, or different, properties. Individual units may vary in size, and may have a diameter ranging from 0.001 mm to 10 mm.

The term "tablet" refers to a compressed, solid dosage form of a drug substance comprising one or more active agents and optionally one or more excipients.

The term "mini-tablet" refers to a small tablet form, typically a diameter as described in various embodiments herein (e.g., 1-4 mm). A mini-tablet-containing unit dosage form may contain multiple mini-tablets, wherein the mini-tablets may have the same, or different, properties.

The term "bead" refers to a small drug-containing particulate that is generally spherical in shape. A typical bead-containing unit dosage form contains multiple beads, wherein the beads may have the same, or different, properties.

The term "granule" refers to aggregates of fine particles of a powder that are approximately spherical in shape. A typical granule-containing unit dosage form contains multiple granules that may have same, or different, properties.

The term "pellet" refers to small, free-flowing, spherical, oblong or cylindrical agglomerates of fine powders or granules.

The terms "co-administration" and "co-administering" refer to both concurrent administration (administration of two or more therapeutic agents, or a therapeutic agent and a testing system, at the same time) and time-varied administration (administration of one or more therapeutic agents at a time different from that of the administration of an additional therapeutic agent or agents or testing system). In certain embodiments, the therapeutic agents are present in the subject to some extent at the same time. In other embodiments, a first therapeutic agent is considered to be co-administered with a second therapeutic agent when it is administered following elimination or clearance of the second therapeutic agent from the subject.

In certain embodiments, the term "pharmaceutical composition" refers to a composition comprising at least one active ingredient or agent, nutraceutical, nutritional supplement, or vitamin substance.

In certain embodiments, the terms "active ingredient" and "active agent" synonymously refer to a material that is biologically (e.g., pharmaceutically) active. In certain other embodiments, the active ingredient/agent further promotes or achieves a therapeutic goal. In certain embodiments, the active ingredient/agent is a polyphenol or an aminosterol. In a particular embodiment, the active ingredient/agent is EGCG. In a particular embodiment, the active ingredient/agent is an aminosterol.

In certain embodiments, the invention provides pharmaceutically acceptable compositions comprising a therapeutically-effective amount of an active agent, formulated together with one or more pharmaceutically acceptable carriers (additives) and/or diluents. In certain embodiments, the active agent is a polyphenol or an aminosterol. In a particular embodiment, the active agent is EGCG. In a particular embodiment, the active agent is an aminosterol. As described in detail below, the pharmaceutical compositions of the invention may be specially formulated for administration in solid form, including those adapted for oral administration (for example, tablets and encapsulated solid particulates).

The phrase "therapeutically-effective amount" as used herein means that amount of a therapeutic agent in a composition of the invention which is effective for producing some desired therapeutic effect in at least a sub-population of cells in an animal at a reasonable benefit/risk ratio applicable to any medical treatment.

The phrase "pharmaceutically acceptable" is an art recognized term, and is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrases "release rate controlling polymer" and "release rate control polymer" are art recognized terms, and as used herein mean a polymer that modifies or modulates the rate at which one or more active ingredients, nutraceuticals, nutritional supplements, or vitamin substances are made available to organism.

The term "insoluble polymer" is an art recognized term, and as used herein means a polymer that possesses aqueous solubility of about less than 0.01 g/mL. "Water insoluble polymers" are typically hydrophobic polymers. Non-limiting examples include hydrocarbon polymers such as polyethylene, and polypropylene, silicone-based polymers, and high molecular weight and/or highly-crosslinked polymers.

The terms "slow dissolving polymer" and "slowly soluble polymer" are art recognized terms, and as used herein mean polymers that have a low intrinsic dissolution rate, from a compacted solid surface, of about less than 1 mm/hr.

The terms "matrix" and "matrix-type sustained release dosage" are art recognized terms, and as used herein refer to solid dosage forms comprising one or more active agents or additional therapeutic agents embedded in one or more insoluble or slowly soluble polymers.

The phrases "osmotic pump", "elementary osmotic pump (EOP)", "push pull osmotic pump (PPOP)" and the like, are art recognized terms and as used herein refer to systems used for the delivery of both poorly water-soluble and highly water soluble biologically-active materials at a constant rate. Such systems may, in some embodiments, comprise a first drug layer, a second drug layer and a push layer. In some embodiments, said first drug layer, second drug layer and push layer are surrounded by a semi-permeable membrane. In some embodiments, the semi-permeable layer further comprises an exit hole. In some embodiments, the push layer comprises a material, such as a swellable polymer, which expands as it absorbs water and pushes the first and/or second drug layers out of said exit hole at a controlled rate.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations. Proper fluidity can be maintained, for example, by the product of coating materials, such as lecithin, by the maintenance of the required particle size in the case of dispersions, and by the product of surfactants.

Specific examples of pharmaceutically acceptable carriers and excipients that may be used to formulate oral dosage forms are described in the Handbook of Pharmaceutical Excipients, Pharmaceutical Press, 6$^{th}$ edition: 2009.

The term "pharmaceutically-acceptable salts" refers to the relatively non-toxic, inorganic and organic acid addition salts of a compound disclosed herein. These salts can be prepared in situ in the administration vehicle or the dosage form manufacturing process, or by separately preparing the compound with a suitable organic or inorganic compound, and isolating the salt thus formed during subsequent purification.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In certain embodiments, a formulation of the invention comprises an excipient selected from the group consisting of cyclodextrins, celluloses, liposomes, micelle forming agents, e.g., bile acids, and polymeric carriers, e.g., polyesters and polyanhydrides. In certain embodiments, an aforementioned formulation renders orally bioavailable a composition of the invention.

Prevention of the action of microorganisms upon the constituents of the dosage forms described herein may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions.

Methods of preparing these formulations or compositions include the step of bringing into association the active agent with the carrier and, optionally, one or more accessory ingredients. In general, the formulations are prepared by uniformly and intimately bringing into association the active agent with liquid carriers, or finely divided solid carriers, or both, and then, if necessary, shaping the product. In certain embodiments, the active agent is a polyphenol or an aminosterol. In a particular embodiment, the active agent is EGCG. In a particular embodiment, the active agent is an aminosterol.

In certain embodiments, formulations of the invention include those suitable for oral administration. The formulations may conveniently be presented in unit dosage form and may be prepared by any methods well known in the art of pharmacy. The amount of active ingredients which can be combined with a carrier material to produce a single dosage form will vary depending upon the host being treated and the particular mode of administration. The amount of active ingredients which can be combined with a carrier material to produce a single dosage form will generally be those amounts of the compounds which produce a therapeutic effect. Formulations of the invention suitable for oral administration may be in the form of solid particulates (e.g., mini-tablets, beads, granules, and pellets), individual (i.e., single) solid dosage forms, capsules, tablets, capsules encompassing solid particulates, or capsules comprising a plurality of mini-tablets. In one embodiment is provided a dosage form comprising a capsule, the capsule comprising a plurality of mini-tablets, each mini-tablet comprising a core comprising and active agent and one or more pharmaceutically acceptable excipients, the core being coated with a coating material comprising a hydrophobic and a hydrophilic polymer. In certain embodiments, the active agent is a polyphenol or an aminosterol. In a particular embodiment, the active agent is EGCG. In a particular embodiment, the active agent is an aminosterol.

In another aspect, described herein is a process of manufacturing sustained release solid dosage forms as described herein, comprising mixing or granulating a mixture of an active agent and optional excipients; optionally drying the mixture to a residual amount of water of 0-10% (e.g., 0-0.5%, 0-1%, 1-2%, 2-3%, 3-4%, 4-5%, 5-6%, 6-7%, 7-8%, 8-9%, or 9-10%); directly compressing said mixture into solid particulates; optionally coating the solid particulates with an optional undercoat or second coat composition comprising a water-soluble polymer; and further coating the solid particulates with a first coat or top-coat with a first coat or topcoat composition comprising a polymer that modifies release of the active agent. In certain embodiments, the active agent is a polyphenol or an aminosterol. In a particular embodiment, the active agent is EGCG. In a particular embodiment, the active agent is an aminosterol.

In yet another aspect, described herein is a multiparticulate dosage form comprising a plurality of coated mini-tablets wherein each coated mini-tablet comprises a mini-tablet core having a diameter of in the range of 0.1-7 mm (e.g., 0.1 mm, 1 mm, 2.25 mm, or 4 mm) and comprises an active agent, microcrystalline cellulose, hydroxypropyl cellulose, and a lubricant; an optional undercoat surrounding said core which comprises a water soluble polymer; a first coat or topcoat which comprises ethyl cellulose surrounding said optional undercoat that modifies the release of the active agent; a first coat or topcoat which comprises ethyl cellulose surrounding said optional undercoat that modifies the release of the active agent; a release rate controlling polymer in the first coat or topcoat; and wherein at least 65% of said coated mini-tablets exhibit substantially the same release profile. In certain embodiments, the active agent is a polyphenol or an aminosterol. In a particular embodiment, the active agent is EGCG. In a particular embodiment, the active agent is an aminosterol.

In yet another aspect, described herein is a multiparticulate dosage form comprising a plurality of coated mini-tablets wherein each coated mini-tablet comprises a mini-tablet core having a diameter of in the range of 0.1-7 mm (e.g., 0.1 mm, 1 mm, 2.25 mm, or 4 mm) and comprises an active agent, lactose monohydrate, hydroxypropyl cellulose, and a lubricant; an optional undercoat surrounding said core which comprises a water soluble polymer; a first coat or topcoat which comprises ethyl cellulose surrounding said optional undercoat that modifies the release of the active agent; a release rate controlling polymer in the first coat or topcoat; and wherein at least 65% of said coated mini-tablets exhibit substantially the same release profile. In certain embodiments, the active agent is a polyphenol or an aminosterol. In a particular embodiment, the active agent is EGCG. In a particular embodiment, the active agent is an aminosterol.

Multiparticulate pharmaceutical dosage formulations as described herein may contain coated solid particulates that comprise cores with an active pharmaceutical agent and any optional excipients. In one embodiment, the cores are made by first mixing or granulating an active agent along with any optional excipients to obtain a compressible blend. In some embodiments, the cores are microcrystalline cellulose based. In some embodiments, the cores are lactose based. Mixing or granulation can be achieved by any known method and can include high shear mixing (impeller and chopper), wet granulation or dry granulation. The employed mixing or granulation method is dependent on the identity of the active agent as well as any added excipients. Suitable equipment for mixing or granulation comprise Bohle Vagumators, Gral Granulators, Key International KG-5 Granulators, or the like. In certain embodiments, the active agent is a polyphenol or an aminosterol. In a particular embodiment, the active agent is EGCG. In a particular embodiment, the active agent is an aminosterol.

In some embodiments, solid particulate cores contain between about 0.01 mg to about 50 mg of active agent per core. In certain embodiments, the cores contain about 25 mg of active agent. In certain instances, the cores contain between about 1 mg to about 15 mg of active agent per core and in other instances, the cores contain between about 5 mg to about 10 mg, about 5 mg to about 9 mg, about 5 mg to about 8 mg, about 5 mg, about 6 mg, about 7 mg, about 9 mg, about 10 mg, about 11 mg, about 12 mg, about 13 mg, about 14 mg, about 15 mg, about 16 mg, about 17 mg, about 18 mg, about 19 mg, or about 20 mg of active agent per core. In some embodiments, the cores contain about 7.8 mg of active agent per core. Cores and their coated forms can collectively be aggregated together to provide dosage forms of about 1 mg to about 2000 mg of active agent; about 100 mg to about 800 mg of active agent; about 200 mg, about 250 mg, about 400 mg, about 500 mg, about 600 mg, or about 800 mg active agent. In some embodiments, solid particulate cores contain between about 0.01 mg to about 1 mg of active agent per core. In certain embodiments, the cores contain about 0.1 mg, 0.2 mg, 0.3 mg, 0.4 mg, 0.5 mg, 0.6 mg, 0.7 mg, 0.8 mg, 0.9 mg, or 1 mg of active agent. In certain embodiments, the active agent is a polyphenol or an aminosterol. In a particular embodiment, the active agent is EGCG. In a particular embodiment, the active agent is an aminosterol.

For wet granulations, the wet granules are subjected to a drying process facilitated by a fluid bed dryer, microwave, nitrogen drying, evaporation, vacuum drying or heatable jacketed process vessel wall. The drying process can be combined with heat of about 50° C., about 60° C., about 70° C., about 80° C., about 90° C., about 100° C., or a temperature effective to dry the wet granulations without degrading the active agent and/or excipients. The resultant dried granules have a residual amount of water of about 0.5% to about 10%, or about 1% to about 10%. The control of the residual water content in the dried granules may be made for example, by taking samples of the dried granules and annealing them in an oven with an oven temperature of about 80° C. to about 125° C., for example about 90° C., about 95° C., about 100° C., or about 105° C., while measuring water loss. In certain embodiments, the active agent is a polyphenol or an aminosterol. In a particular embodiment, the active agent is EGCG. In a particular embodiment, the active agent is an aminosterol.

In wet and dry granulations, the dried granules are passed through mesh screens of size, for example #20 US, #25 US, #30 US, #35 US or #40 US, #45 US, or #75 US, and collected to be compressed into mini-tablets. Granules that do not pass through the desired mesh size are optionally subjected to an oscillator (Erweka AMD) or additional milling or other processing followed by passage through additional one or more mesh screens.

The granules or mixed powders are compressed into mini-tablet cores with diameters of about 1.5 mm to about 7 mm, such as, for example, about 2 mm, about 2.25 mm, about 2.5 mm, about 2.75 mm, about 3 mm, about 3.25 mm, about 3.5 mm, about 3.75 mm, about 4 mm, about 4.25 mm, about 4.5 mm, about 4.75 mm, about 5 mm, about 5.25 mm, about 5.5 mm, about 5.75 mm, about 6 mm, about 6.25 mm, about 6.5 mm, about 6.75 mm, or about 7 mm in diameter. In one embodiment, granules or mixed powders are compressed into mini-tablet cores with diameters of 2.25 mm, or about 2.5 mm. Lubricants are added to the tableting procedure to prevent tablets from sticking to the tablet dies and punches. Lubricant concentrations range from under 1% to about 5% of the total tablet mass, for example about 0.5%, about 1%, about 2%, about 3%, about 4% or about 5%. Mini-tablet cores can be compressed into any shape including but not limited to spherical, flat disk, capsule, convex, concave, polygonal or the like. Suitable tableting equipment include rotary tablet machines such as Vector-Colton 2216, Stokes/Pennwalt 555-2 or Manesty Betapress.

In solid dosage forms of the invention for oral administration (capsules, capsules comprising a plurality of solid particulates), the active agent is mixed with one or more pharmaceutically-acceptable carriers, such as sodium citrate or dicalcium phosphate, and/or any of the following: (1) fillers or extenders, such as starches, microcrystalline cellulose, lactose, sucrose, glucose, mannitol, and/or silicic acid; (2) binders, such as, for example, hydroxypropyl cellulose, hypromellose, or hydroxypropyl methylcellulose (HPMC), carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) sustained release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like. In certain embodiments, the manufacture of tablets, capsules, or capsules comprising a plurality of mini-tablets is more reliable and cost-effective than methods of manufacturing other particulate-based solid dosage forms. In certain embodiments, the active agent is a polyphenol or an aminosterol. In a particular embodiment, the active agent is EGCG. In a particular embodiment, the active agent is an aminosterol.

A mini-tablet may be made by compression or molding, optionally with one or more accessory ingredients. Compressed tablets may be prepared using binder (for example, gelatin or hydroxypropyl cellulose, or hydroxypropyl methyl cellulose), lubricant, inert diluent, preservative, surface-active or dispersing agent. Molded tablets may be made by molding in a suitable machine a mixture of the powdered compound moistened with an inert liquid diluent.

In some embodiments, the dispersing agents include, but are not limited to, copolymer systems such as polyethylene glycol-polylactic acid (PEG-PLA), polyethylene glycol-polyhydroxybutyric acid (PEG-PHB), polyvinylpyrrolidone-polyvinylalcohol (PVP-PVA), and derivatized copolymers such as copolymers of N-vinyl purine (or pyrimidine) derivatives and N-vinylpyrrolidone.

The solid dosage forms of the pharmaceutical compositions of the invention may optionally be scored or prepared with coatings and shells, such as enteric coatings and other coatings. They may also be formulated so as to provide slow or sustained release of the active ingredients therein using, for example, ethyl cellulose, hydroxypropyl cellulose, hydroxypropyl methyl cellulose, and combinations thereof, in varying proportions to provide the desired release profile, other polymer matrices. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredients only in a certain portion of the gastrointestinal tract, optionally, in a delayed manner. Examples of embedding compositions which can be used include polymeric substances.

The term "administer," "administering," or "administration" refers to implanting, absorbing, ingesting, or otherwise introducing a dosage form as described herein, or a composition thereof, in a subject. In certain embodiments, administration is oral administration. In certain embodiments, administration is rectal administration.

The phrases "systemic administration," "administered systemically," "peripheral administration" and "administered peripherally" as used herein mean the administration of a compound, or other material other than directly into the central nervous system, such that it enters the subject's system and, thus, is subject to metabolism and other like processes.

Actual dosage levels of active agent in the pharmaceutical compositions of this invention may be varied so as to obtain an amount of an active ingredient which is effective to achieve the desired therapeutic response for a particular subject, composition, and mode of administration, without being toxic to the subject.

The selected dosage level will depend upon a variety of factors including the activity of the active agent, the route of administration, the time of administration, the rate of excretion or metabolism of the particular compound being employed, the rate and extent of absorption, the duration of the treatment, other compounds and/or materials used in combination with the particular compound employed, the age, sex, weight, condition, general health and prior medical history of the subject being treated, and like factors well known in the medical arts.

A physician or veterinarian having ordinary skill in the art can readily determine and prescribe the effective amount of the pharmaceutical composition required. For example, the physician or veterinarian could start doses of the active agent employed in the pharmaceutical composition at levels lower than that required in order to achieve the desired therapeutic effect and gradually increase the dosage until the desired effect is achieved.

The term "treatment" is intended to encompass also prophylaxis, therapy and cure. The subject receiving this treatment is any animal in need, including primates, in particular humans, and other mammals such as equines, cattle, swine and sheep; and poultry and pets in general.

"Hydrophilic polymers" includes "water swelling polymers". In certain embodiments, hydrophilic and water swelling polymers suitable for use in the invention (e.g., in the dosage forms described herein) as release rate controlling polymers are readily water-soluble and are tolerated in vivo without toxic effects (i.e., are biocompatible). Suitable polymers include hydroxypropyl cellulose, hydroxypropyl methylcellulose (HPMC), polyethylene glycol (PEG), polylactic (also termed polylactide), polyglycolic acid (also termed polyglycolide), a polylactic-polyglycolic acid copolymer, and polyvinyl alcohol. In certain embodiments, the polymers are those having a molecular weight of at least about 5,000 daltons, at least about 25,000 daltons, at least about 50,000 daltons, at least about 100,000 daltons, at least about 250,000 daltons, at least about 500,000 daltons, or at least about 750,000 daltons. In some embodiments, the polymers are those having a molecular weight of less than or equal to about 1,000,000 daltons, less than or equal to about 750,000 daltons, less than or equal to about 500,000 daltons, less than or equal to about 250,000 daltons, less than or equal to about 100,000 daltons, less than or equal to about 50,000 daltons, or less than or equal to about 25,000 daltons. Combinations of these ranges are also possible (e.g., about 5,000 to about 1,000,000 daltons).

In certain embodiments, the hydrophilic polymer is polyethylene glycol (PEG) having a molecular weight of about 5,000 to 50,000 daltons, or having a molecular weight of about 25,000 to 250,000 daltons. Polymers may also be defined by the number of monomers therein; in certain embodiments of the invention utilizes polymers of at least about 3 monomers, at least about 10 monomers, at least about 25 monomers, at least about 50 monomers, at least about 100 monomers, or at least about 500 monomers. In some embodiments, the polymer has less than or equal to about 5,000 monomers, less than or equal to about 1,000 monomers, less than or equal to about 500 monomers, less than or equal to about 100 monomers, or less than or equal to about 50 monomers. Combinations of these ranges are also possible (e.g., 500 to 5,000 monomers).

In certain embodiments, other hydrophilic polymers which may be suitable for use in the invention (e.g., in the dosage forms described herein) include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethyl cellulose.

In certain embodiments, a dosage form described herein comprises a biocompatible polymer selected from polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly (ortho)esters, poly(butyric acid), poly(valeric acid), poly (lactide-co-caprolactone), polysaccharides, proteins, polyhyaluronic acids, polycyanoacrylates, and blends, mixtures, or copolymers thereof.

In certain embodiments, the release characteristics of a dosage form as described herein depend on the encapsulating material, the concentration of encapsulated compound (e.g., the active agent), and the presence of release modifiers. For example, release rate can be manipulated to be pH dependent, for example, using a pH sensitive coating that releases only at a low pH, as in the stomach, or a higher pH, as in the intestine. In certain embodiments, a pH sensitive coating releases preferably in the ileocecal region. In certain embodiments, release rate can be manipulated by utilizing coatings which are digested by bacterial enzymes such as amylose, pectin or the like. An enteric coating can be used to prevent release from occurring until after passage through the stomach. Multiple coatings or encapsulation in different materials can be used to obtain an initial release in the stomach, followed by later release in the intestine, or later in the colon. In some embodiments, the multiple coatings or encapsulation provide release in or near the colon. Release can also be manipulated by inclusion of salts or release rate controlling polymers, which can increase water uptake or release of compound by diffusion from the capsule. Excipients that modify the solubility of the compound can also be used to control the release rate. Agents which enhance stability or release of the active agent can also be incorporated. They can be added to the compound, added as a separate phase (i.e., as particulates). In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Release rate controlling polymers which add microstructure to the matrices (i.e., water soluble compounds, such as inorganic salts and sugars) are added as particulates.

In some embodiments, the polymers can be selected from any number of pharmaceutically acceptable polymers, including but not limited to, the celluloses (e.g., carboxymethylcelluloses, methylcelluloses, hydroxypropyl celluloses, hydroxypropyl methylcelluloses); hyaluronates; alginates; polysaccharides, heteropolysaccharides (pectins); poloxamers; poloxamines; ethylene vinyl acetates; polyethylene glycols; dextrans; polyvinylpyrrolidones; chitosans; polyvinylalcohols; propylene glycols; polyvinylacetates; phosphatidylcholines (lecithins); miglyols; polylactic acid; polyhydroxybutyric acid; mixtures thereof, copolymers thereof, derivatives thereof, and the like.

In certain embodiments, pH sensitive coatings include, but are no way limited to, cellulose acetate phthalates and other phthalates. Examples include, but are in no way limited to, polyvinyl acetate phthalate, methacrylates, and Eudragit® (EUDRAGUARD® control, Eudragit® NE 30 D). polymers. Alternatively, the controlled-release portion provides controlled-release to the small intestine and/or colon by the provision of pH sensitive methacrylate coatings, pH sensitive polymeric microspheres, or polymers which undergo degradation by hydrolysis. The controlled-release composition can be formulated with hydrophobic or gelling excipients or coatings. Colonic delivery can further be provided by coatings which are digested by bacterial enzymes such as amylose or pectin, by pH-dependent polymers, by hydrogel plugs swelling with time (Pulsincap), by time dependent hydrogel coatings and/or by acrylic acid linked to azoaromatic bonds coatings.

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups, such as cyanoacrylates and methacrylates).

A solid dosage form described herein may be a sustained-release dosage form or a controlled-release dosage form. These formulations, at comparable daily dosages of conventional immediate release compounds, are often associated with a lower incidence or severity of adverse reactions; and they can also be administered at a lower daily dose than conventional oral medication while maintaining therapeutic activity.

In certain embodiments, sustained-release formulations are designed to release initially an amount of compound (active ingredient) that promptly produces the desired therapeutic effect, and gradually and continually release other amounts of compound to maintain this level of therapeutic or prophylactic effect over an extended period of time. In order to maintain this constant level of compound in the body, the compound must be released from the dosage form at a rate that will replace the amount of compound being metabolized and excreted from the body. Sustained-release of an active ingredient can be stimulated by various conditions including, but not limited to, pH, temperature, enzymes, water, or other physiological conditions or compounds The term "sustained-release" is defined for purposes of the present disclosure as the release of the active agent from the formulation at such a rate that the target environment or organ (e.g., blood, plasma, gastrointestinal epithelium or lumen, small intestinal epithelium or lumen, large intestinal epithelium or lumen, colonic epithelium or lumen, large intestine, colon, etc.) concentrations (levels) are maintained within the therapeutic range (above the minimum effective concentration or "MEG") but below toxic levels over a period of time of about 12 hours or longer. In a particular embodiment, the period of time is about 24 hours or longer. In another particular embodiment, the period of time is about 48 hours or longer. In another particular embodiment, the period of time is about 60 hours or longer. In another particular embodiment, the period of time is about 72 hours or longer. In another particular embodiment, the period of time is about 84 hours or longer. In another particular embodiment, the period of time is about 96 hours or longer.

The solid particulates may be film coated with a material that permits release of the active agents at a delayed, controlled or sustained rate in an aqueous medium. The film coat is chosen so as to achieve, in combination with the other stated properties, a desired in vitro release rate. The sustained-release or controlled-release coating formulations of the invention should be capable of producing a strong, continuous film that is smooth and elegant, capable of supporting pigments and other coating additives, non-toxic, inert, and tack-free.

Suitable optional excipients for use in solid particulate cores include any commonly used excipients in pharmaceutics and are selected on the basis of compatibility with the active pharmaceutical agent and the release profile properties of the desired dosage form. Excipients include, but are not limited to, binders, fillers, flow aids, lubricants, gelling agents, plasticizers, stabilizers, surfactants, and the like. A summary of excipients described herein, may be found, for example in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference in their entirety.

Binders impart cohesive qualities and include, e.g., alginic acid and salts thereof; cellulose derivatives such as carboxymethylcellulose, methylcellulose (e.g., Methocel®), hydroxypropyl methylcellulose, hydroxyethyl cellulose, hydroxypropyl cellulose (e.g., Klucel®), ethyl cellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth; dextrin; a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabinogalactan, Veegum®, polyethylene glycol, waxes, sodium alginate, and the like.

Fillers or diluents increase bulk and act as dry binders to facilitate compression of the solid particulate cores. Such compounds include e.g., lactose; starch; mannitol; sorbitol; dextrose; microcrystalline cellulose such as Avicel®; dibasic calcium phosphate; dicalcium phosphate dihydrate; tricalcium phosphate; calcium phosphate; anhydrous lactose; spray-dried lactose; pregelatinized starch; compressible sugar, such as Di-Pac® (Amstar); hydroxypropyl methylcellulose; sucrose-based diluents; confectioner's sugar; monobasic calcium sulfate monohydrate; calcium sulfate dihydrate; calcium lactate trihydrate; dextrates; hydrolyzed cereal solids; amylose; powdered cellulose; calcium carbonate; glycine; kaolin; sodium chloride; inositol; bentonite; and the like.

Flow-aids or glidants improve the flow characteristics of a powder mixtures. Such compounds include, e.g., colloidal silicon dioxide such as Cab-o-sil®; tribasic calcium phosphate, talc, corn starch, DL-leucine, sodium lauryl sulfate, magnesium stearate, calcium stearate, sodium stearate, kaolin, and micronized amorphous silicon dioxide (Syloid®) and the like.

Lubricants are compounds which prevent, reduce or inhibit adhesion or friction of materials. Exemplary lubricants include, e.g., stearic acid; calcium hydroxide, talc; a hydrocarbon such as mineral oil, or hydrogenated vegetable oil such as hydrogenated soybean oil (Sterotex®), Lubritab®, Cutina®; higher fatty acids and their alkali-metal and alkaline earth metal salts, such as aluminum, calcium, magnesium, zinc, stearic acid, sodium stearates, magnesium stearate, glycerol, talc, waxes, Stearowet®, boric acid, sodium acetate, leucine, a polyethylene glycol or a methoxy-polyethylene glycol such as Carbowax™, sodium oleate, glyceryl behenate (Compitrol 888®), glyceryl palmitostearate (Precirol®), colloidal silica such as Syloid™, Cab-O-Sil®, a starch such as corn starch, silicone oil, a surfactant, and the like. Hydrophilic lubricants include, e.g., sodium stearyl fumarate (currently marketed under the trade name PRUV®), polyethylene glycol (PEG), magnesium lauryl sulfate, sodium lauryl sulfate (SLS), sodium benzoate, sodium chloride, and the like.

Gelling agents include compounds such as polyvinylpyrrolidone, e.g., polyvinylpyrrolidone K12, polyvinylpyrrolidone K17, polyvinylpyrrolidone K25, or polyvinylpyrrolidone K30; polyethylene glycol, e.g., the polyethylene glycol can have a molecular weight of about 300 to about 6000, or about 3350 to about 4000, or about 7000 to about 5400; polysorbate-80; sodium alginate; gums, such as, e.g., gum tragacanth, locust bean gum, gum acacia, carrageenan gum, guar gum; xanthans, including xanthan gum; sugars; cellulosics, such as, e.g., sodium carboxymethylcellulose, ethyl cellulose, methylcellulose, sodium carboxymethylcellulose, hydroxypropyl methylcellulose, hydroxypropyl cellulose, hydroxyethyl cellulose; polysorbate-80; sodium alginate; polyethoxylated sorbitan monolaurate; polyethoxylated sorbitan monolaurate; povidone and the like.

Stabilizers include compounds such as any anti-oxidation agents, e.g., butylated hydroxytoluene (BHT), sodium ascorbate, and tocopherol; buffers, acids, and the like.

Surfactants include compounds such as sodium lauryl sulfate, sorbitan monooleate, polyoxyethylene sorbitan monooleate, polysorbates, poloxamers, bile salts, glyceryl monostearate, copolymers of ethylene oxide and propylene oxide, e.g., Pluronic® (BASF); and the like.

The aforementioned excipients are given as examples only and are not meant to include all possible choices. Other suitable excipient classes include coloring agents, granulating agents, preservatives, anti-foaming agents, plasticizers and the like. Additionally, many excipients can have more than one role or function, or can be classified in more than one group; the classifications are descriptive only, and are not intended to limit any use of a particular excipient.

Coating layers, as used herein, refers to partially or completely encasing or coating a solid particulate core with a pharmaceutically acceptable coating. In addition, coating layers also refer to completely encasing or coating a unit dosage form such as a tablet or capsule that contain or encapsulate coated solid particulates. Second coats or undercoats, first coats or topcoats, inner- and outer-coats are various types of coating layers. Coating layers may also comprise additional, multiple layers such as third coats, fourth coats, fifth coats, sixth coats and the like.

The process of applying coating, layers can be achieved by any known method such as by using fluidized bed equipment, perforated pans, a regular pharmaceutical pan, compression coating, continuous or short spray methods, high-shear mixing or by drenching. For example, a plasticized dispersion of coating polymer may be applied onto a solid particulate core comprising an active pharmaceutical agent by spraying using any suitable spray equipment known in the art. Results of a coating procedure may be routinely checked by withdrawing a sample of the coated solid particulates and determining a release rate of the samples, or by measuring the coating thickness. If the desired amount of release is not achieved, the coating procedure may be repeated until the desired result is obtained. Detailed information concerning materials, equipment and processes for preparing coated dosage forms may be found in Pharmaceutical Dosage Forms: Tablets, eds. Lieberman et al. (New York: Marcel Dekker, Inc., 1989), and in Ansel et al., Pharmaceutical Dosage Forms and Drug Delivery Systems, $6^{th}$ Ed. (Media, Pa.: Williams & Wilkins, 1995; both incorporated herein by reference).

Coating layers can optionally contain a plasticizer to facilitate coalescing of applied polymer and control the formation of pores and cracks that would permit the penetration of the gastric fluids. Suitable plasticizers include, but are not limited to, triethyl citrate, triacetin (glyceryl triacetate), acetyl triethyl citrate, polyethylene glycols such as PEG 300, PEG 400, PEG 600, PEG 1450, PEG 3350, and PEG 800, Carbowax 400 (polyethylene glycol 400), diethyl phthalate, tributyl citrate, stearic acid, oleic acid, acetylated monoglycerides, glycerol, fatty acid esters, propylene glycol, and dibutyl phthalate. Coating layers can also contain other coating excipients such as anti-tacking agents such as talc or colloidal silicon dioxide, to prevent sticking, detackifiers, antifoaming agents, lubricants (e.g., magnesium stearate), and stabilizers (e.g., hydroxypropyl cellulose, acids and bases) to solubilize or disperse the coating material, and to improve coating performance of the coated solid particulate.

In certain embodiments, the dosage forms of the invention may optionally be coated with one or more materials suitable for the regulation of release or for the protection of the formulation. In one embodiment, coatings are provided to permit either pH-dependent or pH-independent release, e.g., when exposed to gastrointestinal fluid. A pH-dependent coating serves to release any of the active agent(s) in the desired areas of the gastrointestinal (GI) tract, e.g., the stomach or small intestine, such that an absorption profile is provided which is capable of providing therapeutic benefit to a subject. When a pH-independent coating is desired, the coating is designed to achieve optimal release regardless of pH-changes in the environmental fluid, e.g., the GI tract. It is also possible to formulate compositions which release a portion of the dose in one desired area of the GI tract, e.g., the stomach, and release the remainder of the dose in another area of the GI tract, e.g., the colon.

In certain embodiments, the substrate (e.g., solid particulate core) containing one or more active agent(s) is coated with a hydrophobic material selected from the group consisting of (i) an alkyl cellulose; (ii) an acrylic polymer; (iii) a water insoluble polymer, and (iv) mixtures thereof. The coating may be applied in the form of an organic or aqueous solution or dispersion. The coating may be applied to obtain a weight gain from about 1 to about 25% of the substrate in order to obtain a desired sustained release profile or controlled-release profile. Such formulations are described, e.g., in detail in U.S. Pat. Nos. 5,273,760 and 5,286,493; both incorporated by reference. Other examples of controlled- and sustained-release formulations and coatings which may be used in accordance with the invention include U.S. Pat. Nos. 5,324,351; 5,356,467, and 5,472,712; all incorporated by reference. Cellulosic materials and polymers, including alkyl celluloses, provide hydrophobic materials well suited for coating the formulations according to the invention. Simply by way of example, one alkyl cellulosic polymer is ethyl cellulose, although the artisan will appreciate that other cellulose or alkyl cellulose polymers may be readily employed, singly or in any combination, as all or part of a hydrophobic coating.

In embodiments of the invention where the coating comprises a hydrophobic material, such as ethyl cellulose, the inclusion of an effective amount of a plasticizer in an aqueous or solvent-based dispersion of hydrophobic material will further improve the physical properties of the coating. Exemplary solvents in which the plasticizer can be dispersed include, but are not limited to, alcohol-based solvents, such as methyl alcohol, ethyl alcohol, n-propyl alcohol, and iso-propyl alcohol. For example, because ethyl cellulose has a relatively high glass transition temperature and does not form flexible films under normal coating conditions, a plasticizer may be incorporated into an ethyl cellulose coating mixture before using the same as a coating material. Generally, the amount of plasticizer included in a coating solution is based on the concentration of the film-former, e.g., most often from about 1 to about 50 percent by weight of the coating mixture. Concentration of the plasticizer, however, can only be properly determined after careful experimentation with the particular coating mixture and method of application.

Examples of suitable plasticizers for ethyl cellulose include water insoluble plasticizers, such as dibutyl sebacate, diethyl phthalate, triethyl citrate, tributyl citrate, and triacetin, although it is possible that other water-insoluble plasticizers (such as acetylated monoglycerides, phthalate esters, castor oil) may be used. Triethyl citrate can be a plasticizer for mixtures of ethyl cellulose and release rate controlling polymers according to embodiments described herein.

In certain embodiments, a mixture of ethyl cellulose, a rate release controlling polymer, and a plasticizer is used to coat the solid particulates of the invention. In certain embodiments, a plurality of the coated solid particulates is thereafter placed in a gelatin capsule in an amount sufficient to provide an effective sustained release dose when ingested and contacted by an environmental fluid, e.g., gastric fluid or dissolution media. In certain embodiments, the plasticizer is triethyl citrate.

In some embodiments, the sustained-release solid dosage form is a capsule comprising 4 mm diameter mini-tablets, and the capsule comprises from 1 to 30 mini-tablets, from 1 to 20 mini-tablets, from 1 to 10 mini-tablets, from 1 to 5 mini-tablets, from 2 to 10 mini-tablets, from 2 to 5 mini-tablets, from 3 to 10 mini-tablets, from 3 to 5 mini-tablets, from 4 to 10 mini-tablets, or from 4 to 5 mini-tablets. In certain embodiments, the capsule comprises 30 mini-tablets, 25 mini-tablets, 20 mini-tablets, 15 mini-tablets, 10 mini-tablets, 9 mini-tablets, 8 mini-tablets, 7 mini-tablets, 6 mini-tablets, 5 mini-tablets, 4 mini-tablets, 3 mini-tablets, 2 mini-tablets, or 1 mini-tablet.

In certain embodiments, the capsule comprising 4 mm diameter mini-tablets comprises from 30 to 100 mini-tablets, from 32 to 70 mini-tablets, from 32 to 68 mini-tablets, from 32 to 64 mini-tablets, from 50 to 100 mini-tablets, from 60 to 100 mini-tablets, or from 70 to 100 mini-tablets. In certain embodiments, the capsule comprises 32 mini-tablets, 40 mini-tablets, 45 mini-tablets, 50 mini-tablets, 55 mini-tablets, 60 mini-tablets, 61 mini-tablets, 62 mini-tablets, 63 mini-tablets, 64 mini-tablets, 65 mini-tablets, 66 mini-tablets, 67 mini-tablets, 68 mini-tablets, 69 mini-tablets, 70 mini-tablets, 71 mini-tablets, 72 mini-tablets, 73 mini-tablets, 74 mini-tablets, 75 mini-tablets, 76 mini-tablets, 77 mini-tablets, 78 mini-tablets, 79 mini-tablets, 80 mini-tablets, 81 mini-tablets, 82 mini-tablets, 83 mini-tablets, 84 mini-tablets, 85 mini-tablets, 86 mini-tablets, 87 mini-tablets, 88 mini-tablets, 89 mini-tablets, 90 mini-tablets, 91 mini-tablets, 92 mini-tablets, 93 mini-tablets, 94 mini-tablets, 95 mini-tablets, 96 mini-tablets, 97 mini-tablets, 98 mini-tablets, 99 mini-tablets, or 100 mini-tablets.

In some embodiments, the sustained-release solid dosage form is a capsule comprising 1 mm diameter mini-tablets, and the capsule comprises from 50 to 1300 mini-tablets, from 50 to 250 mini-tablets, from 250 to 500 mini-tablets, from 500 to 750 mini-tablets, from 500 to 1000 mini-tablets, from 750 to 1000 mini-tablets, or from 1000 to 1300 mini-tablets. In certain embodiments, the capsule comprises about 250 mini-tablets, about 500 mini-tablets, about 750 mini-tablets, about 1000 mini-tablets, or about 1300 mini-tablets.

In some embodiments, the sustained-release solid dose forms comprise a plurality of mini-tablets, wherein each mini-tablet comprises from about 2 mg to about 10 mg, about 3 mg to about 10 mg, about 3.5 mg to about 10 mg, about 4.5 mg to about 10 mg, about 5.5 mg to about 10 mg, about 3.5 mg to about 9 mg, or about 3.5 mg to about 8 mg of active agent. In some embodiments, each mini-tablet comprises about 2 mg, about 2.5 mg, about 3 mg, about 3.5 mg, about 3.6 mg, about 3.7 mg, about 3.8 mg, about 3.9 mg, about 4 mg, about 4.25 mg, about 4.5 mg, about 4.75 mg, about 5 mg, about 5.25 mg, about 5.5 mg, about 5.75 mg, about 6 mg, about 6.25 mg, about 6.5 mg, about 6.75 mg, about 7 mg, about 7.25 mg, about 7.5 mg, about 7.75 mg, about 7.8 mg, about 8 mg, about 8.25 mg, about 8.5 mg, about 8.75 mg, about 9 mg, about 9.25 mg, about 9.5 mg, about 9.75 mg, or about 10 mg of active agent. In some embodiments, each mini-tablet comprises about 7.8 mg of active agent. In certain embodiments, the active agent is a polyphenol or an aminosterol. In a particular embodiment, the active agent is EGCG. In a particular embodiment, the active agent is an aminosterol.

In some embodiments, the sustained-release solid dosage form is a capsule comprising a plurality of solid particulates selected from beads, granules, or pellets, wherein the capsule comprises from about 6000 to about 60,000 solid particulates, from about 6000 to about 8000 solid particulates, from about 8000 to about 10,000 solid particulates, from about 8,000 to about 20,000 solid particulates, from about 10,000 to about 30,000 solid particulates, from about 20,000 to about 30,000 solid particulates, from about 20,000 to about 40,000 solid particulates, from about 30,000 to about 40,000 solid particulates, from about 40,000 to about 50,000 solid particulates, or from about 50,000 to about 60,000 solid particulates. In certain particular embodiments, the capsule comprises about 12,000, about 24,000, about 36,000, about 48,000, or about 60,000 solid particulates.

In some embodiments, the sustained-release solid dose forms comprise a plurality of solid particulates selected from beads, granules, or pellets, wherein each solid particulate comprises from about 0.1 mg to about 1 mg, about 0.1 mg to about 0.9 mg, about 0.1 mg to about 0.8 mg, about 0.1 mg to about 0.7 mg, about 0.1 mg to about 0.6 mg, about 0.1 mg to about 0.5 mg, about 0.1 mg to about 0.4 mg, about 0.1 mg to about 0.3 mg, or about 0.1 mg to about 0.2 mg of active agent. In certain embodiments, the active agent is a polyphenol or an aminosterol. In a particular embodiment, the active agent is EGCG. In a particular embodiment, the active agent is an aminosterol.

In some embodiments, a plurality of solid particulates (e.g., mini-tablets, beads, granules, or pellets) comprises a total amount of active agent of about 20 mg to about 100 mg, about 30 mg to about 100 mg, about 35 mg to about 100 mg, about 45 mg to about 100 mg, about 55 mg to about 100 mg, about 35 mg to about 90 mg, or about 35 mg to about 80 mg. In some embodiments, a plurality of mini-tablet comprise about 20 mg, about 25 mg, about 30 mg, about 35 mg, about 36 mg, about 37 mg, about 38 mg, about 39 mg, about 40 mg, about 42.5 mg, about 45 mg, about 47.5 mg, about 50 mg, about 52.5 mg, about 55 mg, about 57.5 mg, about 60 mg, about 62.5 mg, about 65 mg, about 67.5 mg, about 70 mg, about 72.5 mg, about 75 mg, about 77.5 mg, about 78 mg, about 80 mg, about 82.5 mg, about 85 mg, about 87.5 mg, about 90 mg, about 92.5 mg, about 95 mg, about 97.5 mg, or about 100 mg of active agent. In some embodiments, a plurality of mini-tablet comprise about 78 mg of active agent. In certain embodiments, the active agent is a polyphenol or an aminosterol. In a particular embodiment, the active agent is EGCG. In a particular embodiment, the active agent is an aminosterol. The sustained release solid dosage form of the invention slowly releases the active agent, for example, when ingested and exposed to gastric fluids, and then to intestinal fluids. The sustained release profile of the formulations of the invention can be altered, for example, by varying the amount of coating, by altering the manner in which the plasticizer is added to the coating mixture, by varying the amount of plasticizer relative to other coating components, by the inclusion of additional ingredients or excipients, by altering the method of manufacture or other process variables. The dissolution profile of the ultimate product may also be modified, for example, by increasing or decreasing the thickness of the coating.

The sustained release profile of the formulations of the invention can be altered, for example, by varying the amounts of and ratios between one or more hydrophilic polymers, such as hydroxypropyl methyl cellulose (HPMC) or hydroxypropyl cellulose, for example, and one or more hydrophobic polymers, such as ethyl cellulose, for example, that comprise the coating.

In certain embodiments, the coating mixtures of the invention may contain, in addition to the ethyl cellulose, the rate release controlling, and the plasticizer, a colorant to provide product distinction.

The coating may be applied onto the core comprising the one or more active agent by spraying using any suitable spray equipment known in the art. In certain embodiments, a Wurster fluidized-bed system is used in which an air jet, injected from underneath, fluidizes the coating material and effects drying while the coating is sprayed on.

In certain embodiments, the release of the active agent from the sustained release dosage form of the invention can be further influenced, i.e., adjusted to a desired rate, by the addition of one or more release-modifying agents, or by providing another passageway through the coating. The ratio of hydrophobic material to release rate controlling polymer is determined by, among other factors, the release rate required and the solubility characteristics of the materials selected.

The release-modifying agents, which function as release rate controlling polymers, include materials that can be dissolved, extracted or leached from the coating in the environment of use. The release rate controlling polymer may comprise one or more hydrophilic materials, such as hydroxypropyl methyl cellulose. In certain embodiments, the release-modifying agent is selected from the group consisting of hydroxypropyl methyl cellulose, lactose, metal stearates, and mixtures of any of the foregoing. The release-modifying agent may also comprise a semi-permeable polymer.

The coatings of the dosage forms described herein can also include erosion-promoting agents, such as starch and gums. In certain embodiments, the coatings can also include materials useful for making microporous lamina in the environment of use, such as polycarbonates comprised of linear polyesters of carbonic acid in which carbonate groups reoccur in the polymer chain. In certain embodiments, the coatings of the invention may also include an exit means comprising at least one passageway, orifice, or the like. The passageway may be formed by such methods as those disclosed in U.S. Pat. Nos. 3,845,770; 3,916,889; 4,063,064; and 4,088,864; all incorporated by reference. The passageway can have any shape, such as round, triangular, square, elliptical, or irregular.

In certain embodiments, the sustained-release or controlled-release dosage forms described herein may slowly release the active agents, e.g., when ingested and exposed to gastric fluids, and then to intestinal fluids. The sustained release or controlled-release profile can be altered, for example, by varying the amount of retardant, i.e., hydrophobic material, by varying the amount of plasticizer relative to hydrophobic material, by the inclusion of additional ingredients or excipients, by altering the method of manufacture.

In one embodiment, the plurality of coated solid particulates is incorporated into a solid unit dosage form. The term "solid unit dosage form" means a dosage form intended to be swallowed as a single unit that is selected from a hard or soft capsule. In one embodiment, the solid unit dosage forms are selected from soft capsules or hard capsules of any size or shape. Suitable capsules include, but are not limited to, spherical or elliptical soft elastic gelatin capsules; starch, cellulose or gelatin hard capsules such as Capill®, and the like. Appropriate capsule sizes are selected based on the number and size of the coated mini-tablets to be incorporated and include capsule sizes 000, 00EL, 00, 0EL, 0, 1, 2, 3, 4 or 5. In some embodiments, a capsule comprises 4 mm diameter mini-tablets, and may contain from about 2 to 10 mini-tablets, from about 11 to 20 mini-tablets, from about 20 to 30 mini-tablets, from 30 to 100 mini-tablets, from 32 to 70 mini-tablets, from 32 to 68 mini-tablets, from 32 to about 64 mini-tablets, from about 50 to about 100 mini-tablets, from about 60 to about 100 mini-tablets, or from about 70 to about 100 mini-tablets. In certain embodiments, the gelatin capsule comprises 32 mini-tablets, 40 mini-tablets, 45 mini-tablets, 50 mini-tablets, 55 mini-tablets, 60 mini-tablets, 61 mini-tablets, 62 mini-tablets, 63 mini-tablets, 64 mini-tablets, 65 mini-tablets, 66 mini-tablets, 67 mini-tablets, 68 mini-tablets, 69 mini-tablets, 70 mini-tablets, 71 mini-tablets, 72 mini-tablets, 73 mini-tablets, 74 mini-tablets, 75 mini-tablets, 76 mini-tablets, 77 mini-tablets, 78 mini-tablets, 79 mini-tablets, 80 mini-tablets, 81 mini-tablets, 82 mini-tablets, 83 mini-tablets, 84 mini-tablets, 85 mini-tablets, 86 mini-tablets, 87 mini-tablets, 88 mini-tablets, 89 mini-tablets, 90 mini-tablets, 91 mini-tablets, 92 mini-tablets, 93 mini-tablets, 94 mini-tablets, 95 mini-tablets, 96 mini-tablets, 97 mini-tablets, 98 mini-tablets, 99 mini-tablets, or 100 mini-tablets. In some embodiments, a capsule comprises 1 mm diameter mini-tablets, and may contain from 50 to 1300 mini-tablets, from 50 to 250 mini-tablets, from 250 to 500 mini-tablets, from 500 to 750 mini-tablets, from 500 to 1000 mini-tablets, from 750 to 1000 mini-tablets, or from 1000 to 1300 mini-tablets. In certain embodiments, the capsule comprises about 250 mini-tablets, about 500 mini-tablets, about 750 mini-tablets, about 1000 mini-tablets, or about 1300 mini-tablets. In some embodiments, a capsule comprises solid particulates selected from beads, granules, or pellets, and may contain from about 6000 to about 60,000 solid particulates, from about 6000 to about 8000 solid particulates, from about 8000 to about 10,000 solid particulates, from about 8,000 to about 20,000 solid particulates, from about 10,000 to about 30,000 solid particulates, from about 20,000 to about 30,000 solid particulates, from about 20,000 to about 40,000 solid particulates, from about 30,000 to about 40,000 solid particulates, from about 40,000 to about 50,000 solid particulates, or from about 50,000 to about 60,000 solid particulates. In certain particular embodiments, the capsule comprises about 12,000, about 24,000, about 36,000, about 48,000, or about 60,000 solid particulates.

In some instances, a capsule containing coated solid particulates is itself further coated with a delayed release or enteric coating as described herein.

In some instances, the solid particulates themselves may further comprise an enteric coating, as described herein.

In some embodiments, one or more of the aforementioned sustained release dosage forms may be co-administered with one or more gastric motility testing systems, and the like. In some embodiments, the gastric motility testing system is The SmartPill™ Motility Capsule or the Medtronic SmartPill™ (see, e.g., Dig Dis Sci (2009) 54:2167-74), which measures pressure, pH, transit time and temperature as it passes through the entire gastrointestinal tract, providing diagnostic information including gastric emptying time, colonic transit time, whole gut transit times, pressure patterns, and the like in various parts of the gastrointestinal tract and/or colon.

One aspect of the invention relates to combination therapy. This type of therapy is advantageous because the co-administration of active ingredients achieves a therapeutic effect that is greater than the therapeutic effect achieved by administration of only a single therapeutic agent.

In certain embodiments, a subject suffering from an amyloid disorder, such as intestinal dysbiosis, intestinal hyperpermeability, irritable bowel syndrome (IBS), inflammatory bowel disease (IBD), ulcerative colitis or Crohn's disease, is administered a sustained release dosage form comprising an active agent as described herein in combination with an additional therapeutic agent in order to treat such amyloid disorders, or to prevent their recurrence. In some embodiments, the additional therapeutic agent comprises other dosage forms comprising epigallocatechin gallate (EGCG) or aminosterols, such as squalamine. Additional therapeutic agents comprising squalamine and their uses in the treatment of Parkinson's disease and gastrointestinal motility disorders are described in U.S. Pat. Nos. 10,040,817, 8,623,416, and U.S. Pat. Applications US 2017/0327530, US 2017/0326156, US 2018/0319837, and US 2018/0327445, all of which are hereby incorporated by reference in their entirety.

In certain embodiments, the active ingredient is EGCG. In certain embodiments, the active ingredient is squalamine. In certain embodiments, the active ingredient comprises a combination of a plurality of active ingredients selected from polyphenols (e.g., EGCG) and aminosterols.

In certain embodiments, the co-administration of two or more active agents achieves a therapeutic effect that is greater than the therapeutic effect achieved by administration of only a single therapeutic agent. In this regard, the combination therapies are efficacious. The therapeutic effect of one active agent is augmented by the co-administration of another active agent. In certain embodiments, the co-administration of two or more therapeutic agents achieves a synergistic effect, i.e., a therapeutic effect that is greater than the sum of the therapeutic effects of the individual components of the combination.

In certain embodiments, the co-administration of two or more active agents achieves a therapeutic effect that is equal to about the sum of the therapeutic effects achieved by administration of each single active agent. In these embodiments, the combination therapies are said to be "additive."

Active agents may be administered as separate compositions. One or more active agent may be administered at the same time as the other active agent(s) or the active agents may be administered intermittently. The length of time between administrations of the active agents may be adjusted to achieve the desired therapeutic effect. In certain instances, one or more active agent(s) may be administered only a few minutes (e.g., about 1, 2, 5, 10, 30, or 60 min) after administration of the other active agent(s). Alternatively, one or more active agent(s) may be administered several hours (e.g., about 2, 4, 6, 10, 12, 24, or 36 h) after administration of the other active agent(s). In certain embodiments, it may be advantageous to administer more than one dosage of one or more active agent(s) between administrations of the remaining active agent(s). For example, one active agent may be administered at 2 hours and then again at 10 hours following administration of the other active agent(s). Importantly, it is required that the therapeutic effects of each active agent overlap for at least a portion of the duration of each active agent so that the overall therapeutic effect of the combination therapy is attributable in part to the combined or synergistic effects of the combination therapy. Here it is contemplated that active agents include polyphenols and aminosterols, as described herein, and also additional therapeutic agents. Such additional therapeutic agents may be selected from caffeine, nicotine, theophylline, theobromine, xanthine, methylxanthine, or derivatives thereof; an inhibitor of α-synuclein aggregation; L-DOPA, carbidopa, Lodosyn, levodopa, Droxidopa, Northera, Rasagiline, apomorphine hydrochloride, Bromocriptine, Rotigotine, Pramipexole, Ropinirole, Benzotropine, Trihexyphenidyl, Selegiline, Entacapone, Tolcapone, Amantadine, Pimavanersin, Rivastigmine; or any combination thereof.

The dosage of the active agents will generally be dependent upon a number of factors including pharmacodynamic characteristics of each agent of the combination, mode and route of administration of active agent(s), the health of the subject being treated, the extent of treatment desired, the nature and kind of concurrent therapy, if any, and the frequency of treatment and the nature of the effect desired. In general, dosage ranges of the active agents often range from about 0.001 mg/kg to about 250 mg/kg body weight per day. For a normal adult having a body weight of about 70 kg, a dosage may range from about 0.1 mg/kg to about 25 mg/kg body weight. However, some variability in this general dosage range may be required depending upon the age and weight of the subject being treated, the intended route of administration, the particular agent being administered and the like. Since two or more different active agents are being used together in a combination therapy, the potency of each agent and the interactive effects achieved using them together must be considered. Importantly, the determination of dosage ranges and optimal dosages for a particular mammal is also well within the ability of one of ordinary skill in the art having the benefit of the instant disclosure.

In certain embodiments, it may be advantageous for a pharmaceutical combination to have a relatively large amount of the first component (e.g., first active agent) compared to the second component (e.g., second active agent). In certain instances, the ratio of the first active agent to second active agent is about 200:1, 190:1, 180:1, 170:1, 160:1, 150:1, 140:1, 130:1, 120:1, 110:1, 100:1, 90:1, 80:1, 70:1, 60:1, 50:1, 40:1, 30:1, 20:1, 15:1, 10:1, 9:1, 8:1, 7:1, 6:1, or 5:1. In certain embodiments, it may be preferable to have a more equal distribution of active agents. In certain instances, the ratio of the first active agent to the second active agent is about 4:1, 3:1, 2:1, 1:1, 1:2, 1:3, or 1:4. In certain embodiments, it may be advantageous for the pharmaceutical combination to have a relatively large amount of the second component (e.g., second active agent) compared to the first component (e.g., first active agent). In certain instances, the ratio of the second active agent to the first active agent is about 30:1, 20:1, 15:1, 10:1, 9:1, 8:1, 7:1, 6:1, or 5:1. In certain instances, the ratio of the second active agent to first active agent is about 100:1, 90:1, 80:1, 70:1, 60:1, 50:1, or 40:1. In certain instances, the ratio of the second active agent to first active agent is about 200:1, 190:1, 180:1, 170:1, 160:1, 150:1, 140:1, 130:1, 120:1, or 110:1.

Dosage amount and interval may be adjusted on an individual or group basis to provide plasma levels of a particular active moiety or moieties sufficient to maintain the modulating effects or minimal effective concentration (MEC) of each of them. The MEC will vary for each compound and individual, but it can be estimated from in vitro data. Dosages necessary to achieve the MEC will depend on individual characteristics and route of administration. However, HPLC assays or bioassays can be used to determine plasma concentrations.

The term "synergistic" refers to a combination which is more therapeutically effective than the additive effects of any two or more single agents. A synergistic effect permits the effective treatment of a disease using lower amounts (doses) than individual therapy. The lower doses result in lower toxicity without reduced efficacy. In addition, a synergistic effect can result in improved efficacy. Finally, synergy may result in an improved avoidance or reduction of disease as compared to any single therapy.

Combination therapy can allow for the product of lower doses of the first active or the second active agent (referred to as "apparent one-way synergy" herein), or lower doses of both active agents (referred to as "two-way synergy" herein) than would normally be required when either compound is used alone.

Combination therapy can allow for the product of lower doses of any one of the active agents (referred to as "apparent one-way synergy" herein), or lower doses of all active agents than would normally be required when any compound is used alone.

In certain embodiments, the synergism exhibited between one or more active agent(s) and the remaining active agent(s) is such that the dosage of one of the active agents would be sub-therapeutic if administered without the dosage of the other active agents.

The terms "augmentation" or "augment" refer to combinations where one of the compounds increases or enhances therapeutic effects of another compound or compounds administered to a subject. In some instances, augmentation can result in improving the efficacy, tolerability, or safety, or any combination thereof, of a particular therapy.

In certain embodiments, the invention relates to a pharmaceutical composition comprising a therapeutically effective dose of one or more active agent(s) together with a dose of another active agent effective to augment the therapeutic effect of the one or more therapeutic agent(s). In other embodiments, the invention relates to methods of augmenting the therapeutic effect in a subject of one or more active agent(s) by administering another active agent to the subject.

In certain embodiments, the present disclosure is directed in part to synergistic combinations of one or more therapeutic agent(s) in an amount sufficient to render a therapeutic effect together with the remaining therapeutic agent(s). For example, in certain embodiments a therapeutic effect is attained which is at least about 2 (or at least about 4, 6, 8, or 10) times greater than that obtained with the dose of the one or more therapeutic agent(s) alone. In certain embodiments, the synergistic combination provides a therapeutic effect which is up to about 20, 30 or 40 times greater than that obtained with the dose of the one or more therapeutic agent(s) alone. In such embodiments, the synergistic combinations display what is referred to herein as an "apparent one-way synergy", meaning that the dose of the remaining therapeutic agent(s) synergistically potentiates the effect of the one or more therapeutic agent(s), but the dose of the one or more therapeutic agent(s) does not appear to significantly potentiate the effect of the remaining therapeutic agent(s).

In certain embodiments, the combination of active agents exhibits two-way synergism, meaning that the second therapeutic agent potentiates the effect of the first therapeutic agent, and the first therapeutic agent potentiates the effect of the second therapeutic agent. Thus, other embodiments of the invention relate to combinations of a second therapeutic agent and a first therapeutic agent where the dose of each compound is reduced due to the synergism between the compounds, and the therapeutic effect derived from the combination of compounds in reduced doses is enhanced. The two-way synergism is not always readily apparent in actual dosages due to the potency ratio of the first therapeutic agent to the second therapeutic agent. For instance, two-way synergism can be difficult to detect when one therapeutic agent displays much greater therapeutic potency relative to the other therapeutic agent.

The synergistic effects of combination therapy may be evaluated by biological activity assays. For example, the therapeutic agents are mixed at molar ratios designed to give approximately equipotent therapeutic effects based on the EC90 values. Then, three different molar ratios are used for each combination to allow for variability in the estimates of relative potency. These molar ratios are maintained throughout the dilution series. The corresponding monotherapies are also evaluated in parallel to the combination treatments using the standard primary assay format. A comparison of the therapeutic effect of the combination treatment to the therapeutic effect of the monotherapy gives a measure of the synergistic effect. Further details on the design of combination analyses can be found in B E Korba (1996) Antiviral Res. 29:49. Analysis of synergism, additivity, or antagonism can be determined by analysis of the aforementioned data using the CalcuSyn™ program (Biosoft, Inc.). This program evaluates drug interactions by use of the widely accepted method of Chou and Talalay combined with a statistically evaluation using the Monte Carlo statistical package. The data are displayed in several different formats including median-effect and dose-effects plots, isobolograms, and combination index [CI] plots with standard deviations. For the latter analysis, a CI greater than 1.0 indicates antagonism and a CI less than 1.0 indicates synergism.

Compositions of the invention present the opportunity for obtaining relief from moderate to severe cases of disease. Due to the synergistic or additive or augmented effects provided by the inventive combination of the first and second therapeutic agent, it may be possible to use reduced dosages of each of therapeutic agent. Due to the synergistic or additive or augmented effects provided by the inventive combination of the first, second, and third therapeutic agents, it may be possible to use reduced dosages of each of therapeutic agent. By using lesser amounts of compounds, the side effects associated with each may be reduced in number and degree. Moreover, the inventive combinations avoid side effects to which some subjects are particularly sensitive.

In certain embodiments, the invention relates to a sustained-release solid dosage form, comprising a plurality of mini-tablets, wherein each mini-tablet comprises:
(a) a core, comprising an active agent; and
(b) a coating, ethyl cellulose; and an additional rate controlling polymer selected from the group consisting of hydroxypropyl cellulose and hydroxypropyl methyl cellulose (HPMC);
wherein the coating surrounds the core. In certain embodiments, the active agent is a polyphenol or an aminosterol. In a particular embodiment, the active agent is EGCG. In a particular embodiment, the active agent is an aminosterol.

In certain embodiments, the invention relates to any one of the aforementioned solid dosage forms, wherein the core further comprises a diluent.

In certain embodiments, the invention relates to any one of the aforementioned solid dosage forms, wherein the core further comprises a binder.

In certain embodiments, the invention relates to any one of the aforementioned solid dosage forms, wherein the core further comprises a lubricant.

In certain embodiments, the invention relates to any one of the aforementioned solid dosage forms, wherein the coating further comprises a plasticizer.

In certain embodiments, the invention relates to a sustained-release solid dosage form, comprising a plurality of mini-tablets, wherein each mini-tablet comprises:
(a) a core, comprising an active agent; a diluent; a binder; and a lubricant; and
(b) a coating, comprising ethyl cellulose; a plasticizer; and a release rate controlling polymer selected from the group consisting of hydroxypropyl cellulose and hydroxypropyl methyl cellulose (HPMC);
wherein the coating surrounds the core. In certain embodiments, the active agent is a polyphenol or an aminosterol. In a particular embodiment, the active agent is EGCG. In a particular embodiment, the active agent is an aminosterol.

In certain embodiments, the invention relates to a sustained-release solid dosage form, consisting essentially of a plurality of solid particulates (e.g., mini-tablets, beads, granules, or pellets) wherein each solid particulate comprises:
(a) a core, consisting essentially of an active agent; a diluent; a binder; and a lubricant; and
(b) a coating, consisting essentially of ethyl cellulose; a plasticizer; and a rate release controlling polymer selected from the group consisting of hydroxypropyl cellulose and hydroxypropyl methyl cellulose (HPMC);
wherein the coating surrounds the core. In certain embodiments, the active agent is a polyphenol or an aminosterol. In a particular embodiment, the active agent is EGCG. In a particular embodiment, the active agent is an aminosterol.

In certain embodiments, the invention relates to any one of the aforementioned solid dosage forms, wherein the plasticizer is triethyl citrate.

In certain embodiments, the invention relates to any one of the aforementioned solid dosage forms, wherein the diameter of each solid particulate is about 1 mm to about 5 mm.

In certain embodiments, the invention relates to any one of the aforementioned solid dosage forms, wherein the diameter of each solid particulate is about about 1 mm, about 1.5 mm, about 2.0 mm, about 2.5 mm, about 3.0 mm, about 3.5 mm, about 4.0 mm, about 4.5 mm, or about 5.0 mm. In a particular embodiment, the diameter of the solid particulate is about 1 mm. In a particular embodiment, the diameter of the solid particulate is about 4 mm.

In certain embodiments, the invention relates to any one of the aforementioned solid dosage forms, wherein the plurality of solid particulates all have substantially the same diameters.

In certain embodiments, the invention relates to any one of the aforementioned solid dosage forms, wherein the solid particulate is a 4 mm diameter mini-tablet, and wherein the number of mini-tablets in the dosage form is about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98 about 99, about 100 mini-tablets.

In certain embodiments, the number of 4 mm diameter mini-tablets is about 30 to about 100. In certain embodiments, the number of 4 mm diameter mini-tablets is about 50 to about 80.

In certain embodiments, the number of 4 mm diameter mini-tablets is about 60 to about 70.

In certain embodiments, the number of 4 mm diameter mini-tablets is about 64 to about 85.

In certain embodiments, the number of mini-tablets is about 80 to about 100.

In certain embodiments, the invention relates to any one of the aforementioned solid dosage forms, wherein the viscosity of any of the components is within a particular range. The viscosity of particular components can be measured using methods well known to those of ordinary skill in the art. For example, the viscosity of particular components can be measured using methods described in United States Pharmacopeia (USP) test number 911 for measuring viscosity.

In certain embodiments, the invention relates to any one of the aforementioned solid dosage forms, wherein the viscosity of the ethyl cellulose is about 1 cP to about 1,000,000 cP.

In certain embodiments, the invention relates to any one of the aforementioned solid dosage forms, wherein the viscosity of the ethyl cellulose is about 12 cP to about 1,000,000 cP.

In certain embodiments, the invention relates to any one of the aforementioned solid dosage forms, wherein the viscosity of the ethyl cellulose is about 20 cP to about 1,000,000 cP.

In certain embodiments, the invention relates to any one of the aforementioned solid dosage forms, wherein the viscosity of the ethyl cellulose is about 50 cP to about 1,000,000 cP.

In certain embodiments, the invention relates to any one of the aforementioned solid dosage forms, wherein the release rate controlling polymer is ethyl cellulose.

In certain embodiments, the invention relates to any one of the aforementioned solid dosage forms, wherein the release rate controlling polymer is hydroxypropyl cellulose.

In certain embodiments, the invention relates to any one of the aforementioned solid dosage forms, wherein the release rate controlling polymer is hydroxypropyl methyl cellulose (HPMC).

In certain embodiments, the invention relates to any one of the aforementioned solid dosage forms, wherein the release rate controlling polymer is polymethyl methacrylate (PMMA).

In certain embodiments, the invention relates to any one of the aforementioned solid dosage forms, wherein the viscosity of the hydroxypropyl cellulose or hydroxypropyl methyl cellulose (HPMC) is about 3 cP to about 1,000,000 cP.

In certain embodiments, the invention relates to any one of the aforementioned solid dosage forms, wherein the viscosity of the hydroxypropyl cellulose or hydroxypropyl methyl cellulose (HPMC) is about 1,000,000 cP.

In certain embodiments, the invention relates to any one of the aforementioned solid dosage forms, wherein the solid dosage form does not comprise an acrylic polymer.

In certain embodiments, the invention relates to any one of the aforementioned solid dosage forms, wherein the coating does not comprise an anionic polymer.

In certain embodiments, the invention relates to any one of the aforementioned solid dosage forms, wherein the core does not comprise a lipophilic material.

In certain embodiments, the invention relates to any one of the aforementioned solid dosage forms, wherein the core does not comprise polyvinylpyrrolidone.

In certain embodiments, the invention relates to any one of the aforementioned solid dosage forms, further comprising a diluent, wherein the diluent is selected from the group consisting of lactose; microcrystalline cellulose; starch; mannitol; sorbitol; dextrose; dibasic calcium phosphate; dicalcium phosphate dihydrate; tricalcium phosphate; calcium phosphate; anhydrous lactose; spray-dried lactose; pregelatinized starch; compressible sugar; hydroxypropyl methyl cellulose; sucrose-based diluents; confectioner's sugar; monobasic calcium sulfate monohydrate; calcium sulfate dihydrate; calcium lactate trihydrate; dextrates; hydrolyzed cereal solids; amylose; powdered cellulose; calcium carbonate; glycine; kaolin; sodium chloride; inositol; and bentonite.

In certain embodiments, the invention relates to any one of the aforementioned solid dosage forms, further comprising a diluent, wherein the diluent is selected from the group consisting of lactose; microcrystalline cellulose; starch; mannitol; sorbitol; dextrose; anhydrous lactose; spray-dried lactose; pregelatinized starch; compressible sugar; hydroxypropyl methyl cellulose; sucrose-based diluents; confectioner's sugar; calcium lactate trihydrate; dextrates; hydrolyzed cereal solids; amylose; powdered cellulose; and inositol.

In certain embodiments, the invention relates to any one of the aforementioned solid dosage forms, further comprising a diluent, wherein the diluent is selected from the group consisting of lactose; microcrystalline cellulose; dextrose; anhydrous lactose; spray-dried lactose; sucrose-based diluents; confectioner's sugar; and amylose.

In certain embodiments, the invention relates to any one of the aforementioned solid dosage forms, further comprising a diluent, wherein the diluent is lactose or microcrystalline cellulose. In certain embodiments, the solid dosage form comprises lactose. In certain embodiments, the solid dosage form comprises microcrystalline cellulose.

In certain embodiments, the invention relates to any one of the aforementioned solid dosage forms, further comprising a binder, wherein the binder is selected from the group consisting of alginic acid and salts thereof; cellulose derivatives such as carboxymethyl cellulose, methylcellulose, hydroxypropyl methyl cellulose, hydroxyethyl cellulose, hydroxypropyl cellulose, ethyl cellulose, and microcrystalline cellulose; microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth; dextrin; a sugar, such as sucrose, glucose, dextrose, molasses, mannitol, sorbitol, xylitol, and lactose; a natural or synthetic gum such as acacia, tragacanth, ghatti gum, mucilage of isapol husks, polyvinylpyrrolidone, larch arabinogalactan, polyethylene glycol, and sodium alginate.

In certain embodiments, the invention relates to any one of the aforementioned solid dosage forms, further comprising a binder, wherein the binder is selected from the group consisting of cellulose derivatives such as carboxymethyl cellulose, methyl cellulose, hydroxypropyl methyl cellulose, hydroxyethyl cellulose, hydroxypropyl cellulose, ethyl cellulose, and microcrystalline cellulose; microcrystalline dextrose; amylose; polysaccharide acids; starch; and dextrin.

In certain embodiments, the invention relates to any one of the aforementioned solid dosage forms, further comprising a binder, wherein the binder is selected from the group consisting of cellulose derivatives such as carboxymethylcellulose, methylcellulose, hydroxypropyl methylcellulose, hydroxyethyl cellulose, hydroxypropyl cellulose, ethyl cellulose, and microcrystalline cellulose.

In certain embodiments, the invention relates to any one of the aforementioned solid dosage forms, further comprising a binder, wherein the binder is hydroxypropyl cellulose.

In certain embodiments, the invention relates to any one of the aforementioned solid dosage forms, wherein the lubricant is selected from the group consisting of stearic acid; calcium hydroxide; talc; mineral oil; hydrogenated vegetable oil, such as hydrogenated soybean oil; higher fatty acids and their alkali-metal and alkaline earth metal salts, such as aluminum, sodium, calcium, magnesium, or zinc stearates; glycerol; boric acid; sodium acetate; leucine; polyethylene glycol or methoxypolyethylene glycol; sodium oleate; glyceryl behenate; glyceryl palmitostearate; colloidal silica; a starch, such as corn starch; silicone oil; sodium stearyl fumarate; surfactants; magnesium lauryl sulfate; sodium lauryl sulfate; sodium benzoate; and sodium chloride.

In certain embodiments, the invention relates to any one of the aforementioned solid dosage forms, wherein the lubricant is selected from the group consisting of stearic acid; higher fatty acids and their alkali-metal and alkaline earth metal salts, such as aluminum, sodium, calcium, magnesium, or zinc stearates; sodium oleate; sodium stearyl fumarate; magnesium lauryl sulfate; and sodium lauryl sulfate.

In certain embodiments, the invention relates to any one of the aforementioned solid dosage forms, wherein the lubricant is selected from the group consisting of stearic acid; higher fatty acids and their alkali-metal and alkaline earth metal salts, such as aluminum, sodium, calcium, magnesium, or zinc stearates.

In certain embodiments, the invention relates to any one of the aforementioned solid dosage forms, wherein the lubricant is magnesium stearate.

In certain embodiments, the invention relates to any one of the aforementioned solid dosage forms, wherein the weight percentage of the active agent is about 40% to about 95% based on the weight of the core. In certain embodiments, the invention relates to any one of the aforementioned solid dosage forms, wherein the weight percentage of the active agent is about 75% to about 85% based on the weight of the core. In certain embodiments, the invention relates to any one of the aforementioned solid dosage forms, wherein the weight percentage of the active agent is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79% about 80%, about 81%, about 82%, about 83%, about 84%, about 85%, about 86%, about 87%, about 88%, about 89%, about 90%, about 91%, about 92%, about 93%, about 94%, or about 95% based on the weight of the core. In certain embodiments, the active agent is a polyphenol or an aminosterol. In a particular embodiment, the active agent is EGCG. In a particular embodiment, the active agent is an aminosterol.

In certain embodiments, the invention relates to any one of the aforementioned solid dosage forms, wherein the weight percentage of the active agent is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79% about 80%, about 81%, about 82%, about 83%, about 84%, about 85%, about 86%, about 87%, about 88%, about 89%, about 90%, about 91%, about 92%, about 93%, about 94% or about 95% based on the weight of the mini-tablet. In certain embodiments, the active agent is a polyphenol or an aminosterol. In a particular embodiment, the active agent is EGCG. In a particular embodiment, the active agent is an aminosterol.

In certain embodiments, the invention relates to any one of the aforementioned solid dosage forms, wherein the weight percentage of the active agent is about 80% based on the weight of the core. In certain embodiments, the active agent is a polyphenol or an aminosterol. In a particular embodiment, the active agent is EGCG. In a particular embodiment, the active agent is an aminosterol.

In certain embodiments, the invention relates to any one of the aforementioned solid dosage forms, wherein the weight percentage of the active agent is about 40% to about 90% by weight of the solid particulate. In certain embodiments, the active agent is a polyphenol or an aminosterol. In a particular embodiment, the active agent is EGCG. In a particular embodiment, the active agent is an aminosterol.

In certain embodiments, the invention relates to any one of the aforementioned solid dosage forms, wherein the weight percentage of the active agent is about 40%, about 45%, about 50%, about 55%, about 60%, about 65%, about 70%, about 75%, about 80%, about 85%, about 90%, or about 95% by weight of the solid particulate. In certain embodiments, the active agent is a polyphenol or an aminosterol. In a particular embodiment, the active agent is EGCG. In a particular embodiment, the active agent is an aminosterol.

In certain embodiments, the invention relates to any one of the aforementioned solid dosage forms, wherein the weight percentage of the active agent is about 40%, about 45%, about 50%, about 55%, about 60%, about 65%, about 70%, about 75%, about 80%, about 85%, about 90%, or about 95% by weight of the core. In certain embodiments, the active agent is a polyphenol or an aminosterol. In a particular embodiment, the active agent is EGCG. In a particular embodiment, the active agent is an aminosterol.

In certain embodiments, the invention relates to any one of the aforementioned solid dosage forms, further comprising a diluent, wherein the weight percentage of the diluent is about 10% to about 40% based on the weight of the core.

In certain embodiments, the invention relates to any one of the aforementioned solid dosage forms, further comprising a diluent, wherein the weight percentage of the diluent is about 10% to about 25% based on the weight of the core.

In certain embodiments, the invention relates to any one of the aforementioned solid dosage forms, further comprising a diluent, wherein the weight percentage of the diluent is about 10% to about 20% based on the weight of the core.

In certain embodiments, the invention relates to any one of the aforementioned solid dosage forms, further comprising a diluent, wherein the weight percentage of the diluent is about 10%, about 11%, about 12%, about 13%, about 14%, about 15%, about 16%, about 17%, about 18%, about 19%, or about 20% based on the weight of the core.

In certain embodiments, the invention relates to any one of the aforementioned solid dosage forms, further comprising a binder, wherein the weight percentage of the binder is about 1% to about 10% based on the weight of the core.

In certain embodiments, the invention relates to any one of the aforementioned solid dosage forms, further comprising a binder, wherein the weight percentage of the binder is about 1% to about 5% based on the weight of the core.

In certain embodiments, the invention relates to any one of the aforementioned solid dosage forms, further comprising a binder, wherein the weight percentage of the binder is about 1%, about 2%, about 3%, about 4%, or about 5% based on the weight of the core.

In certain embodiments, the invention relates to any one of the aforementioned solid dosage forms, further comprising a lubricant, wherein the weight percentage of the lubricant is about 0.5% to about 5% based on the weight of the core.

In certain embodiments, the invention relates to any one of the aforementioned solid dosage forms, further comprising a lubricant, wherein the weight percentage of the lubricant is about 0.5% to about 3% based on the weight of the core.

In certain embodiments, the invention relates to any one of the aforementioned solid dosage forms, further comprising a lubricant, wherein the weight percentage of the lubricant is about 0.5% to about 1% based on the weight of the core.

In certain embodiments, the invention relates to any one of the aforementioned solid dosage forms, further comprising a lubricant, wherein the weight percentage of the lubricant is about 0.5%, about 0.75%, about 1%, about 2%, about 3%, about 4%, or about 5% based on the weight of the core.

In certain embodiments, the invention relates to any one of the aforementioned solid dosage forms, wherein the weight percentage of the coating is about 1% to about 10% based on the weight of the solid particulate. In certain embodiments, the invention relates to any one of the aforementioned solid dosage forms, wherein the weight percentage of the coating is about 9%, about 8%, about 7%, about 6%, about 5%, about 4%, about 3%, about 2%, or about 1% based on the weight of the mini-tablet.

In certain embodiments, the invention relates to any one of the aforementioned solid dosage forms, wherein the weight percentage of the coating is about 3% based on the weight of the solid particulate.

In certain embodiments, the invention relates to any one of the aforementioned solid dosage forms, wherein the weight percentage of the coating is about 2% based on the weight of the solid particulate.

In certain embodiments, the invention relates to any one of the aforementioned solid dosage forms, wherein the weight percentage of the coating is about 1% based on the weight of the solid particulate.

In certain embodiments, the invention relates to any one of the aforementioned solid dosage forms, wherein the solid dosage form is a capsule.

In certain embodiments, the invention relates to any one of the aforementioned solid dosage forms, wherein the solid dosage form is a capsule; and the capsule comprises the plurality of solid particulates.

In certain embodiments, the invention relates to any one of the aforementioned solid dosage forms, wherein the total amount of the active agent is about 20 mg to about 200 mg. In certain embodiments, the active agent is a polyphenol or an aminosterol. In a particular embodiment, the active agent is EGCG. In a particular embodiment, the active agent is an aminosterol.

In certain embodiments, the invention relates to any one of the aforementioned solid dosage forms, wherein the total amount of the active agent is about 20 mg, about 50 mg, about 75 mg, about 100 mg, about 125 mg, about 150 mg, about 175 mg, or about 200 mg.

In certain embodiments, the invention relates to any one of the aforementioned solid dosage forms, wherein the total amount of the active agent is about 20 mg.

In certain embodiments, the invention relates to any one of the aforementioned solid dosage forms, wherein the total amount of active agent is about 50 mg.

In certain embodiments, the invention relates to any one of the aforementioned solid dosage forms, wherein the total amount of active agent is about 75 mg.

In certain embodiments, the invention relates to any one of the aforementioned solid dosage forms, wherein the total amount of active agent is about 100 mg.

In certain embodiments, the invention relates to any one of the aforementioned solid dosage forms, wherein the total amount of active agent is about 125 mg.

In certain embodiments, the invention relates to any one of the aforementioned solid dosage forms, wherein the total amount of active agent is about 150 mg.

In certain embodiments, the invention relates to any one of the aforementioned solid dosage forms, wherein the total amount of active agent is about 175 mg.

In certain embodiments, the invention relates to any one of the aforementioned solid dosage forms, wherein the total amount of active agent is about 200 mg.

In certain embodiments, the invention relates to any one of the aforementioned solid dosage forms, wherein the total amount of the active agent is about 200 mg to about 1,000 mg.

In certain embodiments, the invention relates to any one of the aforementioned solid dosage forms, wherein the total amount of the active agent is about 250 mg, about 375 mg, about 400 mg, about 500 mg, or about 800 mg.

In certain embodiments, the invention relates to any one of the aforementioned solid dosage forms, wherein the total amount of the active agent is about 250 mg.

In certain embodiments, the invention relates to any one of the aforementioned solid dosage forms, wherein the total amount of the active agent is about 375 mg.

In certain embodiments, the invention relates to any one of the aforementioned solid dosage forms, wherein the total amount of the active agent is about 400 mg.

In certain embodiments, the invention relates to any one of the aforementioned solid dosage forms, wherein the total amount of the active agent is about 500 mg.

In certain embodiments, the invention relates to any one of the aforementioned solid dosage forms, wherein the total amount of the active agent is about 800 mg.

In certain embodiments, the solid particulates are compressed into an immediate release tablet, and further comprise one or more excipient compression matrix such as lactose, microcrystalline cellulose, mannitol, and the like, or any combination thereof.

In certain embodiments, the invention relates to any one of the aforementioned solid dosage forms, wherein the mini-tablets do not comprise wax.

In certain embodiments, the invention relates to any one of the aforementioned solid dosage forms, wherein the core is substantially soluble in a liquid with pH from about 1 to about 14, from about 1 to about 7 and from 1 to about 5 at a temperature of about 20° C. to about 40° C.

In certain embodiments, the invention relates to any one of the aforementioned solid dosage forms, wherein the release rate controlling polymer is substantially soluble in a liquid with pH from about 1 to about 5 at a temperature of about 20° C. to about 40° C.

In certain embodiments, the invention relates to any one of the aforementioned solid dosage forms, wherein the diluent is substantially soluble in a liquid with pH from about 1 to about 5 at a temperature of about 20° C. to about 40° C.

In certain embodiments, the invention relates to any one of the aforementioned solid dosage forms, wherein one or more release rate controlling polymers comprising the coating is substantially soluble in a liquid with pH from about 1 to about 14, from about 1 to about 7 and from 1 to about 5 at a temperature of about 20° C. to about 40° C.

In certain embodiments, the invention relates to any one of the aforementioned solid dosage forms, wherein the core is substantially soluble in gastric juice.

In certain embodiments, the invention relates to any one of the aforementioned solid dosage forms, wherein the release rate controlling polymer is substantially soluble in gastric juice.

In certain embodiments, the invention relates to any one of the aforementioned solid dosage forms, wherein the diluent is substantially soluble in gastric juice.

In certain embodiments, the invention relates to any one of the aforementioned solid dosage forms, wherein the release rate controlling polymer comprising the coating is substantially soluble in gastric juice.

In certain embodiments, the invention relates to any one of the aforementioned solid dosage forms, wherein upon contact with gastric juice the active agent is substantially immediately released from the core.

In certain embodiments, the invention relates to any one of the aforementioned solid dosage forms, wherein sustained-release of the active agent from the solid particulates is substantially controlled by the coating.

In certain embodiments, the invention relates to any one of the aforementioned solid dosage forms, wherein the dissolution profile of the active agent in about 900 mL of about 0.05 M phosphate buffer at about pH 7.5 at about 37° C., with paddles rotating at about 50 rpm, is: at about 1 h, between about 5% and about 25%; at about 2 h, between about 30% and about 50%; at about 4 h, between about 60% and about 90%; and at about 8 h, between about 85% and 100%.

In certain embodiments of any one of the aforementioned solid dosage forms, the dissolution profile of the active agent in about 900 mL of about 0.05 M phosphate buffer at about pH 6-7 (e.g., about 6.8) at about 37° C., with paddles rotating at about 100 rpm, is: at about 1 h, at least about 5%; at about 2 h, at least about 10%; at about 4 h, at least about 20%; and at about 8 h, at least about 50%.

In certain embodiments, the invention relates to any one of the aforementioned solid dosage forms, wherein the dissolution profile of the active agent in about 900 mL of simulated gastric fluid (e.g., about 0.1N HCl at about pH 1.2 at about 37° C.), with paddles rotating at about 100 rpm, is: at about 1 h, at least about 10%; at about 2 h, at least about 25%; at about 4 h, at least about 50%; and at about 8 h, at least about 80%.

In certain embodiments, the invention relates to a sustained-release solid dosage form, comprising:
(a) an active agent in an amount effective for treating an amyloid disorder; and
(b) means for delivering to the colon an effective amount of the active agent. In certain embodiments, the active agent is a polyphenol or an aminosterol. In a particular embodiment, the active agent is EGCG. In a particular embodiment, the active agent is an aminosterol.

In certain embodiments, the invention relates to a sustained-release solid dosage form, consisting essentially of:
(a) an active agent in an amount effective for treating Parkinson's Disease; and
(b) means for delivering to the colon an effective amount of the active agent. In certain embodiments, the active agent is a polyphenol or an aminosterol. In a particular embodiment, the active agent is EGCG. In a particular embodiment, the active agent is an aminosterol.

In certain embodiments, the invention relates to a sustained-release solid dosage form, comprising:
(a) an active agent in an amount effective for inducing remission of an amyloid disorder; and
(b) means for delivering to the colon an effective amount of the active agent. In certain embodiments, the active agent is a polyphenol or an aminosterol. In a particular embodiment, the active agent is EGCG. In a particular embodiment, the active agent is an aminosterol.

In certain embodiments, the invention relates to a sustained-release solid dosage form, consisting essentially of:
(a) an active agent in an amount effective for inducing remission of inflammatory bowel disease; and
(b) means for delivering to the colon an effective amount of the active agent. In certain embodiments, the active agent is a polyphenol or an aminosterol. In a particular embodiment, the active agent is EGCG. In a particular embodiment, the active agent is an aminosterol.

In certain embodiments, the invention relates to a sustained-release solid dosage form, comprising:
(a) an active agent in an amount effective for maintaining remission of an amyloid disorder; and
(b) means for delivering to the colon an effective amount of the active agent. In certain embodiments, the active agent is a polyphenol or an aminosterol. In a particular embodiment, the active agent is EGCG. In a particular embodiment, the active agent is an aminosterol.

In certain embodiments, the invention relates to a sustained-release solid dosage form, consisting essentially of:
(a) an active agent in an amount effective for maintaining remission of Parkinson's Disease; and
(b) means for delivering to the colon an effective amount of the active agent. In certain embodiments, the active agent is a polyphenol or an aminosterol. In a particular embodiment, the active agent is EGCG. In a particular embodiment, the active agent is an aminosterol.

In certain embodiments, the invention relates to a sustained-release solid dosage form, comprising a plurality of solid particulates (e.g., mini-tablets, beads, granules, or pellets), wherein each solid particulate comprises:
(a) a core, comprising an active agent in about 50% by weight of the core; microcrystalline cellulose in about 21% by weight of the core; mannitol in about 21% by weight of the core; a lubricant in about 2% by weight of the core; and a glidant in about 0.3% by weight of the core; and
(b) a coating, comprising Eudragard Control in about 45.45% by weight of the coating; HPMC in about 4.61% by weight of the coating; polysorbate (Tween 80) in about 4.48% by weight of the coating; and Talc in about 45.46% by weight of the coating; wherein the coating surrounds the core; and the coating comprises from about 7.5% to about 20.5% by weight of the solid particulate. In certain embodiments, the active agent is a polyphenol or an aminosterol. In a particular embodiment, the active agent is EGCG. In a particular embodiment, the active agent is an aminosterol.

In certain embodiments, the invention relates to a sustained-release solid dosage form, comprising a plurality of solid particulates (e.g., mini-tablets, beads, granules, or pellets), wherein each solid particulate comprises:
(a) a core, comprising an active agent in about 80% by weight of the core; lactose in about 16% by weight of the core; hydroxypropyl cellulose in about 3% by weight of the core; and a lubricant in about 1% by weight of the core; and (b) a coating, comprising ethyl cellulose; a release rate controlling polymer; and triethyl citrate;
wherein the coating surrounds the core; and the coating comprises from about 1% to about 6% by weight of the solid particulate. In certain embodiments, the active agent is a polyphenol or an aminosterol. In a particular embodiment, the active agent is EGCG. In a particular embodiment, the active agent is an aminosterol.

In certain embodiments, the invention relates to a sustained-release solid dosage form, comprising a plurality of solid particulates (e.g., mini-tablets, beads, granules, or pellets), wherein each solid particulate comprises:
(a) a core, comprising an active agent in about 80% by weight of the core; microcrystalline cellulose in about 16% by weight of the core; hydroxypropyl cellulose in about 3% by weight of the core; and a lubricant in about 1% by weight of the core; and
(b) a coating, comprising ethyl cellulose; a release rate controlling polymer; and triethyl citrate;
wherein the coating surrounds the core; and the coating comprises from about 1% to about 6% by weight of the solid particulate. In certain embodiments, the active agent is a polyphenol or an aminosterol. In a particular embodiment, the active agent is EGCG. In a particular embodiment, the active agent is an aminosterol.

In certain embodiments, the invention relates to a sustained-release solid dosage form, comprising a plurality of solid particulates, wherein each solid particulate comprises:
(a) a core, comprising an active agent in about 80% by weight of the core; lactose in about 16% by weight of the core; hydroxypropyl cellulose in about 3% by weight of the core; and a lubricant in about 1% by weight of the core; and
(b) a coating, comprising ethyl cellulose; a release rate controlling polymer, wherein said release rate controlling polymer is selected from the group consisting of hydroxypropyl cellulose and hydroxypropyl methyl cellulose; and triethyl citrate;
wherein the coating surrounds the core; and the coating comprises from about 1% to about 6% by weight of the solid particulate. In certain embodiments, the active agent is a polyphenol or an aminosterol. In a particular embodiment, the active agent is EGCG. In a particular embodiment, the active agent is an aminosterol.

In certain embodiments, the invention relates to a sustained-release solid dosage form, comprising a plurality of solid particulates, wherein each solid particulate comprises:
(a) a core, comprising an active agent in about 80% by weight of the core; lactose in about 16% by weight of the core; hydroxypropyl cellulose in about 3% by weight of the core; and a lubricant in about 1% by weight of the core; and
(b) a coating, comprising ethyl cellulose; hydroxypropyl cellulose; and triethyl citrate; wherein the coating surrounds the core; and the coating comprises from about 1% to about 6% by weight of the solid particulate. In certain embodiments, the active agent is a polyphenol or an aminosterol. In a particular embodiment, the active agent is EGCG. In a particular embodiment, the active agent is an aminosterol.

In certain embodiments, the invention relates to a sustained-release solid dosage form, comprising a plurality of solid particulates, wherein each solid particulate comprises:
(a) a core, comprising an active agent in about 80% by weight of the core; lactose in about 16% by weight of the core; hydroxypropyl cellulose in about 3% by weight of the core; and a lubricant in about 1% by weight of the core; and
(b) a coating, comprising ethyl cellulose; hydroxypropyl methyl cellulose; and triethyl citrate;
wherein the coating surrounds the core; and the coating comprises from about 1% to about 6% by weight of the solid particulate. In certain embodiments, the active agent is a polyphenol or an aminosterol. In a particular embodiment, the active agent is EGCG. In a particular embodiment, the active agent is an aminosterol.

In certain embodiments, the invention relates to a sustained-release solid dosage form, comprising a plurality of solid particulates, wherein each solid particulate comprises:
(a) a core, comprising an active agent in about 80% by weight of the core; microcrystalline cellulose in about 16% by weight of the core; hydroxypropyl cellulose in about 3% by weight of the core; and a lubricant in about 1% by weight of the core; and
(b) a coating, comprising ethyl cellulose; a release rate controlling polymer, wherein said release rate controlling polymer is selected from the group consisting of hydroxypropyl cellulose and hydroxypropyl methyl cellulose; and triethyl citrate;
wherein the coating surrounds the core; and the coating comprises from about 1% to about 6% by weight of the solid particulate. In certain embodiments, the active agent is a polyphenol or an aminosterol. In a particular embodiment, the active agent is EGCG. In a particular embodiment, the active agent is an aminosterol.

In certain embodiments, the invention relates to a sustained-release solid dosage form, comprising a plurality of solid particulates, wherein each solid particulate comprises:
(a) a core, comprising an active agent in about 80% by weight of the core; microcrystalline cellulose in about 16% by weight of the core; hydroxypropyl cellulose in about 3% by weight of the core; and a lubricant in about 1% by weight of the core; and
(b) a coating, comprising ethyl cellulose; hydroxypropyl cellulose; and triethyl citrate; wherein the coating surrounds the core; and the coating comprises from about 1% to about 6% by weight of the solid particulate. In certain embodiments, the active agent is a polyphenol or an aminosterol. In a particular embodiment, the active agent is EGCG. In a particular embodiment, the active agent is an aminosterol.

In certain embodiments, the invention relates to a sustained-release solid dosage form, comprising a plurality of solid particulates, wherein each solid particulate comprises:
(a) a core, comprising an active agent in about 80% by weight of the core; microcrystalline cellulose in about 16% by weight of the core; hydroxypropyl cellulose in about 3% by weight of the core; and a lubricant in about 1% by weight of the core; and
(b) a coating, comprising ethyl cellulose; hydroxypropyl methyl cellulose; and triethyl citrate;
wherein the coating surrounds the core; and the coating comprises from about 1% to about 6% by weight of the solid particulate. In certain embodiments, the active agent is a polyphenol or an aminosterol. In a particular embodiment, the active agent is EGCG. In a particular embodiment, the active agent is an aminosterol.

In certain embodiments, the invention relates to any one of the aforementioned solid dosage forms, wherein the solid dosage form is an oral solid dosage form.

In some embodiments, the coating comprises at least about 1%, at least about 3%, at least about 5%, at least about 10%, at least about 20%, at least about 30%, at least about 40%, or at least about 50% by weight of the solid particulate and/or solid dosage form. In certain embodiments, the coating comprises less than or equal to about 60%, less than or equal to about 50%, less than or equal to about 40%, less than or equal to about 30%, less than or equal to about 20%, less than or equal to about 10%, less than or equal to about 6%, less than or equal to about 5%, or less than or equal to about 3% by weight of the solid particulate and/or solid dosage form. Combinations of these ranges are also possible (e.g., 3-6%, 5-10%, or 10-50%).

In one embodiment, the invention relates to any one of the above-mentioned solid dosage forms for use in the treatment of an amyloid disorder.

In one embodiment, the invention relates to any one of the above-mentioned solid dosage forms for use in inducing remission of an amyloid disorder.

In one embodiment, the invention relates to any one of the above-mentioned solid dosage forms for use in maintaining remission of and amyloid disorder.

In one embodiment, the invention relates to any one of the above-mentioned solid dosage forms for use in the treatment of Parkinson's Disease.

In one embodiment, the invention relates to any one of the above-mentioned solid dosage forms for use in inducing remission of Parkinson's Disease.

In one embodiment, the invention relates to any one of the above-mentioned solid dosage forms for use in maintaining remission of Parkinson's Disease.

In one embodiment, the invention relates to any one of the above-mentioned solid dosage forms for use in preventing or slowing progression of Parkinson's Disease. In some embodiments, colonic transit times in Parkinson's Disease subjects are reduced. In some embodiments, colonic transit times in Parkinson's Disease subjects are reduced at least 10% at least 20% at least 30%, at least 40%, at least 50%, or at least 60%. In certain embodiments, the colonic transit time is reduced in Parkinson's Disease subject by less than or equal to 90%, less than or equal to 80%, less than or equal to 70%, less than or equal to 60%, less than or equal to 50%, or less than or equal to 40%. Combinations of these ranges are also possible (e.g., 10-80%, 20-60%, or 30-50% reductions).

In certain embodiments, colonic transit times in Parkinson's Disease subjects are reduced by at least 4 hours, at least 6 hours, at least 12 hours, at least 18 hours, at least 24 hours, at least 30 hours, or at least 36 hours. In some embodiments, colonic transit times in Parkinson's Disease subjects are reduced by less than or equal to 96 hours, less than or equal to 84 hours, less than or equal to 72 hours, less than or equal to 60 hours, less than or equal to 48 hours, less than or equal to 36 hours, less than or equal to 24 hours, or less than or equal to 12 hours. Combinations of these ranges are also possible (e.g., 4-36 hours, 6-12 hours, 6-48 hours, 12-96 hours, 24-72 hours, or 36-60 hours reduction).

In some embodiments, colonic transit times in Parkinson's Disease subjects are reduced. In some embodiments, colonic transit times in Parkinson's Disease subjects are reduced at least 10% at least 20% at least 30%, at least 40%, at least 50%, or at least 60%. In certain embodiments, the colonic transit time is reduced in Parkinson's Disease subject by less than or equal to 90%, less than or equal to 80%, less than or equal to 70%, less than or equal to 60%, less than or equal to 50%, or equal to 50%, or less than or equal to 40%. Combinations of these ranges are also possible (e.g., 10-80%, 20-60%, or 30-50% reductions). In some embodiments, whole gut transit times in Parkinson's Disease subjects are reduced. In some embodiments, whole gut transit times in Parkinson's Disease subjects are reduced at least 10% at least 20% at least 30%, at least 40%, at least 50%, or at least 60%. In certain embodiments, the whole gut transit time is reduced in Parkinson's Disease subject by less than or equal to 90%, less than or equal to 80%, less than or equal to 70%, less than or equal to 60%, less than or equal to 50%, or less than or equal to 40%. Combinations of these ranges are also possible (e.g., 10-80%, 20-60%, or 30-50% reductions).

In certain embodiments, whole gut transit times in Parkinson's Disease subjects are reduced by at least 4 hours, at least 6 hours, at least 12 hours, at least 18 hours, at least 24 hours, at least 30 hours, or at least 36 hours. In some embodiments, whole gut transit times in Parkinson's Disease subjects are reduced by less than or equal to 96 hours, less than or equal to 84 hours, less than or equal to 72 hours, less than or equal to 60 hours, less than or equal to 48 hours, less than or equal to 36 hours, less than or equal to 24 hours, or less than or equal to 12 hours. Combinations of these ranges are also possible (e.g., 4-36 hours, 6-12 hours, 6-48 hours, 12-96 hours, 24-72 hours, or 36-60 hours reduction).

In some embodiments, colonic and/or whole gut transit times in subjects are reduced.

In some embodiments, colonic and/or whole gut transit times in subjects are reduced at least 10% at least 20% at least 30%, at least 40%, at least 50%, or at least 60%. In certain embodiments, the colonic and/or whole gut transit times transit time is reduced in subjects by less than or equal to 90%, less than or equal to 80%, less than or equal to 70%, less than or equal to 60%, less than or equal to 50%, or less than or equal to 40%. Combinations of these ranges are also possible (e.g., 10-80%, 20-60%, or 30-50% reductions).

In certain embodiments, colonic and/or whole gut transit times in subjects are reduced by at least 4 hours, at least 6 hours, at least 12 hours, at least 18 hours, at least 24 hours, at least 30 hours, or at least 36 hours. In some embodiments, colonic and/or whole gut transit times transit times in subjects are reduced by less than or equal to 96 hours, less than or equal to 84 hours, less than or equal to 72 hours, less than or equal to 60 hours, less than or equal to 48 hours, less than or equal to 36 hours, less than or equal to 24 hours, or less than or equal to 12 hours. Combinations of these ranges are also possible (e.g., 4-36 hours, 6-12 hours, 6-48 hours, 12-96 hours, 24-72 hours, or 36-60 hours reduction).

In some embodiments, the invention relates to any one of the above-mentioned solid dosage forms for use in inhibiting CsgA aggregation.

In some embodiments, the invention relates to any one of the above-mentioned solid dosage forms for use in inhibiting curli formation.

In certain embodiments, the invention relates to a method of treating intestinal dysbiosis, intestinal hyperpermeability, irritable bowel syndrome, ulcerative colitis, Crohn's disease, and inflammatory bowel disease, comprising the step of orally administering to a mammal in need thereof a therapeutically effective amount of any one of the aforementioned solid dosage forms.

In certain embodiments, the invention relates to a method of inducing remission of inflammatory bowel disease, comprising the step of orally administering to a mammal in need thereof a therapeutically effective amount of any one of the aforementioned solid dosage forms. In certain embodiments, "remission" (clinical or endoscopic) is defined as a Ulcerative Colitis Disease Activity Index (UCDAI) score of ≤1, with scores of 0 for both rectal bleeding and stool frequency, normal mucosa (no friability) on endoscopy, and a ≥1 point reduction in the Endoscopic Index (EI) score. The UCDAI is explained in more detail in Sutherland et al. Gastroenterology 1987, 92, 1894-98, and Walmsley, et al. Gut 1998, 43, 29-32. Alternatively, remission is defined as complete resolution of symptoms plus improvement of endoscopic endpoints (e.g., a "1" score for one of the endoscopic components (mucosal vascular pattern, erythema, granularity, or friability), and "0" for the others). An alternative or additional measure is Sigmoidoscopic Index (SI)—an objective measure of disease activity rated by a standard 15-point scale that includes mucosal vascular pattern, erythema, friability, granularity/ulcerations, and mucopus as an improvement over baseline. Secondary efficacy parameters that also may be indicative of remission include, but are not limited to, reduction in the frequency of trips to the toilet, improved stool consistency, decreased rectal bleeding, decreased abdominal pain/rectal pain, and decreased urgency compared to these measures prior the administration of a solid oral dosage form according to the present invention.

In certain embodiments, the invention relates to a method of maintaining remission of inflammatory bowel disease, comprising the step of orally administering to a mammal in need thereof a therapeutically effective amount of any one of the aforementioned solid dosage forms.

In certain embodiments, the invention relates to a method, comprising the steps of:
orally administering to a mammal in need thereof a therapeutically effective amount of any one of the aforementioned solid dosage forms for a first period of time; and
orally co-administering to the mammal a therapeutically effective amount of an aminosterol and a therapeutically effective amount of any one of the aforementioned solid dosage forms for a second period of time, thereby inducing remission of inflammatory bowel disease.

In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease.

In certain embodiments, the invention relates to a method, comprising the steps of:
orally administering to a mammal in need thereof a therapeutically effective amount of any one of the aforementioned solid dosage forms for a first period of time;
orally co-administering to the mammal a therapeutically effective amount of an aminosterol and a therapeutically effective amount of any one of the aforementioned solid dosage forms for a second period of time, thereby inducing remission of an amyloid disorder; and
orally administering to the mammal a therapeutically effective amount of any one of the aforementioned solid dosage forms for a third period of time, thereby maintaining remission of an amyloid disorder.

In certain embodiments, the invention relates to a method, comprising the steps of:
orally administering to a mammal in need thereof a therapeutically effective amount of any one of the aforementioned solid dosage forms for a first period of time;
orally co-administering to the mammal a therapeutically effective amount of an aminosterol and a therapeutically effective amount of any one of the aforementioned solid dosage forms for a second period of time, thereby inducing remission of Parkinson's Disease; and
orally administering to the mammal a therapeutically effective amount of any one of the aforementioned solid dosage forms for a third period of time, thereby maintaining remission of Parkinson's Disease.

In certain embodiments, the invention relates to a method, comprising the steps of:
orally administering to a mammal in need thereof a therapeutically effective amount of any one of the aforementioned solid dosage forms for a first period of time;
orally co-administering to the mammal a therapeutically effective amount of an aminosterol and a therapeutically effective amount of any one of the aforementioned solid dosage forms for a second period of time, thereby inducing remission of irritable bowel syndrome or inflammatory bowel disease; and
orally administering to the mammal a therapeutically effective amount of any one of the aforementioned solid dosage forms for a third period of time, thereby maintaining remission of irritable bowel syndrome or inflammatory bowel disease.

In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease.

In certain embodiments, the invention relates to any one of the aforementioned methods, wherein the first period of time is from about 3 weeks to about 9 weeks. In certain embodiments, the invention relates to any one of the aforementioned methods, wherein the first period of time is about 3 weeks, about 4 weeks, about 5 weeks, about 6 weeks, about 7 weeks, about 8 weeks, or about 9 weeks.

In certain embodiments, the invention relates to any one of the aforementioned methods, wherein the second period of time is from about 4 weeks to about 12 weeks. In certain embodiments, the invention relates to any one of the aforementioned methods, wherein the second period of time is about 4 weeks, about 5 weeks, about 6 weeks, about 7 weeks, about 8 weeks, about 9 weeks, about 10 weeks, about 11 weeks, or about 12 weeks.

In certain embodiments, the invention relates to any one of the aforementioned methods, wherein the third period of time is from about 3 weeks to about 9 weeks. In certain embodiments, the invention relates to any one of the aforementioned methods, wherein the third period of time is about 3 weeks, about 4 weeks, about 5 weeks, about 6 weeks, about 7 weeks, about 8 weeks, or about 9 weeks.

In certain embodiments, the invention relates to any one of the aforementioned methods, wherein the aminosterol and the solid dosage, when administered for the second period of time, effectively induce remission of inflammatory bowel disease.

In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease.

In certain embodiments, the invention relates to a method, comprising the steps of:
orally administering to a mammal in need thereof a therapeutically effective amount of an aminosterol for a fourth period of time, thereby inducing remission of inflammatory bowel disease; and
orally administering to the mammal a therapeutically effective amount of any one of the aforementioned solid dosage forms for a fifth period of time, thereby maintaining remission of inflammatory bowel disease.

In certain embodiments, the invention relates to any one of the aforementioned methods, wherein the therapeutically effective amount of the aminosterol, when administered for the fourth period of time, effectively induces remission of inflammatory bowel disease.

In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease.

In certain embodiments, the invention relates to any one of the aforementioned methods, wherein the fourth period of time is from about 4 weeks to about 12 weeks. In certain embodiments, the invention relates to any one of the aforementioned methods, wherein the fourth period of time is about 4 weeks, about 5 weeks, about 6 weeks, about 7 weeks, about 8 weeks, about 9 weeks, about 10 weeks, about 11 weeks, or about 12 weeks.

In certain embodiments, the invention relates to any one of the aforementioned methods, wherein the fifth period of time is from about 3 weeks to about 9 weeks. In certain embodiments, the invention relates to any one of the aforementioned methods, wherein the fifth period of time is about 3 weeks, about 4 weeks, about 5 weeks, about 6 weeks, about 7 weeks, about 8 weeks, or about 9 weeks.

In certain embodiments, the invention relates to a method of maintaining remission of inflammatory bowel disease, comprising the steps of:
orally co-administering to a mammal in need thereof a therapeutically effective amount of an aminosterol and a therapeutically effective amount of any one of the aforementioned solid dosage forms for a sixth period of time, thereby maintaining remission of inflammatory bowel disease.

In certain embodiments, the invention relates to any one of the aforementioned methods, wherein the sixth period of time is from about 4 weeks to about 12 weeks. In certain embodiments, the invention relates to any one of the aforementioned methods, wherein the sixth period of time is about 4 weeks, about 5 weeks, about 6 weeks, about 7 weeks, about 8 weeks, about 9 weeks, about 10 weeks, about 11 weeks, or about 12 weeks.

In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease.

In certain embodiments, the invention relates to a method of maintaining remission of inflammatory bowel disease, comprising the steps of:
orally administering to a mammal in need thereof a therapeutically effective amount of an aminosterol for a seventh period of time, thereby maintaining remission of inflammatory bowel disease.

In certain embodiments, the invention relates to any one of the aforementioned methods, wherein the seventh period of time is from about 4 weeks to about 12 weeks. In certain embodiments, the invention relates to any one of the aforementioned methods, wherein the seventh period of time is about 4 weeks, about 5 weeks, about 6 weeks, about 7 weeks, about 8 weeks, about 9 weeks, about 10 weeks, about 11 weeks, or about 12 weeks.

In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease.

In certain embodiments, the invention relates to any one of the aforementioned methods, wherein the inflammatory bowel disease is ulcerative colitis.

In certain embodiments, the invention relates to any one of the aforementioned methods, wherein the inflammatory bowel disease is Crohn's disease.

In certain embodiments, the invention relates to any one of the aforementioned methods, wherein the method is a method of treating or inducing remission of ulcerative colitis; and the ulcerative colitis is mildly active.

In certain embodiments, the invention relates to any one of the aforementioned methods, wherein the method is a method of treating or inducing remission of ulcerative colitis; and the ulcerative colitis is moderately active.

In certain embodiments, the invention relates to any one of the aforementioned methods, wherein the method is a method of maintaining remission of ulcerative colitis; and the ulcerative colitis was mildly active prior to remission.

In certain embodiments, the invention relates to any one of the aforementioned methods, wherein the method is a method of maintaining remission of ulcerative colitis; and the ulcerative colitis was moderately active prior to remission.

In certain embodiments, the invention relates to any one of the aforementioned methods, wherein the mammal is a primate, canine or feline.

In certain embodiments, the invention relates to any one of the aforementioned methods, wherein the mammal is a human.

In certain embodiments, the invention relates to any one of the aforementioned methods, wherein the solid dosage form is administered one, two, three or four times a day.

In certain embodiments, the invention relates to any one of the aforementioned methods, wherein the solid dosage form is administered one time a day.

In certain embodiments, the invention relates to any one of the aforementioned methods, wherein the solid dosage form is administered two times a day.

In certain embodiments, the invention relates to any one of the aforementioned methods, wherein the solid dosage form is administered three times a day.

In certain embodiments, the invention relates to any one of the aforementioned methods, wherein the solid dosage form is administered four times a day.

In certain embodiments, the invention relates to any one of the aforementioned methods, wherein the total daily dose of the active agent is about 1 g to about 5 g.

In certain embodiments, the invention relates to any one of the aforementioned methods, wherein the total daily dose of the active agent is about 1.5 g, about 1.6 g, about 2.4 g, or about 4 g.

In certain embodiments, the invention relates to any one of the aforementioned methods, wherein the total daily dose of the active agent is about 1.5 g.

In certain embodiments, the invention relates to any one of the aforementioned methods, wherein the total daily dose of the active agent is about 1.6 g.

In certain embodiments, the invention relates to any one of the aforementioned methods, wherein the total daily dose of the active agent is about 2.4 g.

In certain embodiments, the invention relates to any one of the aforementioned methods, wherein the total daily dose of the active agent is about 4 g.

In certain embodiments, the invention relates to any one of the aforementioned methods, wherein the solid dosage form is administered four times a day; each solid dosage form comprises about 1 g of the active agent; and the total daily dose of the active agent is about 4 g.

In certain embodiments, the invention relates to any one of the aforementioned methods, wherein the solid particulates pass substantially freely through the pyloric sphincter of the stomach.

In certain embodiments, the invention relates to any one of the aforementioned methods, further comprising the step of co-administering to the mammal in need thereof a therapeutically effective amount of an aminosterol.

In certain embodiments, the invention relates to any one of the aforementioned methods, wherein the aminosterol is selected from the group consisting of squalamine, a squalamine isomer, a sterol nucleus and a polyamine attached to any position on the sterol such that the molecule exhibits a net charge of at least +1, the charge being contributed by the polyamine, a substituted aminosterol, methylprednisolone, and a derivative of squalamine or natural aminosterol derivative.

In certain embodiments, the invention relates to any one of the aforementioned methods, wherein the aminosterol is squalamine.

In certain embodiments, the invention relates to any one of the aforementioned methods, wherein the aminosterol is squalamine or a pharmaceutically acceptable salt thereof.

In certain embodiments, the invention relates to any one of the aforementioned methods, wherein the aminosterol is Aminosterol 1436, or a pharmaceutically acceptable salt thereof.

In certain embodiments, the invention relates to any one of the aforementioned methods, wherein the aminosterol is squalamine; and the squalamine is administered orally in a solid dosage form.

In certain embodiments, the invention relates to any one of the aforementioned methods, wherein the total daily dose of squalamine is about 3 mg to about 12 mg, or about 6 mg to about 9 mg.

In certain embodiments, the invention relates to any one of the aforementioned methods, wherein the total daily dose of squalamine is about 3 mg, about 6 mg, about 9 mg, or about 12 mg.

In certain embodiments, the invention relates to any one of the aforementioned methods, wherein the total daily dose of squalamine is about 6 mg; and the method is a method of maintaining remission of inflammatory bowel disease.

In certain embodiments, the invention relates to any one of the aforementioned methods, wherein the total daily dose of squalamine is about 6 mg; the method is a method of maintaining remission of inflammatory bowel disease; and the squalamine is administered for about 1 week to about 12 months.

In certain embodiments, the invention relates to any one of the aforementioned methods, wherein the total daily dose of squalamine is about 9 mg.

In certain embodiments, the invention relates to any one of the aforementioned methods, wherein the total daily dose of squalamine is about 9 mg; and the method is a method of inducing remission of inflammatory bowel disease.

In certain embodiments, the invention relates to any one of the aforementioned methods, wherein the total daily dose of squalamine is about 9 mg; the method is a method of inducing remission of inflammatory bowel disease; and the squalamine is administered for about 1 week to about 8 weeks.

In certain embodiments, the invention relates to any one of the aforementioned methods, wherein the aminosterol is squalamine.

In certain embodiments, the invention relates to any one of the aforementioned methods, wherein the aminosterol is squalamine; and the squalamine is in the form of an extended release tablet. In certain embodiments, the invention relates to any one of the aforementioned methods, wherein the aminosterol is squalamine; and the squalamine is in the form of an extended release tablet as described herein.

In certain embodiments, the invention relates to any one of the aforementioned methods, wherein the aminosterol is squalamine; and the squalamine is in a solid dosage form consisting essentially of squalamine, stearic acid, lecithin, microcrystalline cellulose, hydroxypropyl cellulose, lactose monohydrate, silicon dioxide, magnesium stearate, a first acrylic/methacrylic copolymer, a second acrylic/methacrylic copolymer, talc, titanium dioxide, triethyl citrate, and alcohol.

In certain embodiments, the invention relates to any one of the aforementioned methods, wherein the aminosterol is squalamine; and the squalamine is in a solid dosage form consisting essentially of a tablet core and a coating. In certain embodiments, the squalamine tablet core consists essentially of squalamine, stearic acid, lecithin, microcrystalline cellulose, hydroxypropyl cellulose, lactose monohydrate, silicon dioxide, and magnesium stearate. In certain embodiments, the squalamine tablet coating consists essentially of a first acrylic/methacrylic copolymer, a second acrylic/methacrylic copolymer, talc, titanium dioxide, triethyl citrate, and alcohol.

In certain embodiments, the invention relates to any one of the aforementioned methods, wherein the aminosterol is squalamine; the squalamine is in a solid dosage form consisting essentially of a tablet core and a coating; the squalamine tablet core consists essentially of squalamine, stearic acid, lecithin, microcrystalline cellulose, hydroxypropyl cellulose, lactose monohydrate, silicon dioxide, and magnesium stearate; and the squalamine tablet coating consists essentially of a first acrylic/methacrylic copolymer, a second acrylic/methacrylic copolymer, talc, titanium dioxide, triethyl citrate, and alcohol.

In certain embodiments, the invention relates to any one of the aforementioned methods, wherein the aminosterol is squalamine; the squalamine is in a solid dosage form comprising a tablet core and a coating; the squalamine tablet core comprises about 6 mg squalamine, about 10 mg stearic acid, about 10 mg lecithin, about 156 mg microcrystalline cellulose, about 60 mg hydroxypropyl cellulose, about 53 mg lactose monohydrate, about 2 mg silicon dioxide, and about 3 mg magnesium stearate; and the squalamine tablet coating comprises about 8 mg of a first acrylic/methacrylic copolymer, about 8 mg of a second acrylic/methacrylic copolymer, about 7.9 mg of talc, about 4.5 mg titanium dioxide, about 1.6 mg of triethyl citrate, and alcohol.

In certain embodiments, the invention relates to any one of the aforementioned methods, wherein the aminosterol is squalamine; the squalamine is in a solid dosage form comprising a tablet core and a coating; the squalamine tablet core comprises 9.0 mg squalamine, about 10 mg stearic acid, about 10 mg lecithin, about 156 mg microcrystalline cellulose, about 60 mg hydroxypropyl cellulose, about 50 mg lactose monohydrate, about 2 mg silicon dioxide, and about 3 mg magnesium stearate; and the tablet core is coated with a coating comprising about 8 mg of a first acrylic/methacrylic copolymer, about 8 mg of a second acrylic/methacrylic copolymer, about 7.9 mg of talc, about 4.5 mg titanium dioxide, about 1.6 mg of triethyl citrate, and alcohol.

In certain embodiments, the invention relates to any one of the aforementioned methods, wherein the aminosterol is squalamine; the squalamine is in a solid dosage form consisting essentially of a tablet core and a coating; the squalamine tablet core consists essentially of about 6.0 mg squalamine, about 10.0 mg stearic acid, about 10.0 mg lecithin, about 156.0 mg microcrystalline cellulose, about 60.0 mg hydroxypropyl cellulose, about 53.0 mg lactose monohydrate, about 2.0 mg silicon dioxide, and about 3.0 mg magnesium stearate; and the squalamine tablet coating consists essentially of about 8.0 mg of a first acrylic/methacrylic copolymer, about 8.0 mg of a second acrylic/methacrylic copolymer, about 7.9 mg of talc, about 4.5 mg titanium dioxide, about 1.6 mg of triethyl citrate, and alcohol.

In certain embodiments, the invention relates to any one of the aforementioned methods, wherein the aminosterol is squalamine; and the squalamine is in a solid dosage form described in U.S. Pat. Nos. 10,040,817, 8,623,416, and U.S. Pat. Applications US 2017/0327530, US 2017/0326156, US 2018/0319837, and US 2018/0327445, (the contents of all of which are hereby incorporated by reference in their entireties).

In certain embodiments, the invention relates to any one of the aforementioned methods, wherein the aminosterol is Aminosterol 1436; the Aminosterol 1436 is in a solid dosage form; and the Aminosterol 1436 solid dosage form is an extended release tablet.

In certain embodiments, the invention relates to any one of the aforementioned methods, wherein the aminosterol is squalamine; the squalamine is in a solid dosage form; and the squalamine solid dosage form is an extended release tablet.

In one embodiment, the invention relates to any one of the above-mentioned methods, wherein the method is used for a period of treatment. In one embodiment, the invention relates to any one of the above-mentioned methods, wherein the period of treatment is about 1 week to about 36 months. In one embodiment, the invention relates to any one of the above-mentioned methods, wherein the period of treatment is about 1, 2, 3, 4, 5, 6, 7, or 8 weeks. In one embodiment, the invention relates to any one of the above-mentioned methods, wherein the period of treatment is about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months.

In some embodiments according to the compositions (e.g., sustained release dosage forms) and methods disclosed herein, said composition may be co-administered with caffeine, nicotine, theophylline, theobromine, xanthine, methylxanthine, or derivatives thereof. In some embodiments, the methods as disclosed herein further comprise administering to said subject an inhibitor of α-synuclein aggregation. In some embodiments, the methods as disclosed herein further comprise administering to said subject L-DOPA, carbidopa, Lodosyn, levodopa, Droxidopa, Northera, Rasagiline, apomorphine hydrochloride, Bromocriptine, Rotigotine, Pramipexole, Ropinirole, Benzotropine, Trihexyphenidyl, Selegiline, Entacapone, Tolcapone, Amantadine, Pimavanersin, Rivastigmine or the like, or any combination thereof. In some embodiments, the methods as disclosed herein comprise administering to said subject an inhibitor of α-synuclein aggregation, and further comprise administering to said subject L-DOPA, carbidopa, Lodosyn, levodopa, Droxidopa, Northera, Rasagiline, apomorphine hydrochloride, Bromocriptine, Rotigotine, Pramipexole, Ropinirole, Benzotropine, Trihexyphenidyl, Selegiline, Entacapone, Tolcapone, Amantadine, Pimavanersin, Rivastigmine or the like, or any combination thereof. In some embodiments, the inhibitor of α-synuclein aggregation and the L-DOPA, carbidopa, Lodosyn, levodopa, Droxidopa, Northera, Rasagiline, apomorphine hydrochloride, Bromocriptine, Rotigotine, Pramipexole, Ropinirole, Benzotropine, Trihexyphenidyl, Selegiline, Entacapone, Tolcapone, Amantadine, Pimavanersin, Rivastigmine or the like are administered in the same composition. In some embodiments, the inhibitor of α-synuclein aggregation and the L-DOPA, carbidopa, Lodosyn, levodopa, Droxidopa, Northera, Rasagiline, apomorphine hydrochloride, Bromocriptine, Rotigotine, Pramipexole, Ropinirole, Benzotropine, Trihexyphenidyl, Selegiline, Entacapone, Tolcapone, Amantadine, Pimavanersin, Rivastigmine or the like are administered in separate compositions. In some embodiments, the separate compositions are administered at the same time. In some embodiments, the separate compositions are administered at the different times.

In one embodiment, the invention relates to the use of an active agent in the manufacture of a sustained release dosage form medicament for the treatment of an amyloid disorder. In certain embodiments, the amyloid disorder is an α-synucleinopathy or Parkinson's Disease. In certain embodiments, the amyloid disorder is Lewy Body Dementia (LBD). In certain embodiments, the amyloid disorder is Lewy body variant of Alzheimer's disease. In certain embodiments, the active agent is a polyphenol or an aminosterol. In a particular embodiment, the active agent is EGCG. In a particular embodiment, the active agent is an aminosterol.

In one embodiment, the invention relates to the use of an active agent in the manufacture of a sustained release dosage form medicament for inducing remission of an amyloid disorder. In certain embodiments, the amyloid disorder is an α-synucleinopathy or Parkinson's Disease. In certain embodiments, the amyloid disorder is Lewy Body Dementia (LBD). In certain embodiments, the amyloid disorder is Lewy body variant of Alzheimer's disease. In certain embodiments, the active agent is a polyphenol or an aminosterol. In a particular embodiment, the active agent is EGCG. In a particular embodiment, the active agent is an aminosterol.

In one embodiment, the invention relates to the use of an active agent in the manufacture of a sustained release dosage form medicament for maintaining remission of inflammatory bowel disease. In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease. In certain embodiments, the active agent is a polyphenol or an aminosterol. In a particular embodiment, the active agent is EGCG. In a particular embodiment, the active agent is an aminosterol.

In one embodiment, the invention relates to the use of an active agent in the manufacture of a sustained release dosage form medicament for the treatment of inflammatory bowel disease. In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease. In certain embodiments, the active agent is a polyphenol or an aminosterol. In a particular embodiment, the active agent is EGCG. In a particular embodiment, the active agent is an aminosterol.

In one embodiment, the invention relates to the use of an active agent in the manufacture of a sustained release dosage form medicament for inducing remission of inflammatory bowel disease. In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease. In certain embodiments, the active agent is a polyphenol or an aminosterol. In a particular embodiment, the active agent is EGCG. In a particular embodiment, the active agent is an aminosterol.

In one embodiment, the invention relates to the use of an active agent in the manufacture of a sustained release dosage form medicament for maintaining remission of inflammatory bowel disease. In certain embodiments, the inflammatory bowel disease is ulcerative colitis or Crohn's Disease. In certain embodiments, the inflammatory bowel disease is ulcerative colitis. In certain embodiments, the inflammatory bowel disease is Crohn's Disease. In certain embodiments, the active agent is a polyphenol or an aminosterol. In a particular embodiment, the active agent is EGCG. In a particular embodiment, the active agent is an aminosterol.

The following examples provide illustrative methods for making and testing the effectiveness of exemplary sustained-release solid dosage forms. These examples are provided for illustrative purposes only and not to limit the scope of the items provided herein. All of the methods disclosed and claimed herein can be made and executed without undue experimentation in light of the present disclosure. It will be apparent to those of ordinary skill in the art that variations may be applied to the methods and in the steps or in the sequence of steps of the method described herein without departing from the concept, spirit and scope of the claims. All such similar substitutes and modifications apparent to those of ordinary skill in the art are deemed to be within the spirit, scope and concept of the appended claims.

While certain embodiments of the present invention have been shown and described herein, it will be apparent to those of ordinary skill in the art that such embodiments are provided by way of example only. Numerous variations, changes, and substitutions will now occur to those of ordinary skill in the art without departing from the invention. It should be understood that various alternatives to the embodiments of the invention as shown and described herein may be employed in practicing the invention. It is intended that the following claims define the scope of the invention and that methods and structures within the scope of these claims and their equivalents be covered thereby.

EXAMPLES

Materials

All active agents, polymers, excipients, solvents and reagents are available commercially and were used as received from commercial vendors.

EUDRAGUARD® control is a coating material comprising xxx manufactured by Evonik Industries AG.

EUDRAGUARD® control, Eudragit® NE 30 D, Eudragit® RS PO, and Eudragit® RL PO are time-controlled release acrylate/methacrylate copolymers having the following formula:

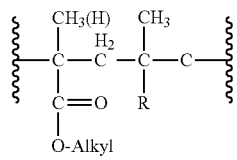

wherein R is —CO$_2$CH$_3$ (methacrylic ester or acrylic ester copolymers), or —CO$_2$CH$_2$CH$_2$N(CH$_3$)$_3$Cl (alkylammonium methacrylate or alkylammonium acrylate copolymers). Eudragit® RL PO comprises a higher amount (50 mEq/100 g polymer) of the quaternary ammonium substituent than Eudragit® RS PO (25 mEq/100 g polymer). Eudragit and EUDRAGUARD polymers are manufactured by Evonik Industries AG.

Carbopol 971P is a polyacrylic acid polymer manufactured by Lubrizol Corporation.

HPMC E-5 (also known as Methocel E5) is a low molecular weight hydroxypropyl methylcellulose product having a viscosity of ~5 cP at 2% in water. HPMC E10M (also known as HPMC CR and Methocel E10) is a medium molecular weight hydroxypropyl methylcellulose product having a viscosity of 10,000 cP at 2% in water. Methocel products are manufactured by DuPont.

Kollicoat SR 30D is a low-viscosity aqueous dispersion of polyvinyl acetate.

Example 1: Preparation of Dosage Forms

Part A: General Procedure
1. Matrix-Mini Tablets or Tablets:

Mix the active ingredient with an insoluble and/or slowly soluble polymer and excipients such as fillers, binders, glidants, lubricants, colorants, etc. If necessary, wet- or dry-granulate the mixture. If granulated, the granules can be mixed with additional excipients. Compress the blend. The compressed tablets may be coated for cosmetic purposes. Said compressed dosage forms, as shown and described herein, further provide a matrix-controlled release rate dosage form. The coating may contain active ingredient, to provide an immediate release portion.

2. Matrix Particles:

Mix the active ingredient with insoluble and/or slowly soluble polymer and excipients such as fillers, binders, glidants, lubricants, colorants, etc. Wet- or dry-granulate the mixture. Wet granulated material may be formed into spheres or spheroids via spheronization techniques readily known to the skilled artisan. Particles may also be generated by melt-extrusion process.

3. Matrix Capsules:

Mix the active ingredient with insoluble and/or slowly soluble polymer and excipients such as fillers, binders, glidants, lubricants, colorants, etc. If necessary, granulate the mixture. If granulated, the granules can be mixed with additional active ingredients and/or excipients and encapsulated. The capsules are called matrix-controlled release rate capsules. The capsules may be coated with an active ingredient, to provide an immediate release portion.

4. Membrane Coated Particles, Mini Tablets, Tablets or Capsules:

Immediate release or matrix solids (including but not limited to: particles, beads, granules, pellets, mini-tablets, tablets, capsules, and the like) can be coated with one or more release rate controlling polymers using processes known in the art, such as by compression coating, air bed coating, pan coating, and the like.

The above-described first release rate controlling polymer coating used for coating immediate release tablets provides a membrane-controlled release rate dosage form. A release rate controlling polymer coating of matrix tablets provides a matrix-membrane-controlled release rate dosage form. One or more release rate controlling polymers may further be formulated to contain excipients, such as pore formers and the like, using materials and processes readily known to the skilled artisan. Additionally, active ingredients may be incorporated into the polymer itself, and/or coated on top of the release rate controlling polymer, to provide an immediate release portion.

Part B: Detailed Procedure
1. Set up screening equipment with 16 mesh screen
2. Screen the ingredients
3. Visually re-inspect the screens for foreign material
4. Blend for 10 min
5. Screen the blended material, inspect the screen
6. Set up press with 0.75" round tooling
7. Compress the entire powder blend into slugged tablets with a hardness of 5-10 Kp (kilopascal)
8. Screen the slugs through a 16 mesh screen
9. Blend the granules with SSF (sodium stearyl fumarate) and CSD (colloidal silicon dioxide)
10. Pass through 14 mesh screen
11. Compress the granules using 4 mm round tooling to 50 mg target weight, hardness 7-11 Kp
12. Preparation of coating dispersion
    a. Heat water to 40-60 C
    b. Add HPMC (hydroxypropylmethyl cellulose), mix rigorously
    c. Continue mixing while allowing to cool
    d. Once a clear solution is obtained, while mixing, add polysorbate, talc
    e. Screen Eudraguard control through 60-mesh screen and add
    f. Continue mixing for another 30 min.
13. Calibrate the pump to deliver 30 g/min of the coating mixture
14. Load the core tablets into the coating pan, rotate the pan at 8-14 RPM (revolutions per minute)
15. Turn on the coating pan blower, exhaust air to 35 CFM (cubic feet per minute)
16. Turn on heat, set outlet temp to 33 C
17. Turn on and set atomization pressure to 40 psi, pattern air pressure to 40 psi (pounds per square inch)
18. Obtain weight of composite of 50 minitablets
19. Start spray when exhaust temperature is between 28-32 C
20. Increase spray rate to 25 g/min, maintain product temperature to 25-35 C
21. Continue spraying, periodically recording parameters and determining tablet weight gain until 8% weight gain is achieved.
22. Turn off the heat and let tablets tumble cool for 5 min
23. Remove required weight of tablets from coating pan, label as coating level 1
24. Repeat the coating operation until total 9.5% weight gain is achieved
25. Cure the coated mini-tablets for 5 h at 60 C
26. Place 1 mini-tablet of coating level 1 and 3 mini-tablets of coating level 2 in capsules
27. Place 210 capsules in bottles, add desiccant, induction seal and label the bottles Example 2: In Vitro Demonstration of Sustained Release Sustained release profiles of certain embodiments of the dosage forms as shown and described herein can be demonstrated and optimized, by a skilled artisan, using one or more of a variety of dissolution apparatus. For example, one may use one or more dissolution apparatus listed in the United States Pharmacopeia (USP), European pharmacopeia (EP), Japanese pharmacopeia (JP), or, by using other experimental techniques, such as ProDigest SHIME®, TNO's TIM-1 or TIM-2, Pion, Inc. μFLUX™, MacroFLUX™ or inFORM™, or similar techniques, which are readily known to a person of skill in the art.

Example 3: Development Data Summary for Sustained Release EGCG

Purified EGCG (>98% purity on an anhydrous basis) was evaluated for flow properties alone and in combination with other excipients. The mixture was blended with glidants and lubricants and compacted. Poor flow properties of blends containing as low as 25% EGCG were improved by dry granulation, accomplished by slugging and milling. The granules were compacted into 600 mg oblong tablets, containing 150 mg of EGCG. Dissolution from the immediate release tablets was characterized using a USP Dissolution Apparatus 2 (General Chapter <711> Dissolution, © *The United States Pharmacopeial Convention*, Dec. 1, 2011, page 2). The immediate release tablets were coated using perforated coating pan. Tablets coated to different coating level (characterized by % weight gain) were evaluated for rate of release of EGCG. See FIG. 1.

The % EGCG was further doubled and blend formulated was optimized to provide adequate flow for dry granulation. The granules were compressed into 300 mg round tablets, containing 150 mg EGCG, 50 mg round 4 mm mini-tablets containing 25 mg EGCG and 35 mg round 4 mm mini-tablets containing 17.5 mg EGCG. The immediate release tablets and mini-tablets were coated using perforated coating pan and evaluated for rate of release of EGCG.

Figure 4:
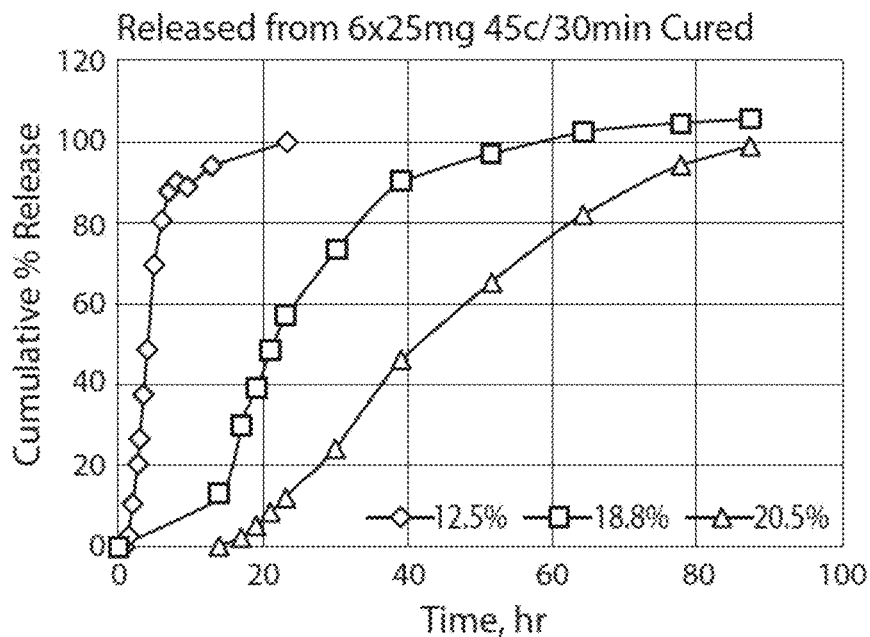
FIG. 4 shows the cumulative release of EGCG from mini-tablets coated to different levels of release rate modifying polymer (noted as % weight gain). An increase in % weight gain resulted in a corresponding decrease in the rate at which EGCG was released. See Example 16.

The dissolution data shown and described herein, demonstrates increases in lag time and duration of release with increases in the coating level. Combination of mini-tablets coated to different levels provided the desired continuous release of EGCG, as shown and described herein. See FIG. 4.

Example 4: ProDigest Model

In order to determine the fate of EGCG during passage through the human gastrointestinal tract (GIT), a sophisticated model of human GIT, M-SHIME®, was utilized (ProDigest, Ghent, Belgium).

The SHIME® is a unique scientifically validated dynamic model of the complete gastrointestinal tract to study physicochemical, enzymatic and microbial parameters in the gastrointestinal tract in a controlled in vitro setting. The model consists of five reactors which sequentially simulate the stomach (acid conditions and pepsin digestion), small intestine (digestive processes) and the 3 regions of the large intestine, i.e. the ascending, transverse and descending colon (microbial processes). Careful control of the environmental parameters in these reactors allows to obtain complex and stable microbial communities which are highly similar in both structure and function to the microbial community in the different regions of the human colon. The model can be used to study the metabolic fate of food, microbial and pharmaceuticals compounds over a period of several weeks.

Intestinal bacteria are largely present in the intestinal lumen, yet a fraction of the microorganisms in the gastrointestinal tract can also selectively adhere to the mucus layer that covers the gut wall. To evaluate this fraction of bacteria, which are supposed to have a key role in human health as they live in very close contact with the host, ProDigest makes use of the of the M-SHIME® (Mucus-SHIME). In this model, a mucosal compartment is integrated in the colonic regions of the SHIME®, allowing the microbiota to adhere to the gut mucus layer under representative conditions.

Two dosing strategies were studied:

Immediate release—A 150 mg dose of EGCG was administered to the M-SHIME-stomach compartment at the onset of the incubations and its stability was tested during passage through the upper GIT under both fed and fasted conditions.

Sustained release—A 150 mg dose of EGCG was introduced in aliquots over a 24 h-period at intervals coinciding with progression times through the M-SHIME-GIT compartments. The sustained release experiments were performed under fed conditions only.

Figure 3:
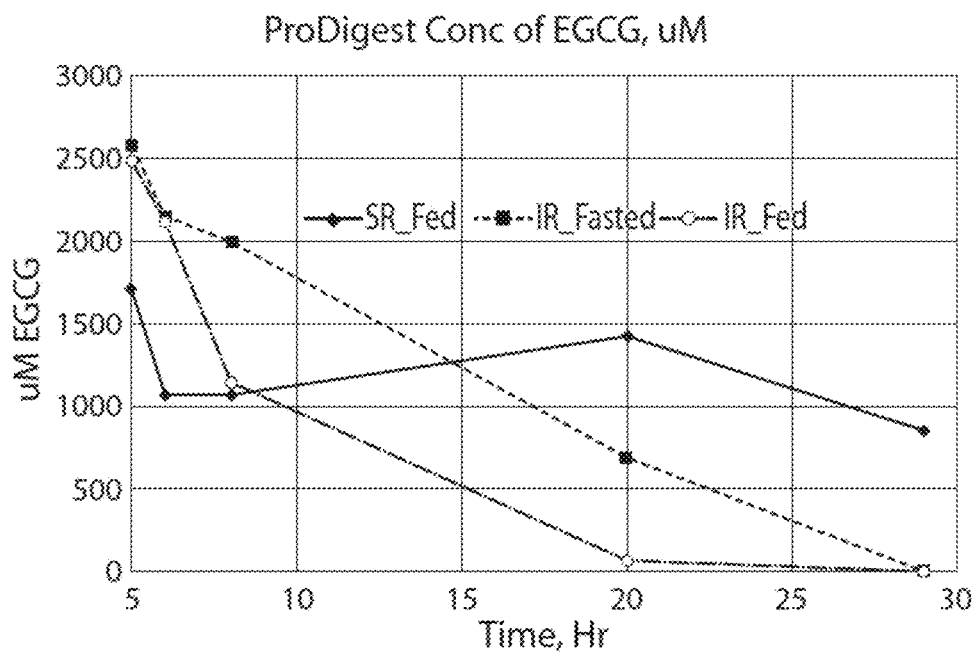
FIG. 3 depicts results of the ProDigest model of EGCG passage through the human gastrointestinal tract.

FIG. 3 shows EGCG concentration in the M-SHIME-colon compartment under the different conditions. The line with square-shaped symbols shows EGCG concentration in the M-SHIME-colon compartment under fasted conditions—the EGCG concentration appears to decrease linearly over approximately 29 hours, indicating the fate of EGCG, taken on a simulated empty stomach. The line with circular symbols shows the fate of EGCG taken on a simulated fed-stomach—there is much faster decline in EGCG concentration in the M-SHIME-colon compartment over approximately 20 hours. The line with diamond-shaped symbols shows that simulated administration of sustained release EGCG results in maintaining a constant EGCG concentration in the live colonic culture of human fecal matter in the M-SHIME-colonic compartment for longer. The conclusion is the sustained release approach will result in higher doses of EGCG being delivered and maintained in the colon.

Example 5: ThT Assay

A compound that inhibits, or that may inhibit, amyloidogenesis is combined with a bacterial amyloid initiator (e.g., *E. coli* CsgA), or a host-derived amyloidogenic protein (e.g., α-synuclein) and an amyloid precursor in the presence of Thioflavin T (ThT). Separately, as a control, bacterial amyloid initiator, amyloid precursor, and Thioflavin T are combined in the absence of the suspected amyloidogenesis inhibitor. Thioflavin T fluorescence is monitored over time. A reduction in the rate of increase in ThioflavinT fluorescence, and/or a reduction in the maximum level of Thioflavin T fluorescence in the sample containing the suspected inhibitor, relative to the control sample, confirms that the suspected amyloidogenesis inhibitor is in fact functioning to inhibit amyloid formation. The Tht assay was used with a cell-free assay to assess the effects of compounds on aggregation of α-synuclein of *E. coli* CsgA, and to assess the effects of compounds on aggregation of α-synuclein seeded by *E. coli* CsgA. For a detailed description of the ThT assay, see, e.g., International Publication No. WO/2018/213204, which is incorporated by reference herein in its entirety.

ThT Assay Results

| | | Inhibition of Aggregation | | |
| Compound | Structure | αSyn | CsgA-seeded αSyn | CsgA |
| --- | --- | --- | --- | --- |
| EGCG | 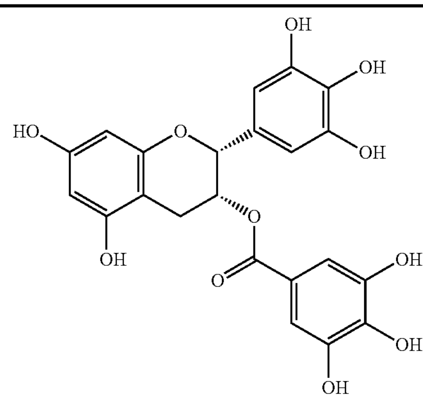 | +++ | +++ | ++ |
| quercetin | 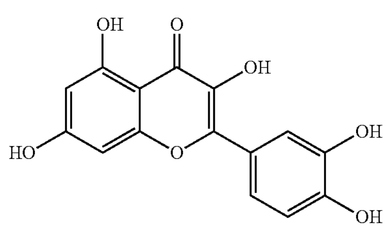 [SMILES: O=c1c(O)c(-c2ccc(O)c(O)c2)oc2cc(O)cc(O)c12] | +++ | | ++ |
| morin | 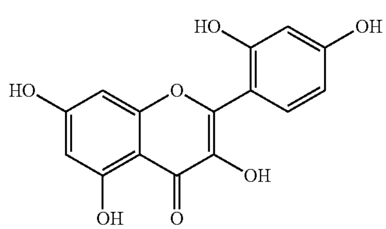 [SMILES: O=c1c(O)c(-c2ccc(O)cc2O)oc2cc(O)cc(O)c12] | +++ | +++ | +++ |

-continued

| Compound | Structure | Inhibition of Aggregation | | |
|---|---|---|---|---|
| | | αSyn | CsgA-seeded αSyn | CsgA |
| rosmarinic acid | 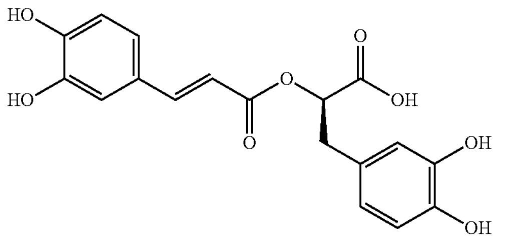 [SMILES: O=C(/C=C/c1ccc(O)c(O)c1)O[C@H](Cc1ccc(O)c(O)c1)C(=O)O] | +++ | | ++ |
| gallic acid | 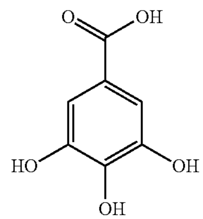 [SMILES: O=C(O)c1cc(O)c(O)c(O)c1] | +++ | +++ | +++ |
| methoxy-hydroquinone | 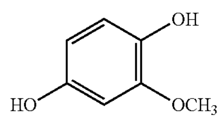 | +++ | +++ | ++ |
| curcumin | 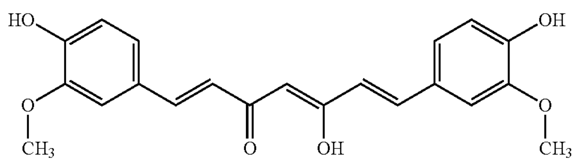 [SMILES: COc1cc(/C=C/C(=O)/C=C(O)/C=C/c2ccc(O)c(OC)c2)ccc1O] | +++ | +++ | |
| resveratrol | 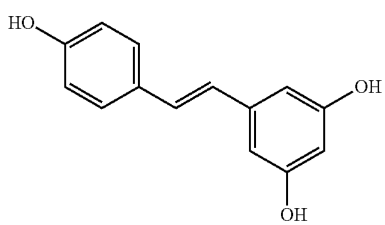 [SMILES: Oc1ccc(/C=C/c2cc(O)cc(O)c2)cc1] | +++ | | +++ |
| apigenin | 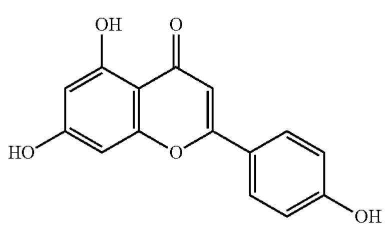 [SMILES: O=c1cc(-c2ccc(O)cc2)oc2cc(O)cc(O)c12] | ++ | | |
| NDGA | 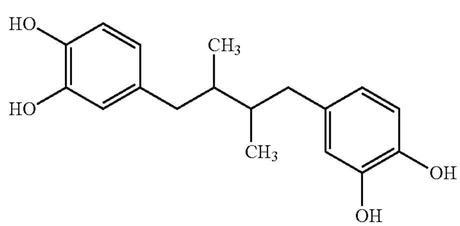 [SMILES: CC(Cc1ccc(O)c(O)c1)C(C)Cc1ccc(O)c(O)c1] | ++ | ++ | + |

-continued

| Compound | Structure | Inhibition of Aggregation | | |
|---|---|---|---|---|
| | | αSyn | CsgA-seeded αSyn | CsgA |
| phloretin | 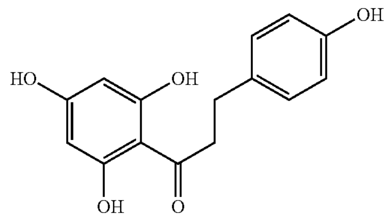 [SMILES: O=C(CCc1ccc(O)cc1)c1c(O)cc(O)cc1O] | ++ | + | + |
| genistein | 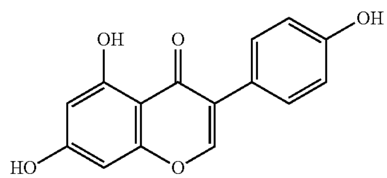 [SMILES: O=c1c(-c2ccc(O)cc2)coc2cc(O)cc(O)c12] | ++ | | |
| lauryl gallate | 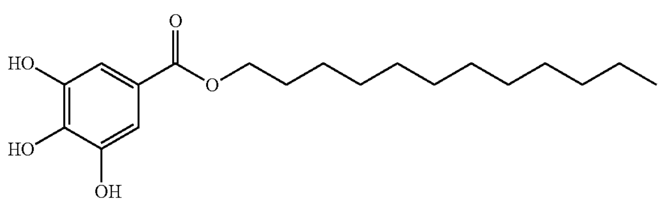 [SMILES: CCCCCCCCCCCCOC(=O)c1cc(O)c(O)c(O)c1] | ++ | + | − |
| isoeugenol | 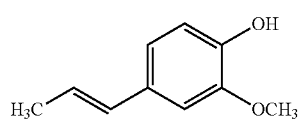 | − | ++ | − |
| 4-allyl-1,2-dimethoxy-benzene | 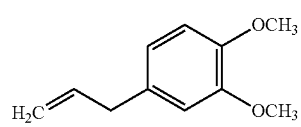 | − | ++ | −− |
| eugenol | 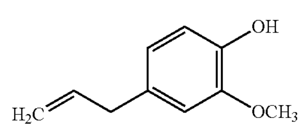 | − | ++ | − |
| 4-ethyl guaiacol | 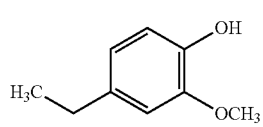 | − | −− | −− |
| guaiacol | 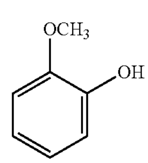 | − | ++ | − |

| Compound | Structure | Inhibition of Aggregation | | |
|---|---|---|---|---|
| | | αSyn | CsgA-seeded αSyn | CsgA |
| Anle 138b | 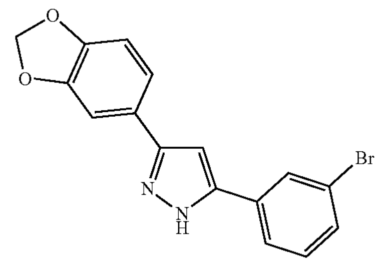 [SMILES: Brc1cccc(-c2cc(-c3ccc4c(c3)OCO4)n[nH]2)c1] | − | − | − |
| carvacrol | 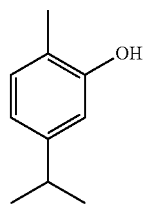 | − | − | −− |
| thymol | 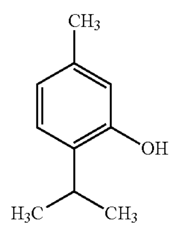 | −− | − | − |

Compound activity ranges presented are defined as follows: (−−) is less than −10% inhibition; (−) is between −10% to 10% inhibition; (+) is between 10% to 30% inhibition; (++) is between 30% to 60% inhibition; and (+++) is greater than 60% inhibition.

Inhibition by these compounds of aggregation of α-synuclein on its own could be independently beneficial or may be synergistic with their inhibition of microbial amyloid-seeded α-synuclein aggregation. In keeping with Braak's hypothesis of prion-like propagation of α-synuclein from the enteric nervous system to the central nervous system (see, e.g., Rietdijk et al., "Exploring Braak's Hypothesis of Parkinson's Disease," Front. Neurol., 13 Feb. 2017), these inhibitory effects could be beneficial in preventing propagation of α-synuclein aggregates in both the enteric and central nervous systems; furthermore, if orally administered compounds alleviate a continual seeding of α-synuclein aggregation by microbial amyloids or independent formation of α-synuclein aggregates, the processes by which subjects may clear α-synuclein aggregates may be able to have a greater net effect (i.e., the process may be able to keep pace with the aggregates formed), and the compounds may thereby be efficacious in preventing or treating Parkinson's Disease and other microbial amyloid-seeded α-synucleinopathies.

Example 6: In Vivo Treatment with EGCG Inhibits αSyn Amyloid Formation

It has been shown that in vivo treatment with EGCG inhibits or reduces αSyn amyloid formation in mice. Administration of EGCG improved motor scores, consistent with inhibition, amelioration, and alleviation of symptoms of aggregate-related diseases such as parkinsonism in accordance with some embodiments herein. See, e.g., International Publication No. WO/2018/213204, which is incorporated by reference herein in its entirety.

Example 7: Mono-Colonization of Mice with Curli-Sufficient Bacteria

It has been shown that mono-colonization of mice with curli-sufficient bacteria induces increased αSyn-dependent pathology and inflammatory responses in the brain. It has been observed that the presence or elevated levels (compared to healthy controls) of bacterial proteins such as CsgA in the gut is correlated with amyloid disorders, including Parkinson's Disease (PD). See, e.g., International Publication No. WO/2018/213204, which is incorporated by reference herein in its entirety.

Example 8: Intestinal Curli Promotes Progressive Synuclein-Dependent Pathophysiology It has been shown that intestinal curli promotes progressive synuclein-dependent pathophysiology in mice. Specifically, intestinal curli increased time to cross, time to descend, time to remove, and hindlimb score, and decreased time to fall and fecal pellets per mouse. The increases in time to cross, time to descend, and hindlimb score, and decrease in fecal pellets per mouse were statistically significant at the noted levels. See, e.g., International Publication No. WO/2018/213204, which is incorporated by reference herein in its entirety.

Example 9: Inhibition of Functional Amyloid Formation Dampens Progressive Motor Deficits It has been shown that inhibition of functional amyloid formation in accordance with some embodiments herein dampens progressive motor deficits. Without being limited by theory, it is contemplated that curli produced by E. coli utilize an amyloid-dependent pathway to exacerbate hallmark motor deficits and pathologies of PD in this preclinical model. It is further contemplated that inhibition of bacterial amyloid production, formation and/or interaction with mammalian amyloids in accordance with some embodiments herein is a useful intervention of neurodegenerative conditions caused by protein aggregation, for example amyloid disorders as described herein. See, e.g., International Publication No. WO/2018/213204, which is incorporated by reference herein in its entirety.

Example 10: Effects of CsgA on Seeding of αSyn Fibrilization

Effects of the bacterial amyloid protein, CsgA on the seeding of αSyn fibrilization have been studied. In vitro biophysical analysis was conducted with purified αSyn and CsgA proteins. It was tested whether the major curli subunit, CsgA, is capable of cross-seeding the formation of αSyn aggregations. It was observed that addition of purified CsgA to monomeric αSyn in vitro results in significantly accelerated production of αSyn aggregates. CsgA was also shown to seed synuclein propagation through transient interactions. See, e.g., International Publication No. WO/2018/213204, which is incorporated by reference herein in its entirety.

Example 11: Murine Models

The following two mouse models were used to evaluate the in vivo activity of test articles (i.e., sustained release solid dosage forms described herein).

Model 1 was performed in selected strains of specific pathogen free (SPF) mice (e.g. Swiss Webster) that carry curli producing bacteria as part of their native gastrointestinal microbiota.

Model 2 was performed in germ free mice that have no native microbiota. In these mice administration, by oral gavage, of a single strain of curli-producing bacteria (e.g. E. coli MC4100) led to stable bacterial colonization of their gastrointestinal tract. To prevent contamination by other environmental bacteria and to ensure stable mono-colonization with E. coli MC4100 these mice were maintained in sterile isolators throughout the course of our studies.

To evaluate the ability of test articles to modify bacterial curli levels in the gastrointestinal tract mice, from either Model 1 or 2, were treated with compound typically administered once daily via oral gavage. Treatment duration typically varied from 1 day through to multiple weeks depending on the specific objectives of each study. Where appropriate, test articles were evaluated at multiple dose levels, or at greater or lower dosing frequency. In some instances test articles were formulated into either the food or drinking water consumed by the animals.

To enable the quantitative assessment of test article impact on gastrointestinal curli levels, fecal samples were collected from these treated mice. Typically, this was done at regular intervals starting before compound treatment (the "baseline" sample) and then continuing throughout the course of the treatment period (e.g. at days 1, 3, 5, 7 and 14 days after commencing treatment). For fecal sample collection mice were placed singularly into clean 500 ml containers for 30 minutes, after which the mouse was returned to their home cage and all deposited fecal pellets recovered and immediately frozen. All fecal samples were stored at −80° C. until further analysis.

Assessment of curli content in feces was achieved through one of four approaches:
1. Quantitative measurement of messenger RNA (mRNA) levels for csgA using a specific qRT-PCR approach.
2. Quantitative measurement of curli protein levels using fluorescent dyes that bind to amyloid proteins (e.g. ThT, Congo Red, FSB).
3. Quantitate measurement of CsgA protein using ELISA or Western blot assays that leverage antibodies specific to CsgA or CsgA peptides.
4. Quantitate measurement of curli protein using mass spectrometry approaches that leverage peptide fragment signatures specific to curli protein.

Using these mouse models and curli quantification strategies the in vivo activity of EGCG and other test articles have been confirmed through their ability to reduce fecal levels of csgA mRNA, CsgA protein, and curli protein.

Example 12: Dog Studies

Procedure: 3 male and 3 female beagle dogs, 5-7 months of age, were acclimatized to the dosing facility. The animals were caged individually, fasted overnight and dosed with EGCG capsules. 30 min after dosing, the animals were allowed free access to food and water. Blood was collected predose, 30 min, 60 min, 90 min, 2, 4, 8, 16, 24, 36 and 48 h after dosing. Ascorbic acid was added to the plasma samples and stored at −70° C. prior to analysis.

Figure 5:
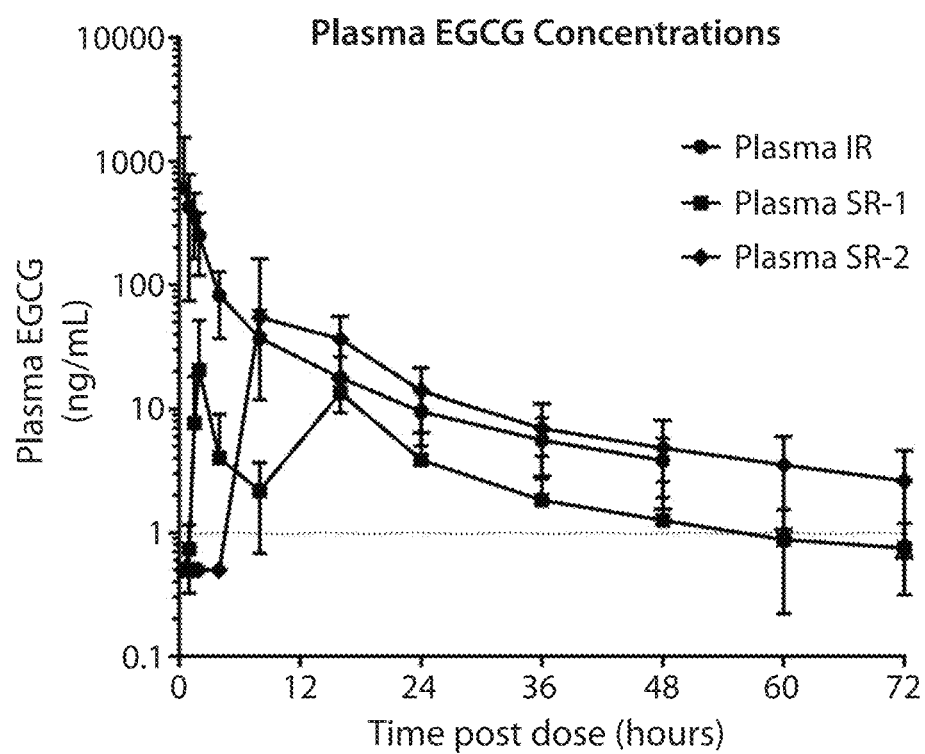
FIG. 5 shows plasma EGCG concentrations (mean±standard deviation) in beagle dogs dosed orally with EGCG in an immediate release formulation (IR, red circle) and two sustained release formulations (SR-1, green square & SR-2, blue triangle). Samples that were below the lower limit of quantification (LLOQ, 1 ng/mL, dotted line) were extrapolated to half the LLOQ for data analysis and graphing. The data shows that SR formulations provided lower peak plasma concentration ($C_{max}$) and lower actual plasma exposure (AUC) compared to the immediate release formulation.
Figure 6A:
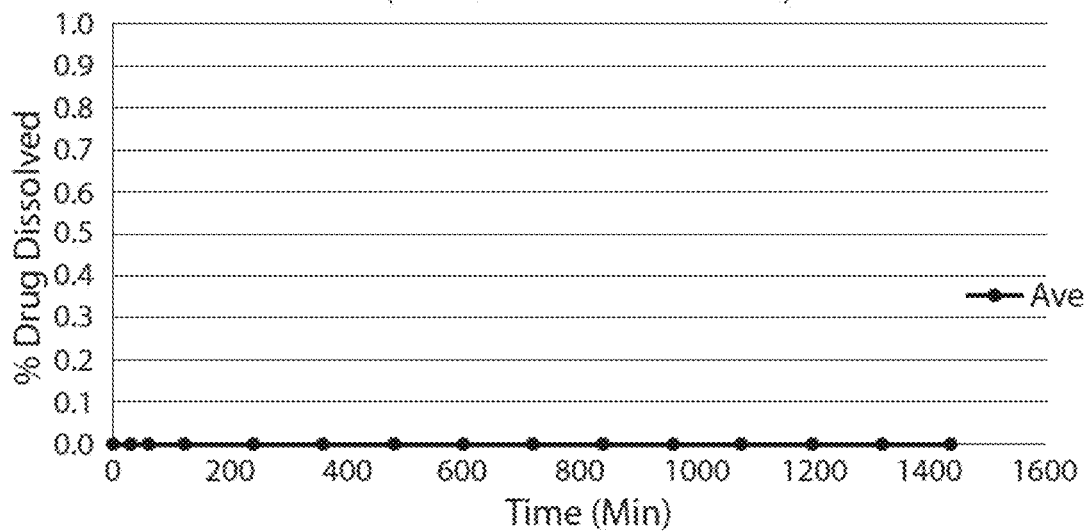
FIG. 6A-B depicts the dissolution of EGCG capsules.
Figure 6B:
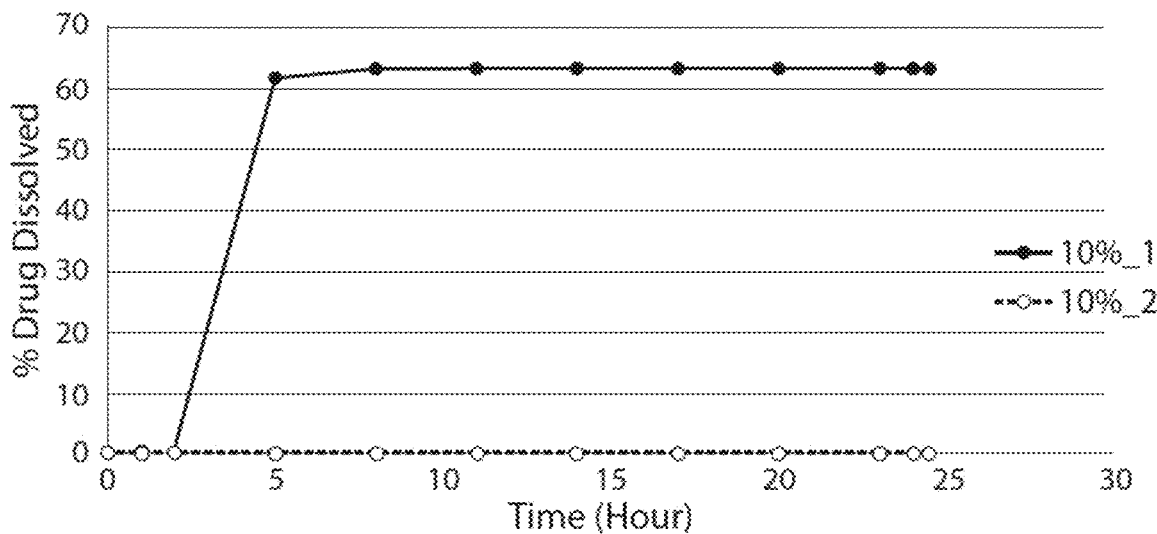

Results: In the dogs administered immediate release (IR) EGCG (EGCG in HPMC capsules), all plasma samples had quantifiable levels of EGCG. EGCG was initially detectable in the plasma after 30 min in 4/6 animals, after 1 hour in one animal, and after 1.5 hours in the 6th animal. For SR-1 (minitablets coated to 11.1% weight gain with polymethyl methacrylate formulation), three animals had no detectable EGCG and were excluded from the analysis. In the other 3 animals, EGCG was first detectable after 1, 1.5, and 16 hours. For SR-2 (minitablets coated to 7.3% weight gain with polymethyl methacrylate formulation), two animals had no detectable EGCG and were also omitted from the analysis. In the other 4 animals, EGCG was first detected after 8 hours in 1 animal, and 16 hours in the other 3 animals. FIG. 5 shows the mean plasma concentrations (±standard deviation) for EGCG in the three cohorts. Both SR formulations had lower peak plasma concentration ($C_{max}$), actual systemic exposure (AUC) values, and longer time to maximal plasma concentrations ($T_{max}$) vs IR. $C_{max}$ levels ranged from 830±809 ng/mL (mean±standard deviation; range 45-2280 ng/mL) for IR, 33±26 (range 5-56 ng/mL) for SR-1, and 84±91 (range 14-217 ng/mL) for SR-2. AUC levels ranged from 1641±984 ng*h/mL (range 315-3068 ng*h/mL) for IR, 162±160 (range 17-334 ng*h/mL) for SR-1, and 728±666 (range 142-1685 ng*h/mL) for SR-2. $T_{max}$ values ranged from 0.5 to 2.0 hours with IR, 2.0 to 16 hours with SR-1, and 8 to 16 hours with SR-2. While no published data on sustained release formulation of EGCG could be identified, these immediate release data are consistent with published data for EGCG in beagle dogs (Swezey 2003, Mata-Bilbao 2008).

Example 13: Exemplary Formulations (1)

Granulation Formula, Mg/Mini-Tablet

| Ingredient | mg/mini-tablet |
|---|---|
| EGCG | 25 |
| Microcrystalline cellulose | 11.92 |
| Mannitol | 11.93 |
| Sodium stearyl fumarate | 1 |
| Colloidal silicon dioxide | 0.15 |

Core Tablet Formula for Immediate Release Mini-Tablets/Tablets:

| Ingredient | mg/mini-tablet |
|---|---|
| Granules | 49 |
| Sodium stearyl fumarate | 0.5 |
| Colloidal silicon dioxide | 0.5 |

Coating: The formula used to develop the coating for mini-tablets (to obtain membrane-coated mini-tablets) was as follows.

| Ingredient | % |
|---|---|
| Eudragit ® (EUDRAGUARD ® control, Eudragit ® NE 30 D) Control | 45.5% |
| HPMC E-5 | 4.5% |
| Tween 80 | 4.5% |
| Talc | 45.5% |

Figure 7:
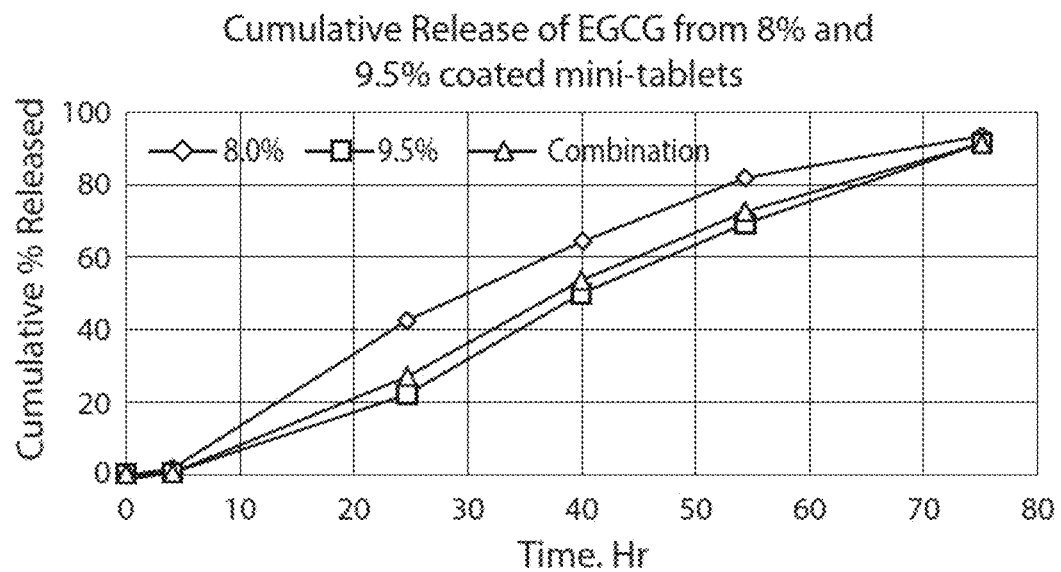
FIG. 7 depicts cumulative release of EGCG from 8% and 9.5% coated mini-tablets. See Example 15.
Figure 8:
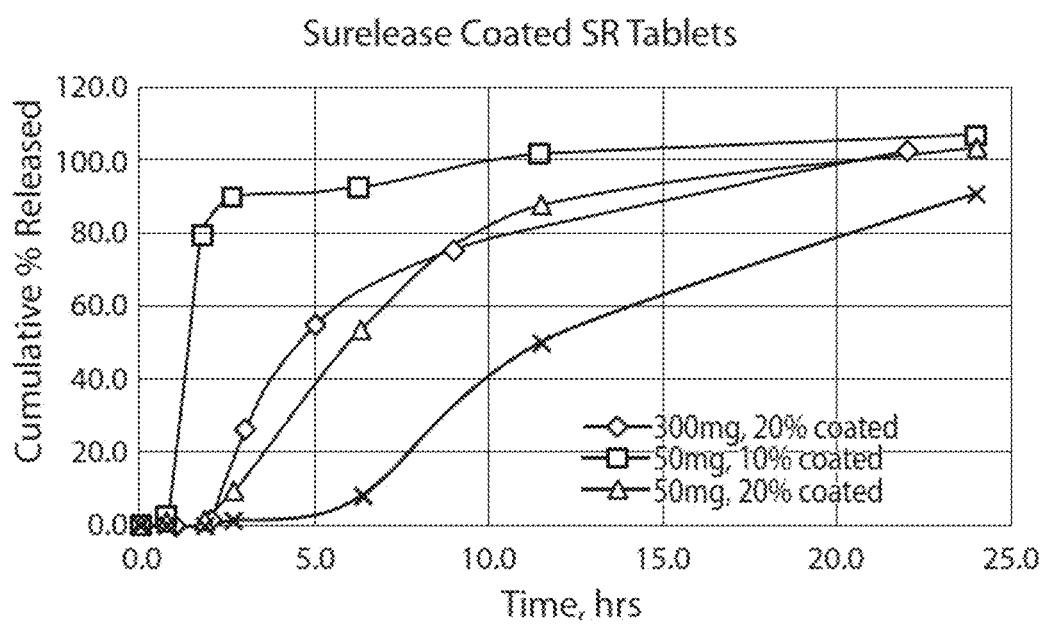
FIG. 8 depicts the dissolution of ethyl cellulose (Surelease) coated tablets. See Example 19.

The mini-tablets were coated to 8% and 9.5% weight gain. The coated tablets were cured at 60° C. for 4-5 h. The release profile from those tablets as well as projected release profile from utilizing 1 of 8% and 3 of 9.5% coated mini-tablets is shown in FIG. 7.

Immediate Release (IR) Formulation.

Figure 62:
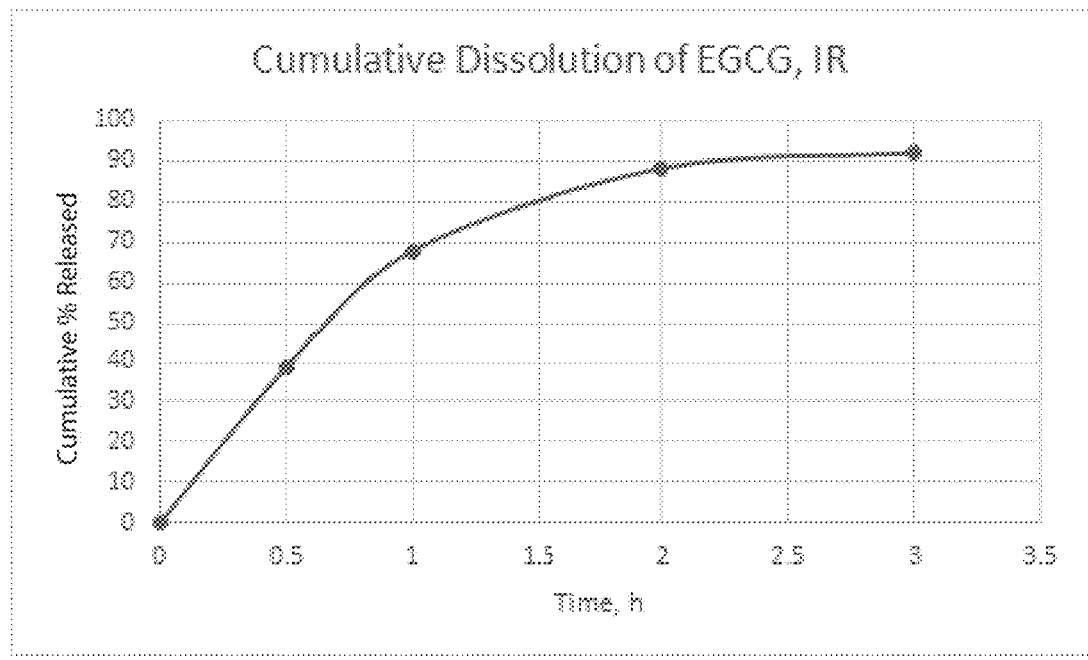
FIG. 62 depicts Cumulative Dissolution of an EGCG IR Formulation.

EGCG, 150 mg, was filled in HPMC capsules. One hundred and forty capsules were packaged per bottle. The dissolution testing was performed in USP apparatus 2 at 37 C in 0.1N HCl and sampled at 15 min intervals for 1 hr. Dissolution samples were analyzed by HPLC for EGCG concentration. Dissolution results are shown in FIG. 62.

Example 14: Exemplary Formulations (2)

Intragranular:

| Ingredient | weight |
|---|---|
| EGCG | 150 mg |
| Microcrystalline cellulose | 65.1 mg |
| Mannitol | 65.1 mg |
| Sodium stearyl fumarate | 6 mg |
| Fumed silica | 0.9 mg |

Extragranular:

| EGCG granules | 296.4 mg |
|---|---|
| Sodium stearyl fumarate | 3 mg |
| Fumed silica | 0.6 mg |

Coating Formula:

| Ingredient | % |
|---|---|
| Eudragit Control | 47.7225 |
| HPMC E-5 | 4.8405 |
| Polysorbate 80 | 4.7040 |
| Talc | 47.7225 |

The coating formulation was applied under the following parameters:

| Parameter | Setpoint |
|---|---|
| Pan speed | 35-45 Hz |
| Tablet temperature | 28-33 C. |
| Atomization SLPM (Standardized Liters Per Minute) | 100-150 |
| Pattern SLPM | 110 |
| Spray rate | 18 Hz |

Example 15: Exemplary Formulations (3)

Formulation A.

| Ingredient | mg/tablet |
|---|---|
| Active agent | 200 |
| Microcrystalline cellulose | 50 |
| Lactose | 100 |
| Sodium stearyl fumarate | 12 |
| Colloidal silicon dioxide | 1 |

Procedure: the material is dry-blended and compressed. The tablets are coated using formulation similar to the one outlined in Example 13.

Formulation B.

| Ingredient | mg/mini-tablet |
|---|---|
| Active agent | 12.5 |
| HPMC | 18.17 |
| Mannitol | 18.18 |
| Sodium stearyl fumarate | 1 |
| Colloidal silicon dioxide | 0.15 |

Procedure: The materials are blended and the mini-tablets are compressed as described in manufacturing example 1. The 4 mm mini-tablets are encapsulated and packaged.

Formulation C.

| Ingredient | mg/mini-tablet |
|---|---|
| Active agent | 3 |
| HPMC | 1 |
| Mannitol | 1 |

| Ingredient | mg/mini-tablet |
|---|---|
| Sodium stearyl fumarate | 0.15 |
| Colloidal silicon dioxide | 0.015 |

Screened EGCG or an aminosterol, HPMC, and mannitol are blended. The blend is loaded in high shear granulator and sprayed with water to about 12% weigh gain or until cohesive wet mass is obtained. The wet mass is passed through a 20 mesh screen and dried in a fluidized bed dryer to 3-5% moisture content. The dried granules are passed through a 40 mesh screen, blended with colloidal silicon dioxide and sodium stearyl fumarate and compressed into 2 mm mini-tablets. These are encapsulated and packaged.

Formulation D.

| Ingredient | mg/mini-tablet |
|---|---|
| Active agent | 3 |
| HPMC | 1 |
| Mannitol | 1 |
| Magnesium stearate | 0.05 |
| Colloidal silicon dioxide | 0.015 |

Screened EGCG or an aminosterol, HPMC, and mannitol are blended. The blend is loaded in high shear granulator and sprayed with water to about 12% weigh gain or until cohesive wet mass is obtained. The wet mass is passed through a 20 mesh screen and dried in a fluidized bed dryer to 3-5% moisture content. The dried granules are passed through a 40 mesh screen, blended with colloidal silicon dioxide and sodium stearyl fumarate and compressed into 2 mm mini-tablets. These are coated with Eudragit Control formula shown in example 1 to 10% weight gain. The coated minitablets are encapsulated and packaged.

Formulation E.

| Ingredient | mg/mini-tablet |
|---|---|
| Active agent | 3 |
| HPC | 1 |
| lactose | 1 |
| Stearic acid | 0.15 |
| Colloidal silicon dioxide | 0.015 |

Screened EGCG or an aminosterol, HPC (hydroxypropyl cellulose), and lactose are blended. The blend is loaded in high shear granulator and sprayed with Eudraguard Control to about 12% weigh gain or until cohesive wet mass is obtained. The wet mass is passed through a 20 mesh screen and dried in a fluidized bed dryer to 3-5% moisture content. The dried granules are passed through a 40 mesh screen, blended with colloidal silicon dioxide and sodium stearyl fumarate and compressed into 2 mm mini-tablets. These mini-tablets are cured at 60c for 5 h. The coated minitablets are encapsulated and packaged.

Formulation F.

| Ingredient | mg/bead |
|---|---|
| Active agent | 1 |
| HPMC | 0.2 |
| Microcrystalline cellulose | 0.2 |

| Ingredient | mg/bead |
|---|---|
| Sodium stearyl fumarate | 0.15 |
| Colloidal silicon dioxide | 0.015 |

Screened EGCG or an aminosterol, HPMC, and mannitol are blended. The blend is loaded in high shear granulator and sprayed with water to about 12% weigh gain or until cohesive wet mass is obtained. The wet mass is passed through an extruder with a 18 mesh screen, spheronized and dried. The dried beads are mixed with colloidal silicon dioxide and sodium stearyl fumarate, encapsulated and packaged.

Formulation G.

| Ingredient | % |
|---|---|
| Microcrystalline cellulose bead | 70 |
| Active agent | 29 |
| HPMC | 1 |

Solution of EGCG or an aminosterol and HPMC is sprayed on microcrystalline cellulose beads to 43% weight gain in a Wuster-coating type apparatus. The EGCG- or aminosterol-loaded beads are coated with Kollicoat SR 30 D latex to 20% weight gain and cured. The cured beads are encapsulated and packaged.

Example 16: Exemplary Formulations (4)

Formulation B1: Core Tablet Formula

| Ingredient | mg/tablet |
|---|---|
| EGCG | 100 |
| Lactose | 44 |
| HPMC E10M | 150 |
| Talc | 3 |
| Magnesium stearate | 3 |

Figure 10:
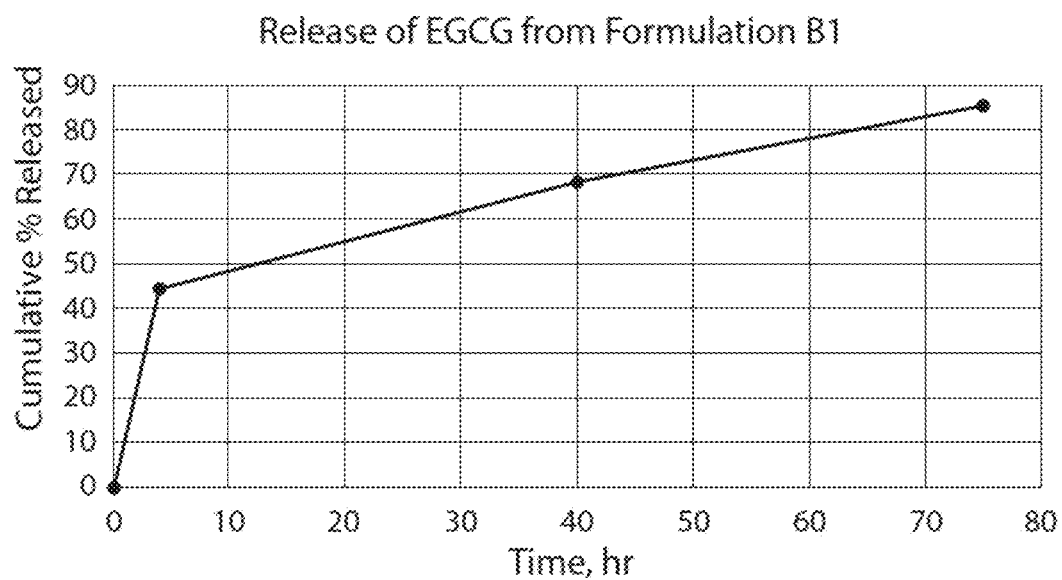
FIG. 10 depicts Release of EGCG from Formulation B1.

This is an example of a matrix-type sustained release formulation, made with a water soluble, swelling polymer (e.g., a water swelling polymer) (specifically, HPMC E10M). The powder blend was compressed to hardness between 10 and 15 Kg. The release profile from the tablets is shown in FIG. 10. The presence of highly soluble excipient, lactose, results in the initial rapid release (burst-release) from EGCG. Correspondingly, most of the tablet core was dissolved away at 75 h.

Formulation B2: Core Tablet Formula

| Ingredient | mg/tablet |
|---|---|
| EGCG | 150 |
| Carbopol 971P | 100 |
| Colloidal Silicon Dioxide | 3 |
| Magnesium stearate | 3 |

Figure 11:
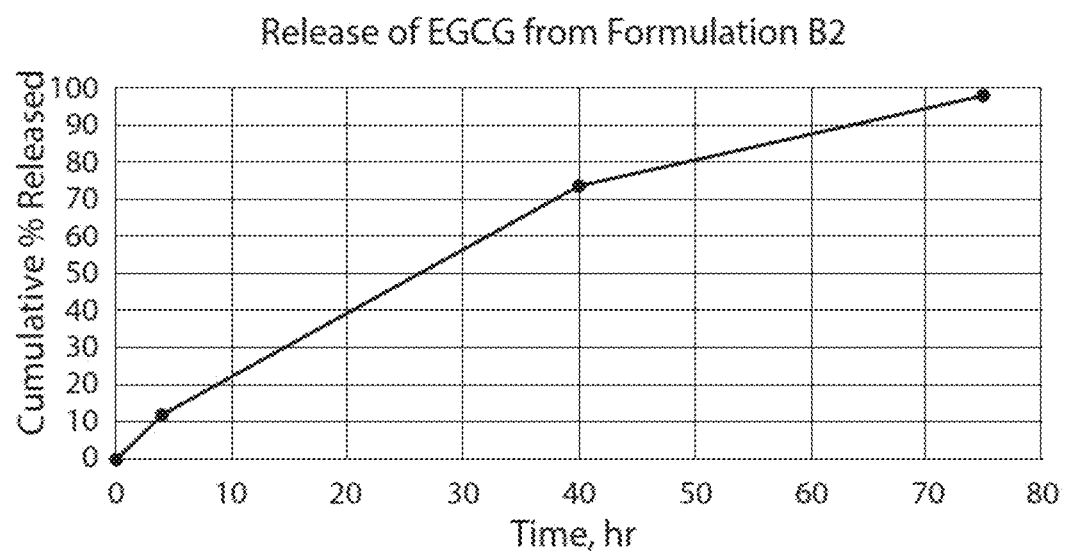
FIG. 11 depicts Release of EGCG from Formulation B2.

This is an example of a matrix-type sustained release formulation, made with water soluble, swelling polymer (e.g., a water swelling polymer) (specifically, Carbopol 971P). The powder blend was compressed to hardness between 10 and 15 Kg. The release profile from those tablets is shown in FIG. 11. In the absence of highly water-soluble excipient (lactose), no burst-release is seen, and the release is fairly linear. Carbopol swells quite a bit, allowing for ideal level of diffusion. At the end of dissolution, tablet cores were found as clear gelatinous blobs, about 4× the starting size.

Formulation B3: Core Tablet Formula

| Ingredient | mg/tablet |
| --- | --- |
| EGCG | 100 |
| PEO 600K | 100 |
| Colloidal Silicon Dioxide | 3 |
| Sodium stearyl fumarate | 6 |

Figure 12:
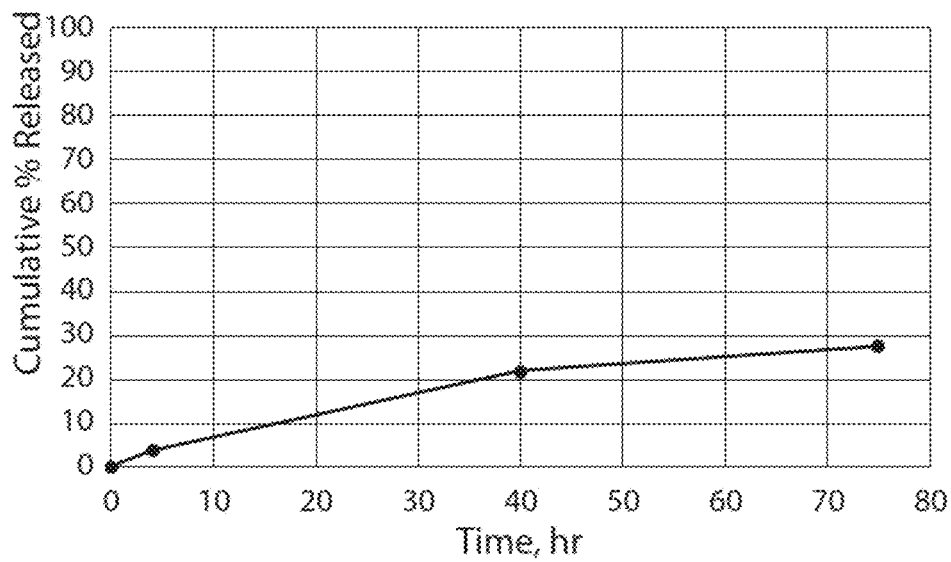
FIG. 12 depicts Release of EGCG from Formulation B3.

This is an example of a matrix-type sustained release formulation, made with water soluble, swelling polymer (e.g., a water swelling polymer) (specifically, PEO 600K). The powder blend was compressed to hardness between 10 and 15 Kg. The release profile from those tablets is shown in FIG. 12. PEO 600K provided a very strong resistance to water penetration. At the end of dissolution (75 h), the core tablets looked a little swollen but were entirely intact. As shown in FIG. 12, this resulted in much slower release from the tablets.

Formulation B4: Core Tablet Formula

| Ingredient | mg/tablet |
| --- | --- |
| EGCG | 50 |
| HPMC E10M | 200 |
| Talc | 3 |
| Magnesium stearate | 3 |

Figure 13:
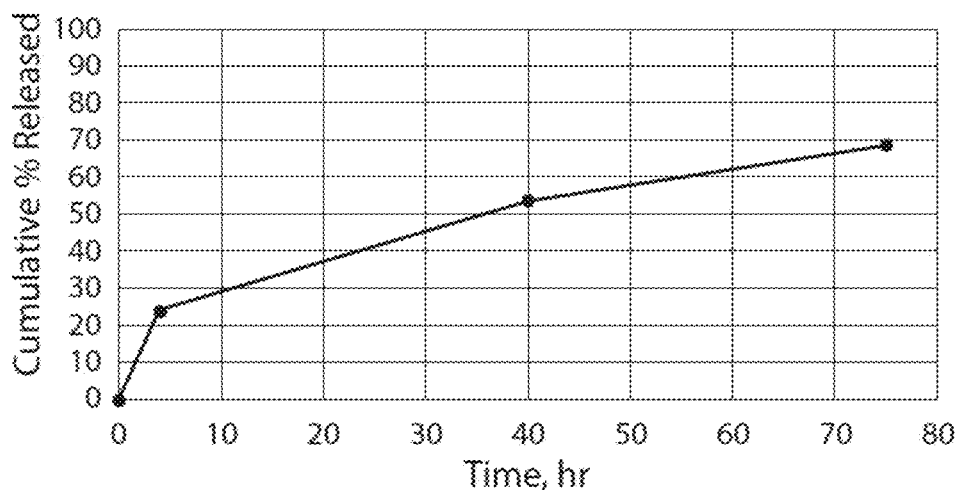
FIG. 13 depicts Release of EGCG from Formulation B4.

This is an example of a matrix-type sustained release formulation, made with water soluble, swelling polymer (e.g., a water swelling polymer) (specifically, HPMC E10M). The powder blend was compressed to hardness between 10 and 15 Kg. Compared to Formulation B1, the ratio of drug or water-soluble excipient (lactose) to polymer is lower. An increased proportion of polymer resulted in a core that didn't dissolve away at 75 h (was simply a little swollen/larger in size). Compared to Formulation B1, the burst-effect was also significantly reduced and overall, slower release rate was achieved (FIG. 13).

Formulation B5: Core Tablet Formula

| Ingredient | mg/tablet |
| --- | --- |
| EGCG | 50 |
| Carbopol 971P | 200 |
| Colloidal silicon dioxide | 3 |
| Magnesium stearate | 3 |

Figure 14:
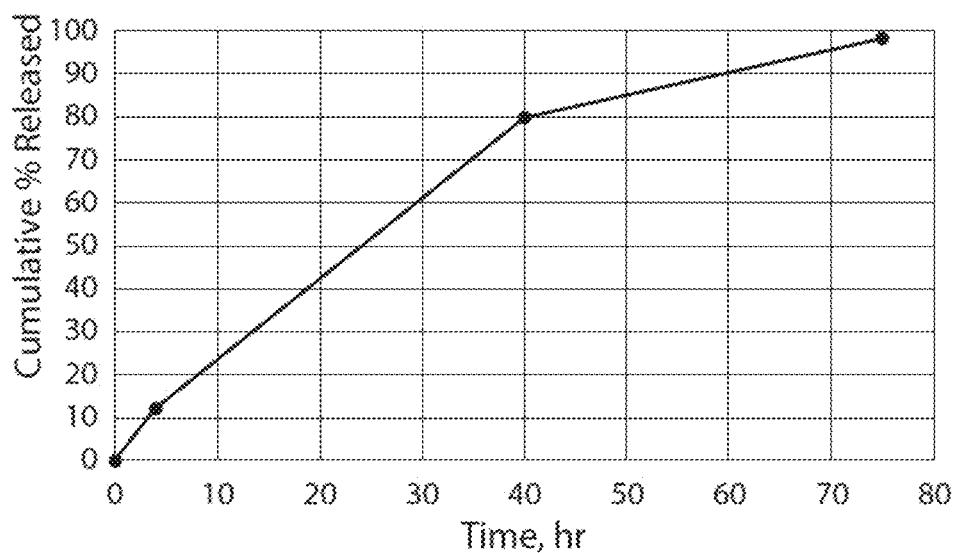
FIG. 14 depicts Release of EGCG from Formulation B5.

This is an example of a matrix-type sustained release formulation, made with water soluble, swelling polymer (e.g., a water swelling polymer) (specifically, Carbopol 971P). The powder blend was compressed to hardness between 10 and 15 Kg. Compared to Formulation B2, the ratio of drug or water-soluble excipient (lactose) to polymer is lower. This resulted in longer duration of release. At the end of dissolution, the observations were very similar to those for dissolution of Formulation B2 and release profiles were almost identical (FIG. 14).

Formulation B6: Core Tablet Formula

| Ingredient | mg/tablet |
| --- | --- |
| EGCG | 50 |
| PEO 600K | 200 |
| Colloidal silicon dioxide | 3 |
| Sodium Stearyl Fumarate | 6 |

Figure 15:
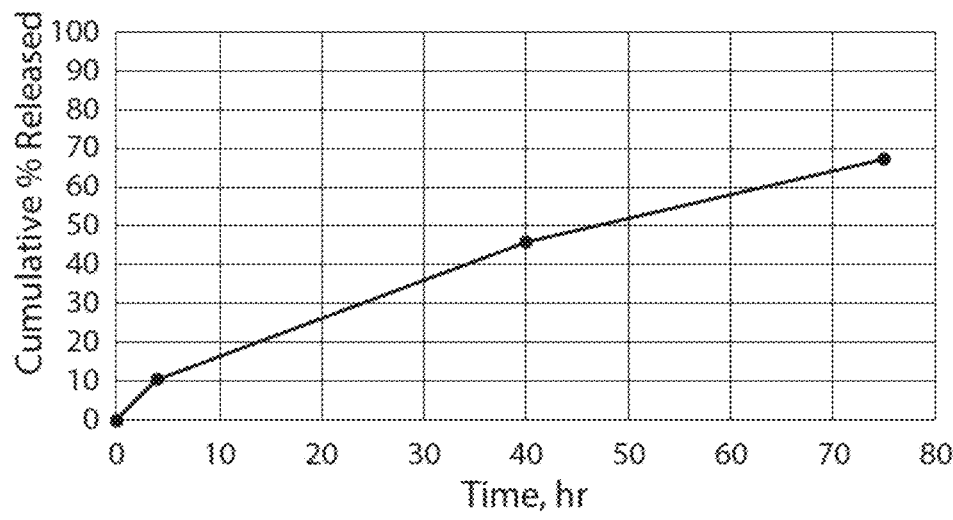
FIG. 15 depicts Release of EGCG from Formulation B6.

This is an example of a matrix-type sustained release formulation, made with water soluble, swelling polymer (e.g., a water swelling polymer) (specifically, PEO 600K). The powder blend was compressed to hardness between 10 and 15 Kg. At the end of dissolution, the tablet core was squishy and readily broke apart. The release profile from those tablets is shown in FIG. 15.

Formulation B7: Core Tablet Formula

| Ingredient | mg/tablet |
| --- | --- |
| EGCG | 200 |
| HPMC E10M | 100 |
| Colloidal silicon dioxide | 2 |
| Magnesium stearate | 3 |

Figure 16:
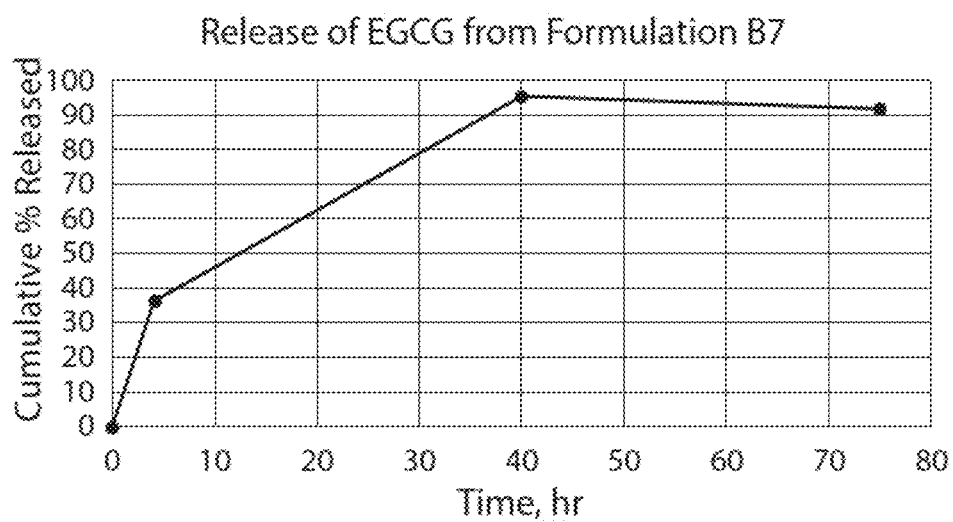
FIG. 16 depicts Release of EGCG from Formulation B7.

This is an example of a matrix-type sustained release formulation, made with water soluble, swelling polymer (e.g., a water swelling polymer) (specifically, HPMC E10M). The powder blend was compressed to hardness between 10 and 15 Kg. Compared to Formulations B1 and B4, the ratio of drug or water-soluble excipient (lactose) to polymer is high. This resulted in faster release. At the end of 75 h, the recovered swollen tablet matrix crushed easily. The release profile from those tablets is shown in FIG. 16.

Formulation B8: Core Tablet Formula

| Ingredient | mg/tablet |
| --- | --- |
| EGCG | 200 |
| Carbopol 971P | 100 |
| Talc | 3 |
| Magnesium stearate | 3 |

Figure 17:
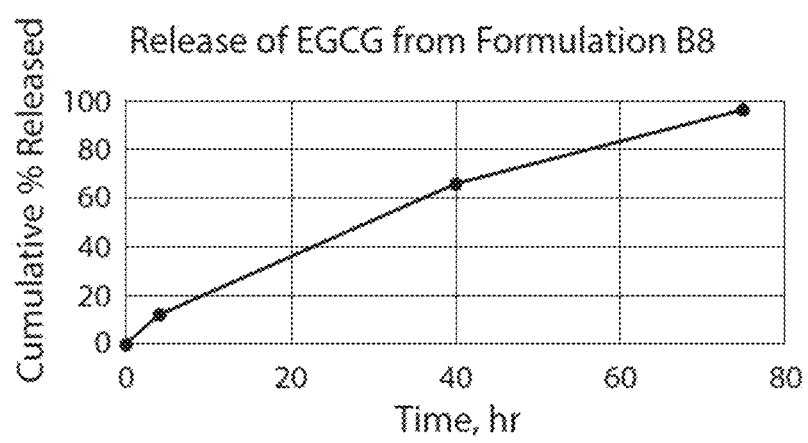
FIG. 17 depicts Release of EGCG from Formulation B8.

This is an example of a matrix-type sustained release formulation, made with water soluble, swelling polymer (e.g., a water swelling polymer) (in this case, Carbopol 971P). The powder blend was compressed to hardness between 10 and 15 Kg. At the end of dissolution, the swollen tablet cores looked like jelly blobs. The release profile from those tablets is shown in FIG. 17.

Formulation B9: Core Tablet Formula

| Ingredient | mg/tablet |
| --- | --- |
| EGCG | 200 |
| PEO 600K | 100 |
| Colloidal silicon dioxide | 2 |
| Sodium stearyl fumarate | 6 |

Figure 18:
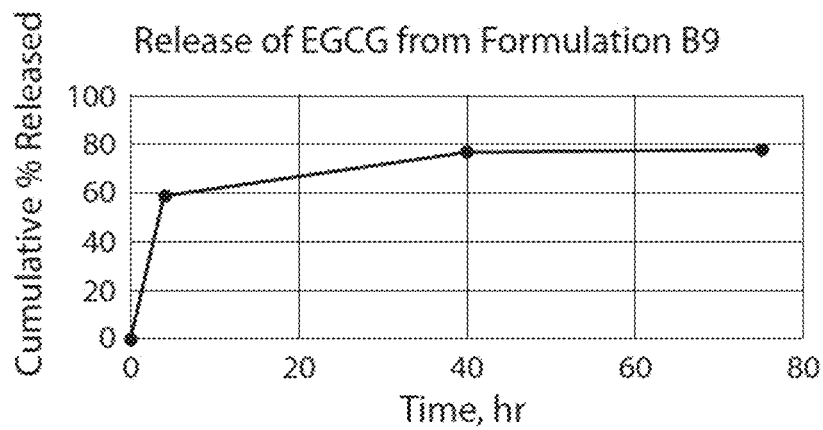
FIG. 18 depicts Release of EGCG from Formulation B9.

This is an example of a matrix-type sustained release formulation, made with water soluble, swelling polymer (e.g., a water swelling polymer) (in this case, PEO 600K). The powder blend was compressed to hardness between 10 and 15 Kg. Compared to Formulations B3 and B6, the ratio of drug or water-soluble excipient (lactose) to polymer is higher. The release profile shows fast initial release. At the end of dissolution, the core tablet broke apart easily. Release profile from those tablets is shown in FIG. 18.

Figure 19:
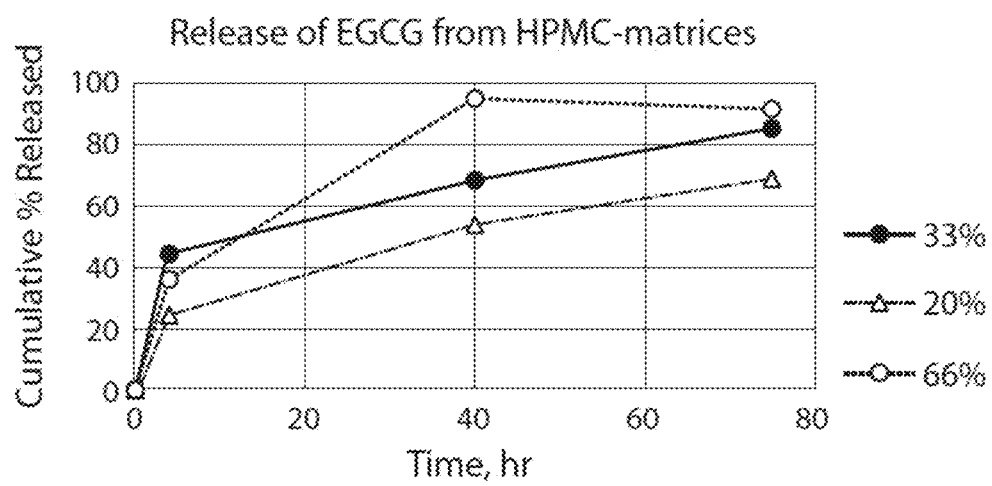
FIG. 19 depicts Release of EGCG from HPMC matrices.

Formulations from B1-B9 can also be consolidated by the polymer. Release profiles for Formulations (B1, B4, B7) containing HPMC E10M polymer are shown in graph "Release of EGCG from HPMC-Matrices" (FIG. 19). The graph shows initial fast release and then steady release, showing that formulation with 66% EGCG is more suitable for release over 40 h while decreasing proportion of EGCG (correspondingly, increasing proportion of polymer) allowed for EGCG release over a longer duration, with matrices containing lowest proportion of EGCG evaluated, 20%, providing longest duration of release.

Figure 20:
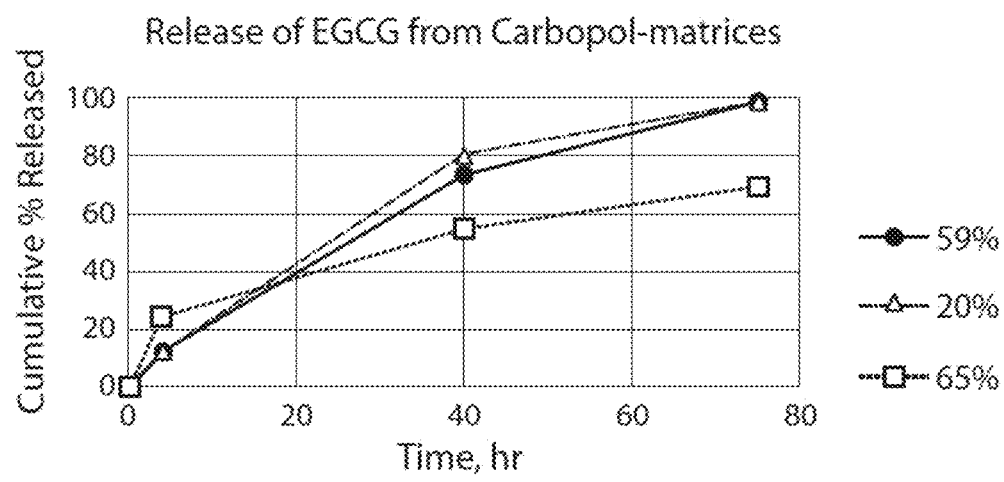
FIG. 20 depicts Release of EGCG from Carbopol matrices.

Release profiles for Formulations (B2, B5, B8) containing Carbopol 971P polymer are shown in graph "Release of EGCG from Carbopol-Matrices" (FIG. 20). The graph shows initial fast release for only the formulation containing 65% EGCG. Formulations containing 20% or 59% EGCG had near identical release profile, showing 100% release at the 75 h timepoint. Surprisingly, the formulation with 65% EGCG showed the slowest release after showing initial burst at 4 h time point.

Figure 21:
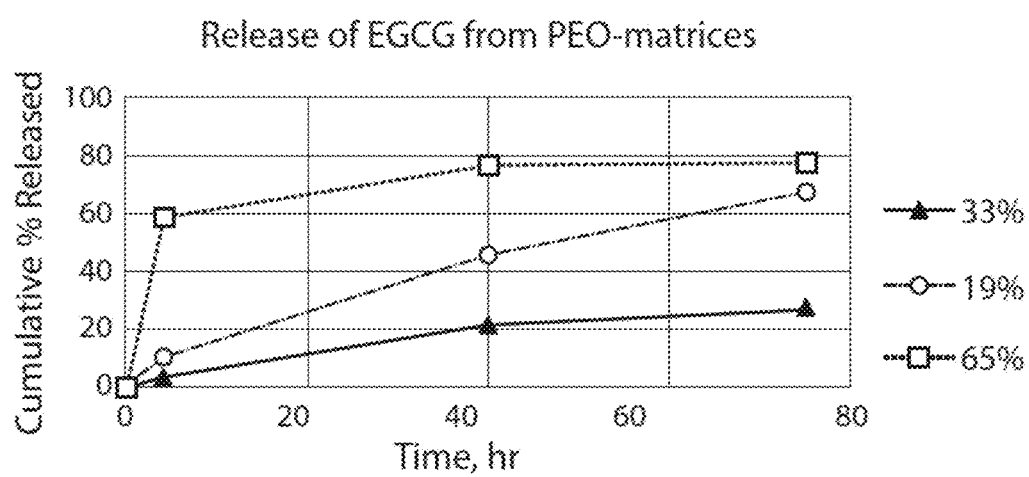
FIG. 21 depicts Release of EGCG from PEO (polyethylene oxide) matrices.

Release profiles for Formulations (B3, B6, B9) containing PEO polymer are shown in graph "Release of EGCG from PEO-Matrices" (FIG. 21). The graph shows initial fast release for only the formulation containing 65% EGCG. Despite fast initial release, this formulation, surprisingly, didn't release about 20% of EGCG till the 75 h timepoint. Formulations containing 19% or 33% EGCG showed linearly increasing release. Surprisingly, the formulation with 33% EGCG showed slower release than the formulation with 19% EGCG.

Example 17: Exemplary Formulations (5)

Formulation WI1: Core Tablet Formula

| Ingredient | mg/tablet |
| --- | --- |
| EGCG | 50 |
| Eudragit RS PO | 200 |
| Talc | 3 |
| Magnesium stearate | 3 |

Figure 22:
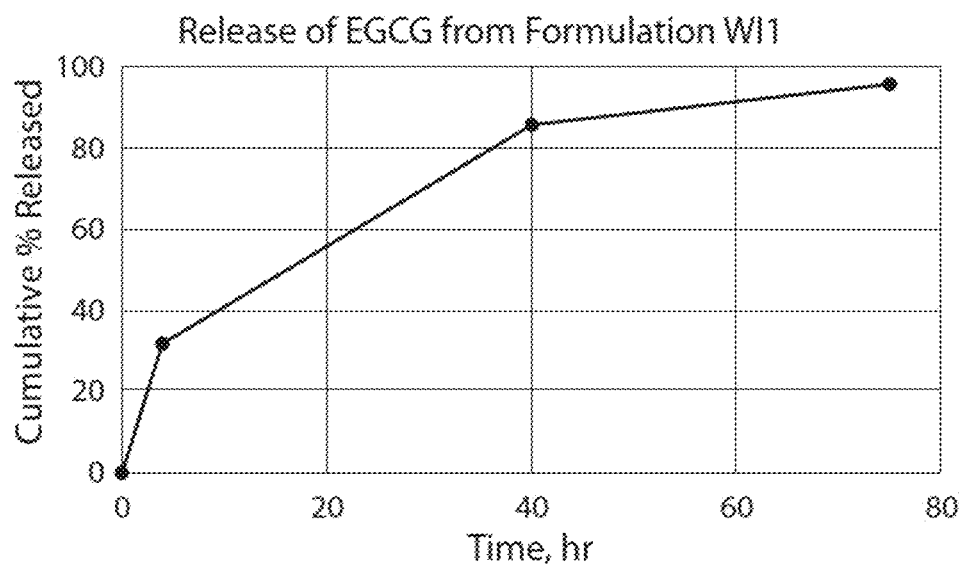
FIG. 22 depicts Release of EGCG from Formulation WI1.
Figure 23:
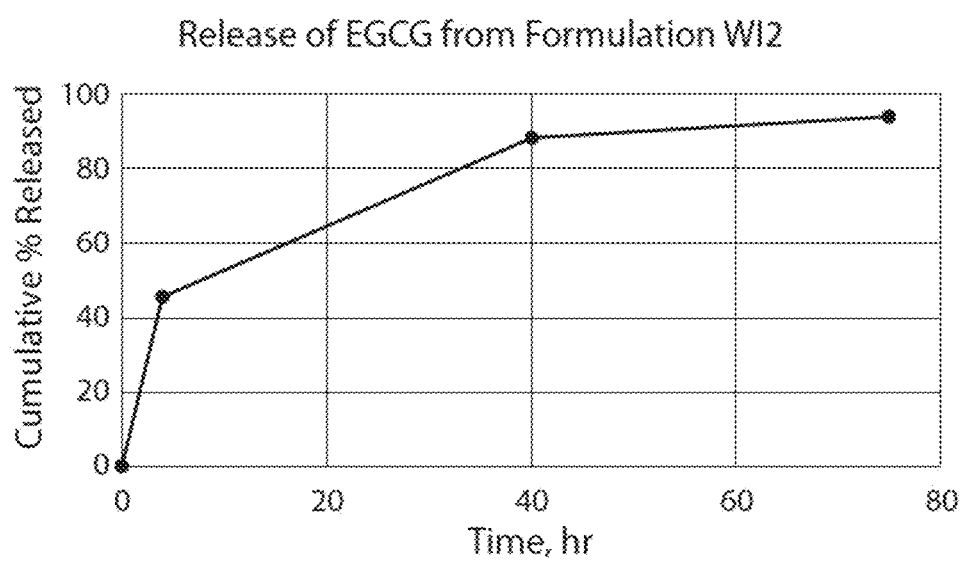
FIG. 23 depicts Release of EGCG from Formulation WI2.

This is an example of a matrix-type sustained release formulation, made with water insoluble polymer (in this case, Eudragit RS PO). The powder blend was compressed to hardness between 10 and 15 Kg. The release profile from those tablets is shown in FIG. 22. Due to the nature of the water insoluble polymer, at the end of 75 h dissolution, the tablets looked the same as before beginning of dissolution (no swelling). Release data shown in FIG. 22.

Formulation WI2: Core Tablet Formula

| Ingredient | mg/tablet |
| --- | --- |
| EGCG | 100 |
| Eudragit RL PO | 200 |
| Colloidal silicon dioxide | 3 |
| Magnesium stearate | 3 |

This is an example of a matrix-type sustained release formulation, made with water insoluble polymer (in this case, Eudragit RL PO). The powder blend was compressed to hardness between 10 and 15 Kg. Due to the nature of the water insoluble polymer, at the end of 75 h dissolution, the tablets looked the same as before beginning of dissolution (no swelling). The release profile from those tablets is shown in FIG. 39.

Formulation WI2 Sintered: Core Tablet Formula the Same as Formulation WI2.

Figure 24:
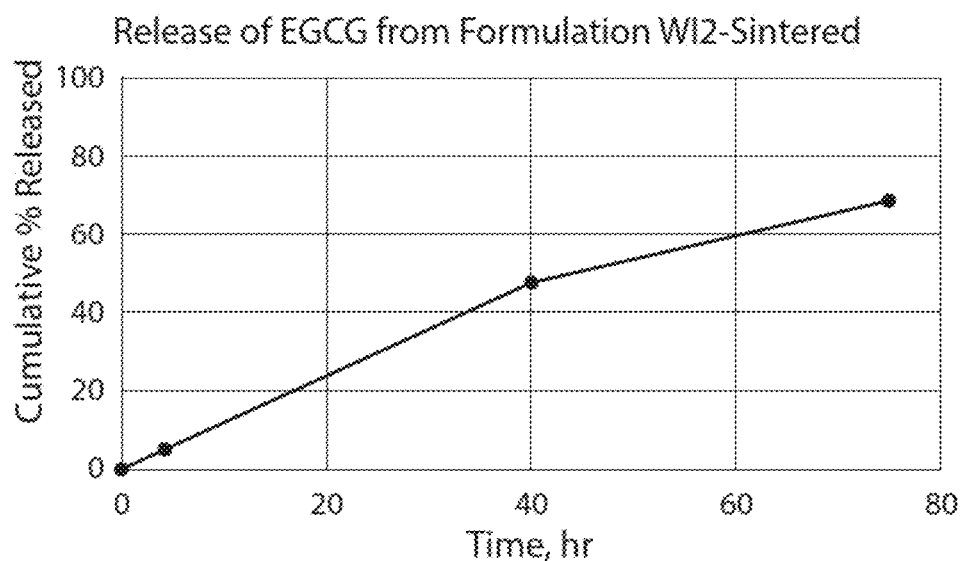
FIG. 24 depicts Release of EGCG from Formulation WI2-sintered.
Figure 25:
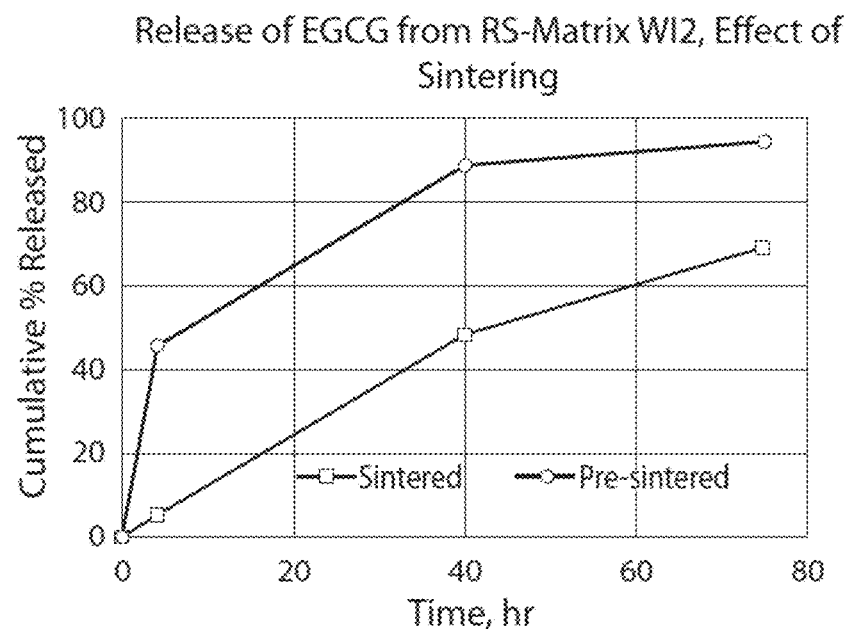
FIG. 25 depicts the Effect of Sintering on Release of EGCG from RS-Matrix WI2.
Figure 26:
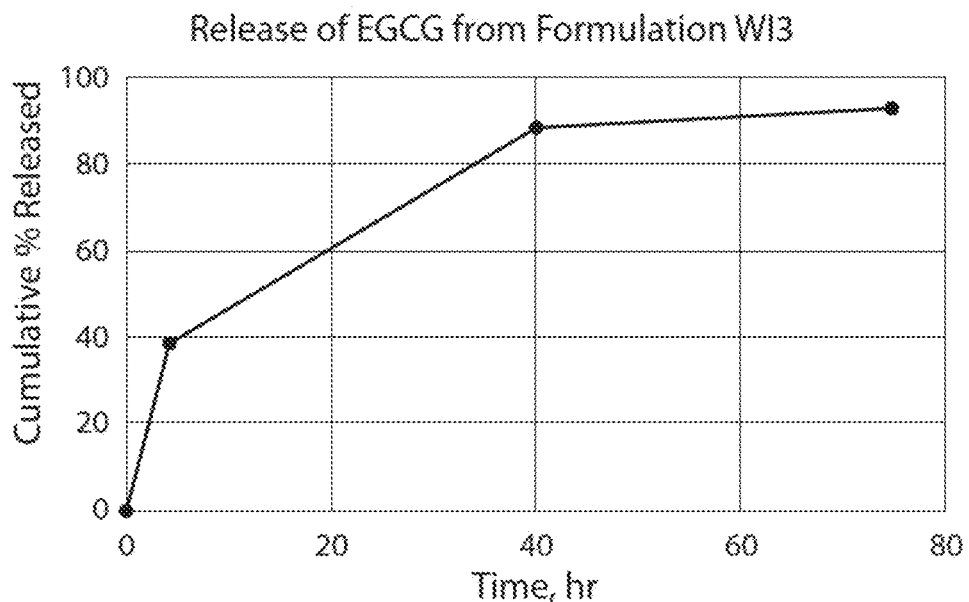
FIG. 26 depicts Release of EGCG from Formulation WI3.
Figure 27:
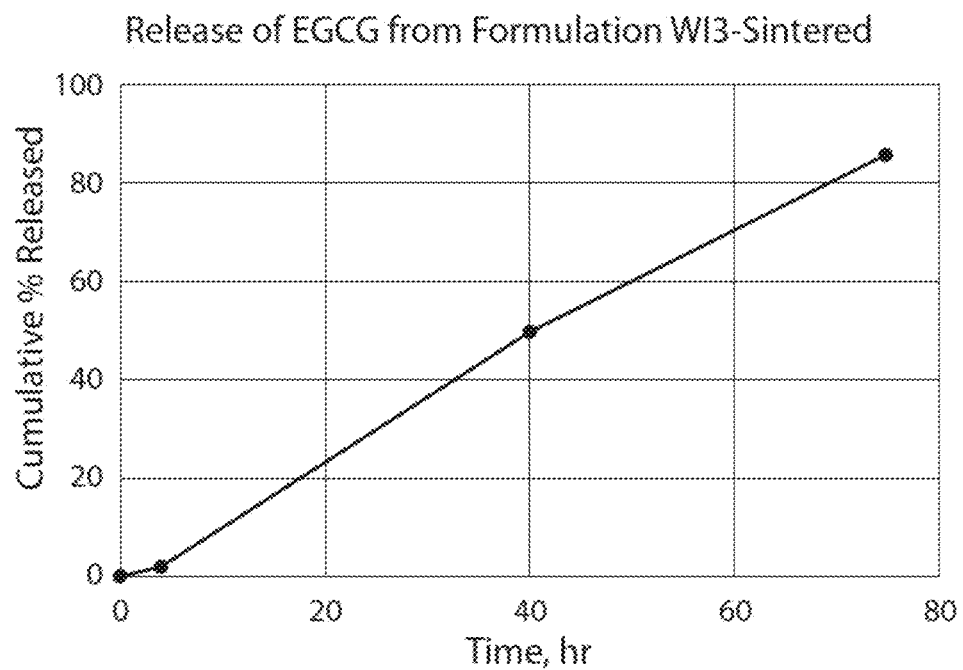
FIG. 27 depicts Release of EGCG from Formulation WI3-sintered.

This is an example of a matrix-type sustained release formulation, made with water insoluble polymer (in this case, Eudragit RL PO). In order to further decrease the release rate, the water insoluble polymer was sintered using organic solvents. The core tablets were dipped in a mixture of 6 parts of acetone and 4 parts of IPA and allowed to dry. This process was repeated 3 times. The sintered tablets were dried overnight at 37° C. The release profile from those sintered tablets is shown in FIG. 24. Compared to unsintered WI2 tablets, the sintered tablets show a significant decrease in release profile, attained by sintering of the polymer particles in the tablet formulation, forming a stronger barrier to release. At the end of dissolution, the tablets were intact and hard.

Figure 39:
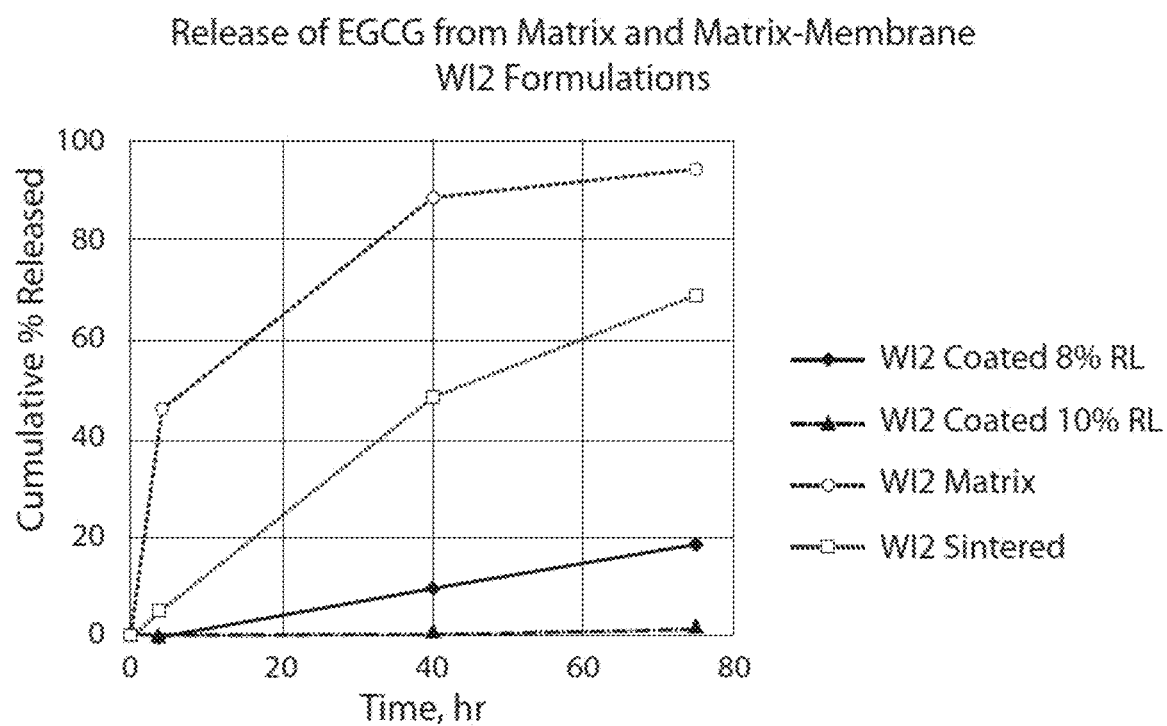
FIG. 39 depicts Release of EGCG from Matrix and Matrix-Membrane WI2 Formulations.

Comparison of WI2 pre-sintered formulation with sintered formulation is shown in the graph "Release of EGCG from RS-Matrix WI2, Effect of Sintering" (FIG. 39). Sintering resulted in elimination of burst-effect, substantially decreased release rate, making it linear.

Formulation WI3: Core Tablet Formula

| Ingredient | mg/tablet |
| --- | --- |
| EGCG | 75 |
| Eudragit RS PO | 150 |
| CSD | 3 |
| Sodium Stearyl Fumarate | 6 |

This is an example of a matrix-type sustained release formulation, made with water insoluble polymer (in this case, Eudragit RS PO). The powder blend was compressed to hardness between 10 and 15 Kg. Due to the nature of the water insoluble polymer, at the end of 75 h dissolution, the tablets looked the same as before beginning of dissolution (no swelling). The release profile from those tablets is shown in FIG. 28.

Formulation WI3 Sintered: Core Tablet Formula the Same as Formulation W13.

This is an example of a matrix-type sustained release formulation, made with water insoluble polymer (in this case, Eudragit RS PO). In order to further decrease the release rate, the water insoluble polymer was sintered using organic solvents. The core tablets were dipped in a mixture of 6 parts of acetone and 4 parts of IPA and allowed to dry. This process was repeated 3 times. The sintered tablets were dried overnight at 37° C. The release profile from those sintered tablets is shown in FIG. 28. Compared to unsintered tablets, sintering resulted in decreasing and linearizing the release profile. At the end of dissolution, the tablets were swollen but intact.

Figure 28:
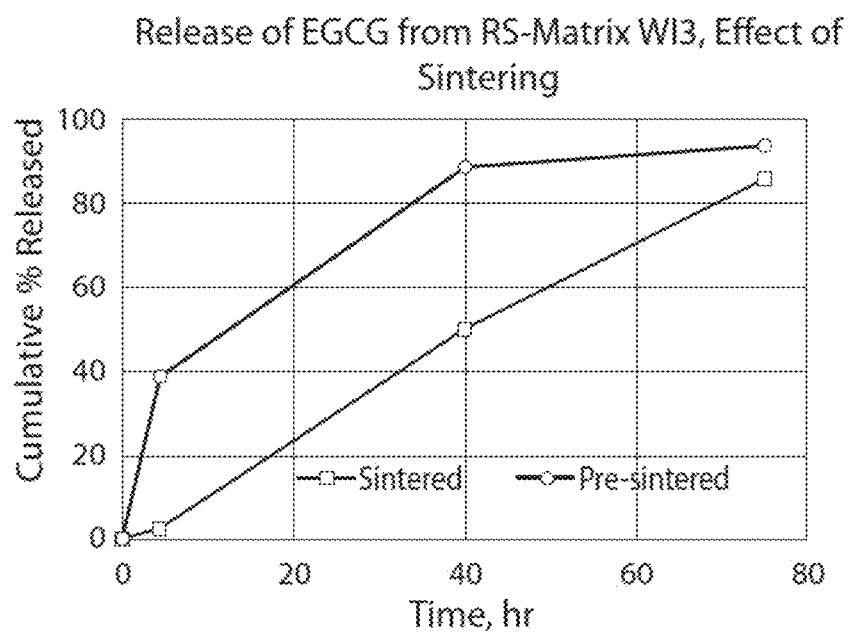
FIG. 28 depicts the Effect of Sintering on Release of EGCG from RS-Matrix WI3.

Comparison of WI3 pre-sintered formulation with sintered formulation is shown in graph "Release of EGCG from RS-Matrix WI3, Effect of Sintering" (FIG. 28). Sintering resulted in elimination of burst-effect, substantially decreased release rate and made it linear.

Formulation WI4: Core Tablet Formula

| Ingredient | mg/tablet |
| --- | --- |
| EGCG | 50 |
| Eudragit RL PO | 200 |
| talc | 3 |
| Magnesium stearate | 3 |

Figure 29:
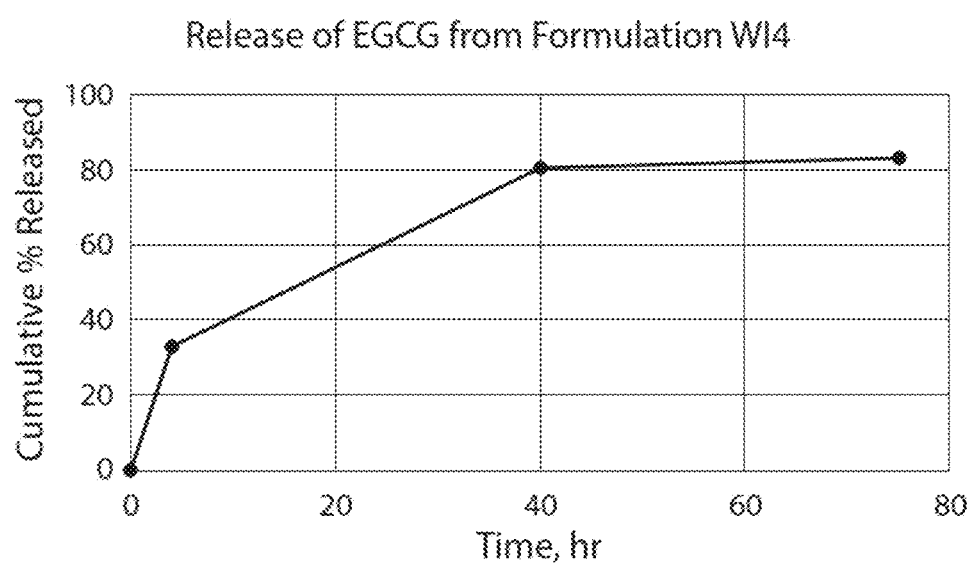
FIG. 29 depicts Release of EGCG from Formulation WI4.

This is an example of a matrix-type sustained release formulation, made with water insoluble polymer (in this case, Eudragit RL PO). The powder blend was compressed to hardness between 10 and 15 Kg. Due to the nature of the water insoluble polymer, at the end of 75 h dissolution, the tablets looked the same as before beginning of dissolution (no swelling). The release profile from those tablets is shown in FIG. 29.

Formulation WI5: Core Tablet Formula

| Ingredient | mg/tablet |
| --- | --- |
| EGCG | 200 |
| Eudragit RS PO | 100 |
| Talc | 3 |
| Magnesium stearate | 3 |

Figure 30:
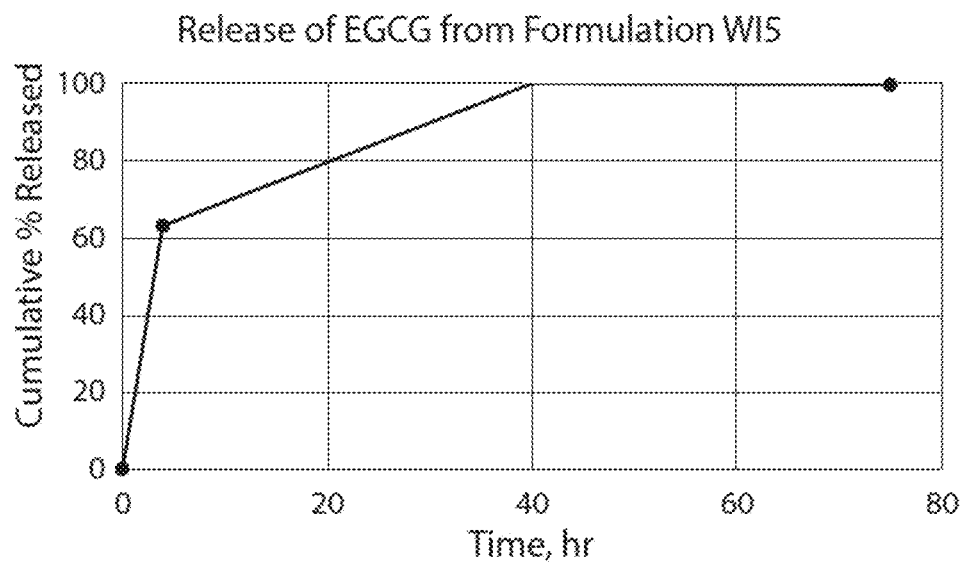
FIG. 30 depicts Release of EGCG from Formulation WI5.

This is an example of a matrix-type sustained release formulation, made with water insoluble polymer (in this case, Eudragit RS PO). The powder blend was compressed to hardness between 10 and 15 Kg. The release profile from those tablets is shown in FIG. 30. At the end of dissolution, no intact tablet core was observed.

Formulation WI5 Sintered: Core Tablet Formula the Same as Formulation W15

Figure 31:
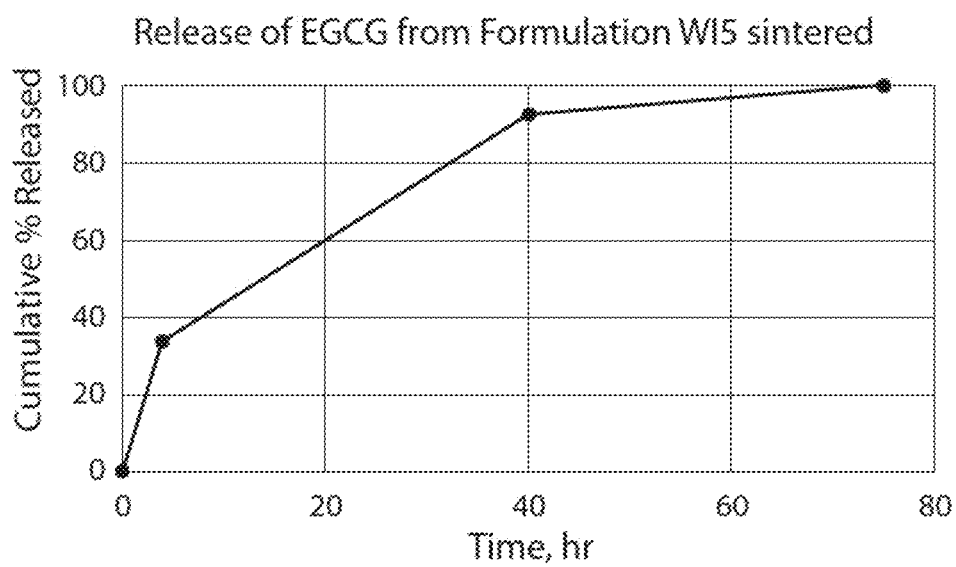
FIG. 31 depicts Release of EGCG from Formulation WI5-sintered.

This is an example of a matrix-type sustained release formulation, made with water insoluble polymer (in this case, Eudragit RS PO). In order to further decrease the release rate, the water insoluble polymer was sintered using organic solvents. The core tablets were dipped in a mixture of 6 parts of acetone and 4 parts of IPA and allowed to dry. This process was repeated 3 times. The sintered tablets were dried overnight at 37° C. The release profile from those sintered tablets is shown in FIG. 31. At the end of dissolution, no intact tablet cores were present.

Figure 32:
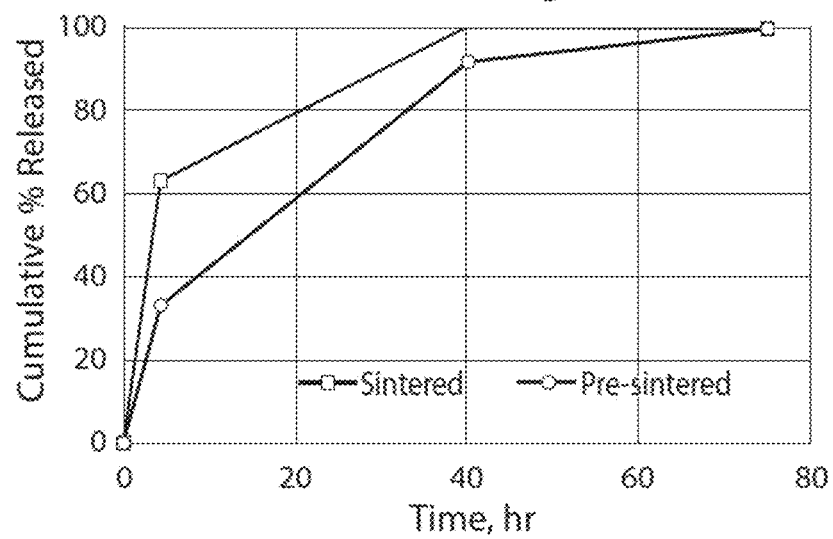
FIG. 32 depicts the Effect of Sintering on Release of EGCG from RS-Matrix WI5.

Comparison of WI5 pre-sintered formulation with sintered formulation is shown in graph "Release of EGCG from RS-Matrix WI5, Effect of Sintering" (FIG. 32). Surprisingly, compared to effect of sintering observed for WI2 and WI3, in case of WI5, sintering resulted in enhancement of burst-effect and release rate.

Figure 33:
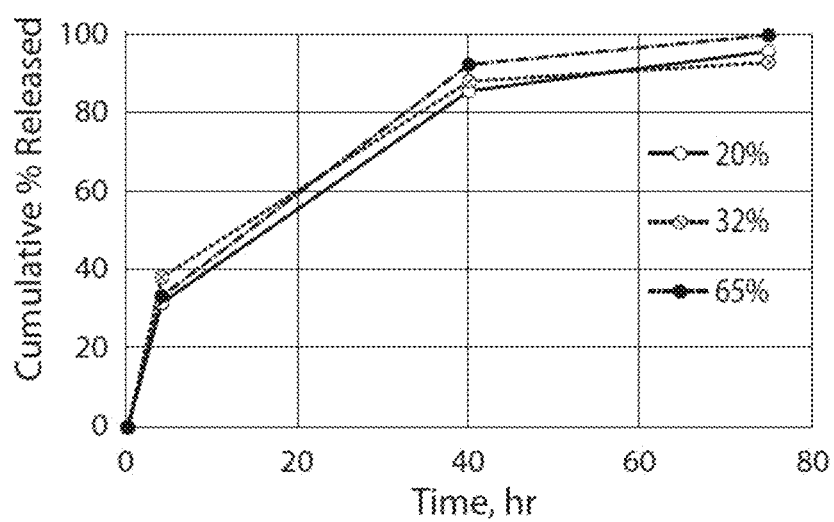
FIG. 33 depicts Release of EGCG from RS-Matrix.

Above formulations from WI1-WI5 can also be consolidated by the polymer. Release profile for formulations (WI1, WI3 and WI5) containing Eudragit RS PO polymer are shown in graph "Release of EGCG from RS-Matrix" (FIG. 33). The graph shows release rate decreasing with time and shows surprisingly very little effect of the % EGCG on rate of release.

Figure 34:
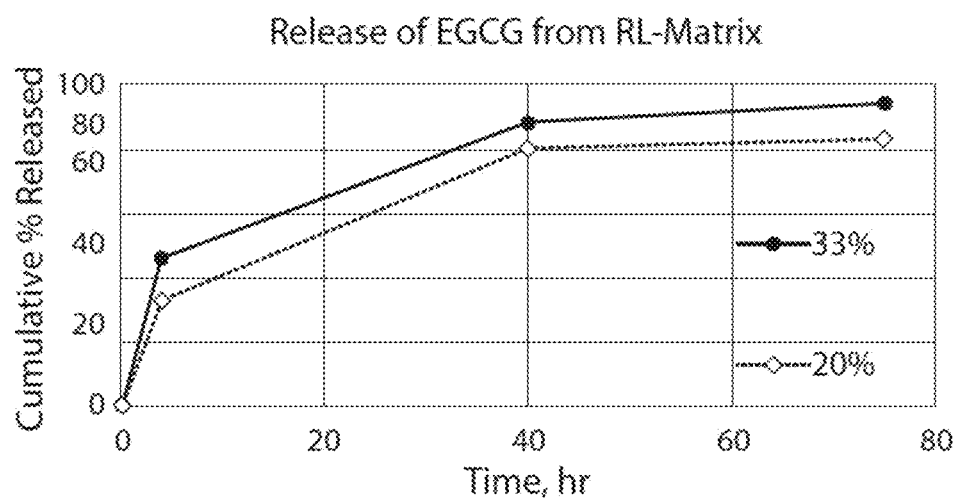
FIG. 34 depicts Release of EGCG from RL-Matrix.

Release profile for formulations containing Eudragit RL PO polymer (WI2 and WI4) are shown in graph "Release of EGCG from RL-Matrix" (FIG. 34). The figure shows smaller burst-release with lower % of EGCG in the matrix tablet formulation.

Formulation WI2 Coated with Eudragit RS at 6% Weight Gain: Core Tablet Formula the Same as Formulation WI2

Figure 35:
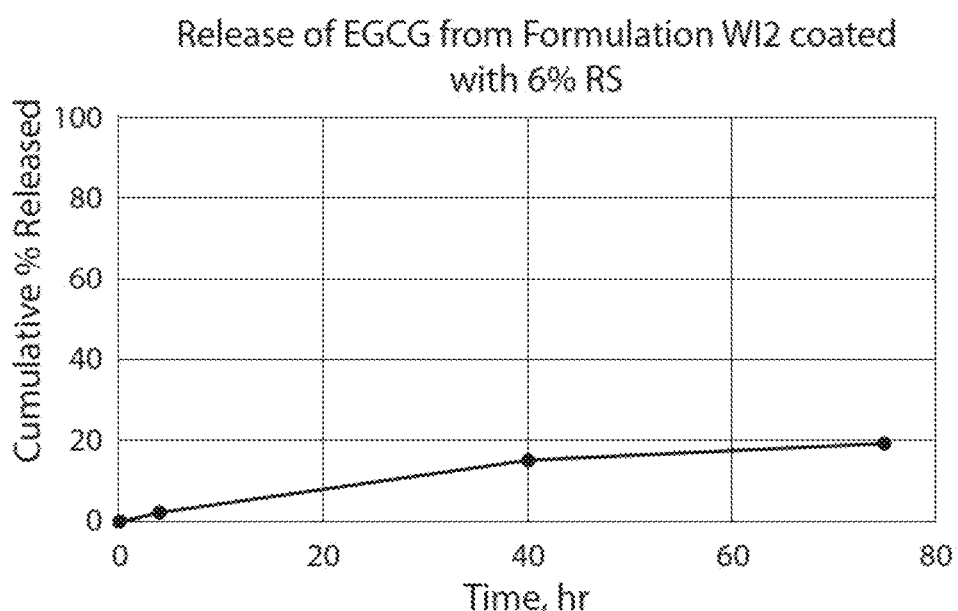
FIG. 35 depicts Release of EGCG from Formulation WI2 coated with 6% RS.

This is an example of a matrix-membrane type sustained release formulation, made with water insoluble polymer (in this case, both the matrix and membrane polymer are Eudragit RS). In order to further decrease the release rate from WI2 tablets, the tablets were coated with Eudragit RS polymer to 6% weight gain. The coating was accomplished by dipping the core tablets in a 10% solution of Eudragit RS in solvent mixture of 6 parts of acetone and 4 parts of IPA. After each dip, the tablets were air dried. This process was repeated until desired weigh gain was achieved. The coated tablets were further dried overnight at 37° C. The release profile from those coated tablets is shown in FIG. 35. The coating significantly decreased release of EGCG from the formulation. At the end of dissolution, the coated tablets were intact but swollen.

Formulation WI2 Coated with Eudragit RS at 9% Weight Gain: Core Tablet Formula the Same as Formulation WI2

Figure 36:
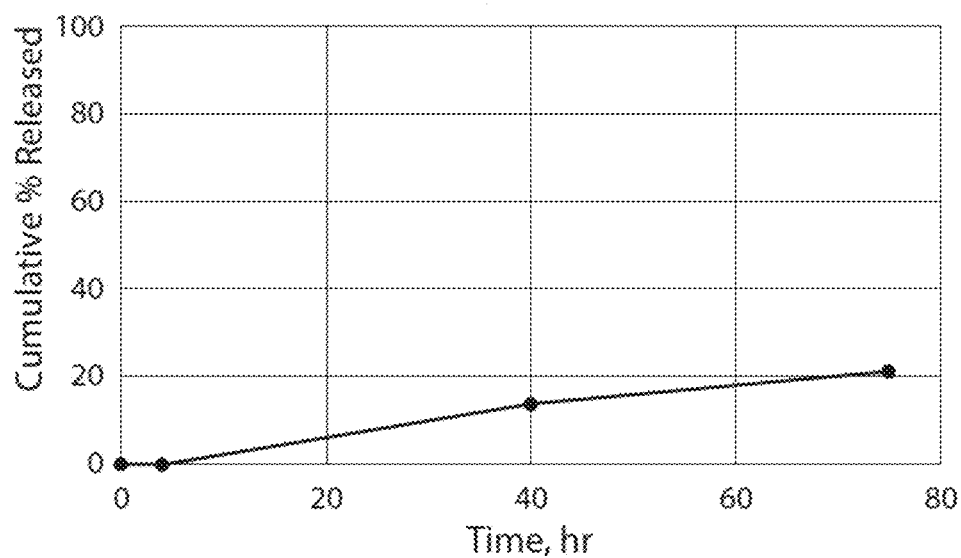
FIG. 36 depicts Release of EGCG from Formulation WI2 coated with 9% RS.
Figure 37:
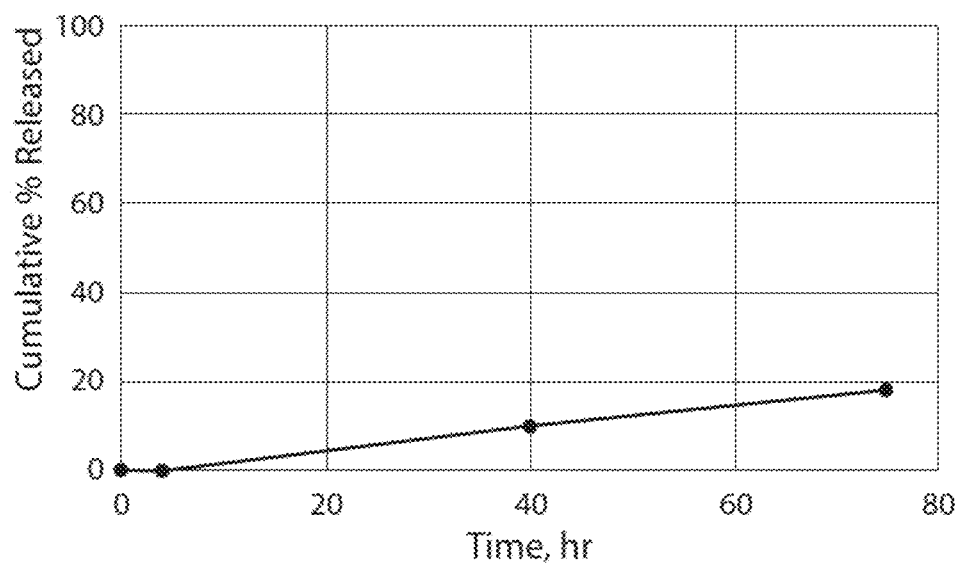
FIG. 37 depicts Release of EGCG from Formulation WI2 coated with 8% RL.
Figure 38:
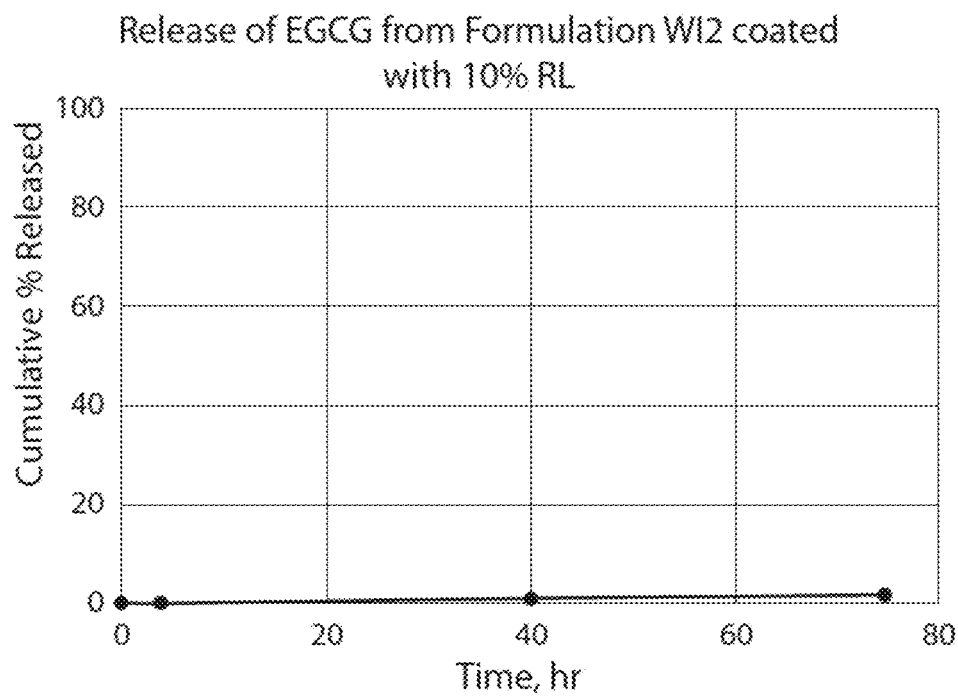
FIG. 38 depicts Release of EGCG from Formulation WI2 coated with 10% RL.

This is an example of a matrix-membrane type sustained release formulation, made with water insoluble polymer (in this case, both the matrix and membrane polymer were Eudragit RS). In order to further decrease the release rate from WI2 tablets, the tablets were coated with Eudragit RS polymer to 9% weight gain. The coating was accomplished by dipping the core tablets in a 10% solution of Eudragit RS in solvent mixture of 6 parts of acetone and 4 parts of IPA. After each dip, the tablets were air-dried. This process was repeated until desired weigh gain was achieved. The coated tablets were further dried overnight at 37° C. The release profile from those coated tablets is shown in FIG. 36. The coating significantly decreased release of EGCG from the formulation. At the end of dissolution, the coated tablets were intact but swollen.

Formulation WI2 Coated with Eudragit RL at 8% Weight Gain: Core Tablet Formula the Same as Formulation WI2

This is an example of a matrix-membrane type sustained release formulation, made with water insoluble polymer (in this case, the matrix polymer was Eudragit RS, while the membrane polymer was Eudragit RL). The coating was accomplished by dipping the core tablets in a 10% solution of Eudragit RL in solvent mixture of 6 parts of acetone and 4 parts of IPA. After each dip, the tablets were air-dried. This process was repeated until 8% weigh gain was achieved. The coated tablets were further dried overnight at 37° C. The release profile from those coated tablets is shown in FIG. 39. The coating significantly decreased release of EGCG from the formulation. At the end of dissolution, the coated tablets were intact and swollen.

Formulation WI2 Coated with Eudragit RL at 10% Weight Gain: Core Tablet Formula the Same as Formulation WI2

This is an example of a matrix-membrane type sustained release formulation, made with water insoluble polymer (in this case, the matrix polymer was Eudragit RS, while the membrane polymer was Eudragit RL). The coating was accomplished by dipping the core tablets in a 10% solution of Eudragit RL in solvent mixture of 6 parts of acetone and 4 parts of IPA. After each dip, the tablets were air dried. This process was repeated until 10% weigh gain was achieved. The coated tablets were further dried overnight at 37° C. The release profile from those coated tablets is shown in FIG. 39. The coating significantly decreased release of EGCG from the formulation. At the end of dissolution, the coated tablets were intact but swollen.

Graph of release from WI2 matrix and WI2 matrix with RL-membrane formulations is shown in graph "Release of EGCG from Matrix and Matrix-Membrane WI2 Formulations" (FIG. 39). The graph shows decreasing release rate with sintering and increasing membrane coating.

Formulation WI3 Coated with Eudragit RS at 6% Weight Gain: Core Tablet Formula the Same as Formulation WI3

Figure 40:
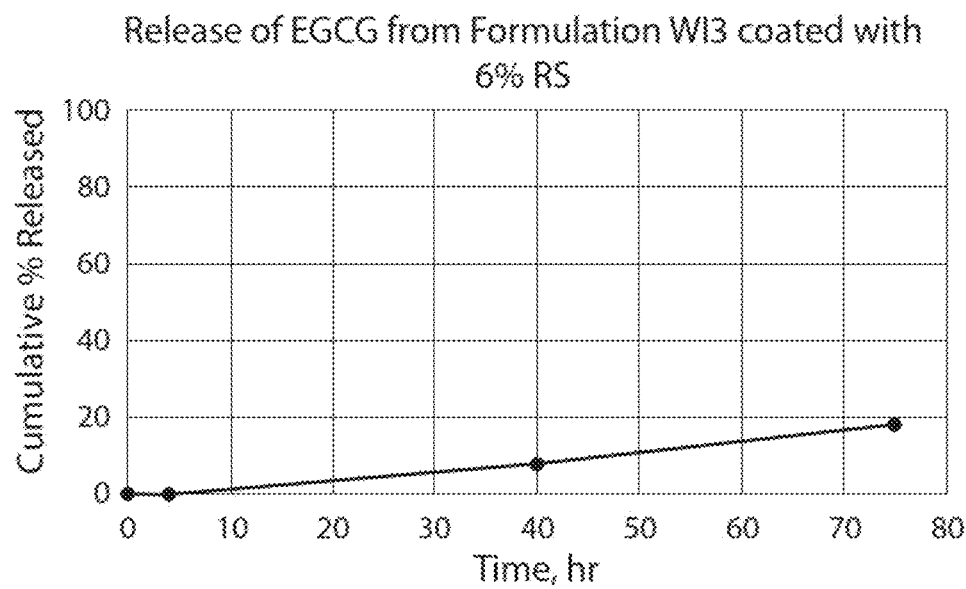
FIG. 40 depicts Release of EGCG from Formulation WI3 coated with 6% RS.

This is an example of a matrix-membrane type sustained release formulation, made with water insoluble polymer (in this case, matrix polymer was Eudragit RL and membrane polymer was Eudragit RS). In order to further decrease the release rate from WI3 tablets, the tablets were coated with Eudragit RS polymer to 6% weight gain. The coating was accomplished by dipping the core tablets in a 10% solution of Eudragit RS in solvent mixture of 6 parts of acetone and 4 parts of IPA. After each dip, the tablets were air-dried. This process was repeated until desired weigh gain was achieved. The coated tablets were further dried overnight at 37° C. The release profile from those coated tablets is shown in FIG. 40. The coating significantly decreased release of EGCG from the formulation. At the end of dissolution, the coated tablets were intact but swollen. Compared to tablets coated to 8% weight gain with Eudragit RL polymer, additional 2% weight gain resulted in further decrease in release rate.

Formulation WI3 Coated with Eudragit RS at 9% Weight Gain: Core Tablet Formula the Same as Formulation WI3

Figure 41:
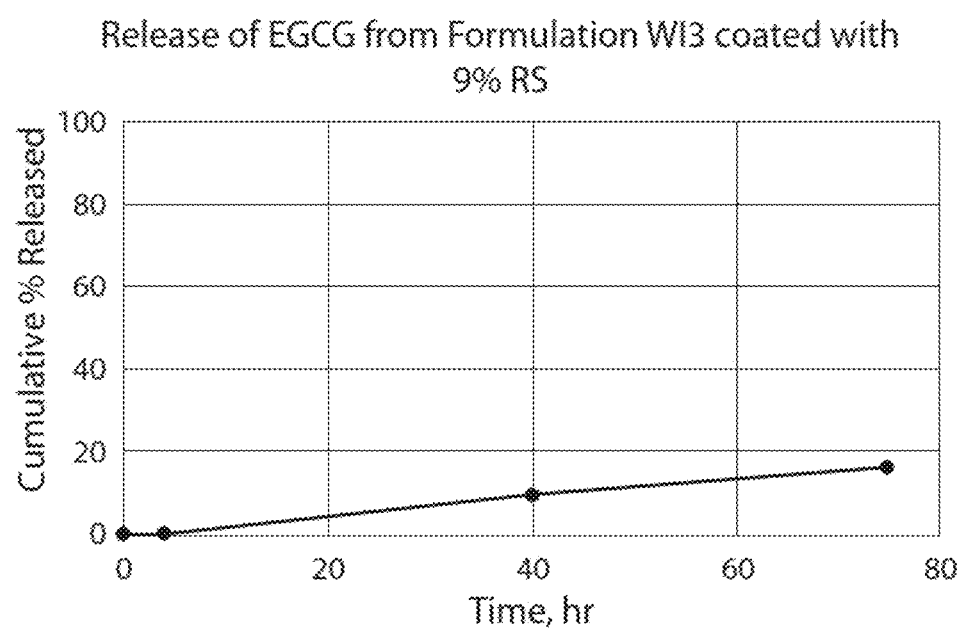
FIG. 41 depicts Release of EGCG from Formulation WI3 coated with 9% RS.

This is an example of a matrix-membrane type sustained release formulation, made with water insoluble polymer (in this case, matrix polymer was Eudragit RL and membrane polymer was Eudragit RS). In order to further decrease the release rate from WI3 tablets, the tablets were coated with Eudragit RS polymer to 9% weight gain. The coating was accomplished by dipping the core tablets in a 10% solution of Eudragit RS in solvent mixture of 6 parts of acetone and 4 parts of IPA. After each dip, the tablets were air-dried. This process was repeated until desired weigh gain was achieved. The coated tablets were further dried overnight at 37° C. The release profile from those coated tablets is shown in FIG. 41. The coating significantly decreased release of EGCG from the formulation. At the end of dissolution, the coated tablets were intact but swollen.

Formulation WI3 Coated with Eudragit RL at 8% Weight Gain: Core Tablet Formula the Same as Formulation WI3

Figure 42:
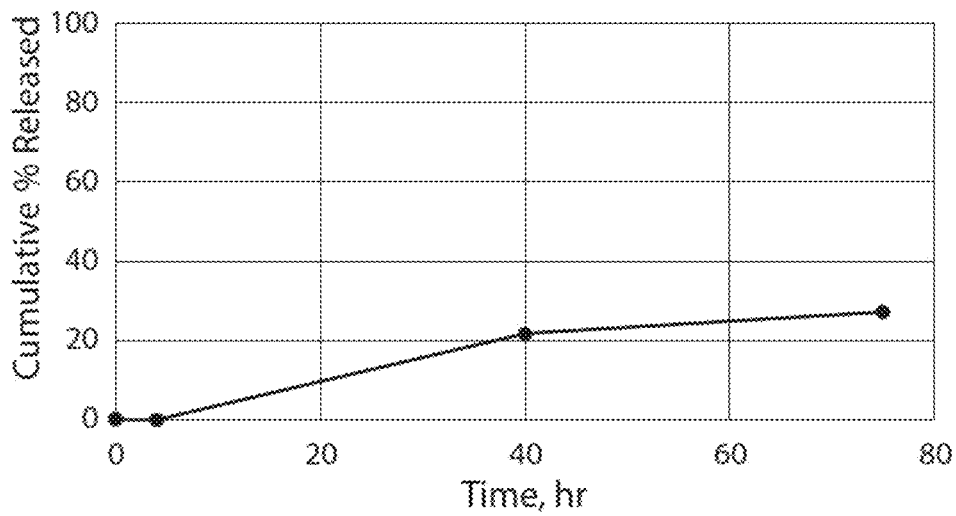
FIG. 42 depicts Release of EGCG from Formulation WI3 coated with 8% RL.

This is an example of a matrix-membrane type sustained release formulation, made with water insoluble polymer (in this case, both the matrix and membrane polymer are Eudragit RL). The coating was accomplished by dipping the core tablets in a 10% solution of Eudragit RL in solvent mixture of 6 parts of acetone and 4 parts of IPA. After each dip, the tablets were air dried. This process was repeated until 8% weigh gain was achieved. The coated tablets were further dried overnight at 37° C. The release profile from those coated tablets is shown in FIG. 42. The coating significantly decreased release of EGCG from the formulation. At the end of dissolution, the coated tablets were intact but swollen.

Formulation WI3 Coated with Eudragit RL at 10% Weight Gain: Core Tablet Formula the Same as Formulation WI3

Figure 43:
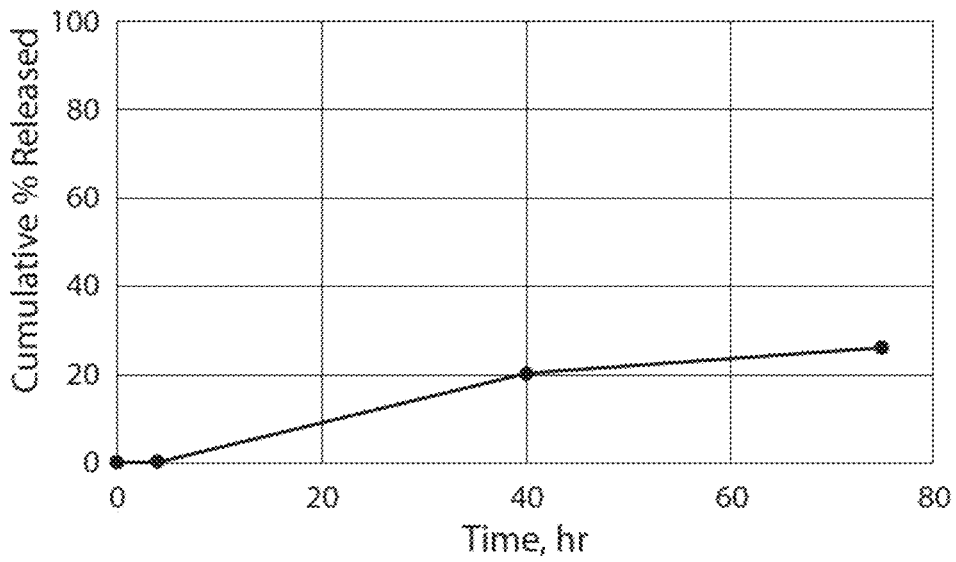
FIG. 43 depicts Release of EGCG from Formulation WI2 coated with 10% RL.

This is an example of a matrix-membrane type sustained release formulation, made with water insoluble polymer (in this case, both the matrix and membrane polymer were Eudragit RL). The coating was accomplished by dipping the core tablets in a 10% solution of Eudragit RL in solvent mixture of 6 parts of acetone and 4 parts of IPA. After each dip, the tablets were allowed to air-dry. This process was repeated until 10% weigh gain was achieved. The coated tablets were further dried overnight at 37° C. The release profile from those coated tablets is shown in FIG. 43. The coating significantly decreased release of EGCG from the formulation. At the end of dissolution, the coated tablets were intact but swollen.

Formulation WI5 Coated with Eudragit RS at 6% Weight Gain: Core Tablet Formula the Same as Formulation WI5

Figure 44:
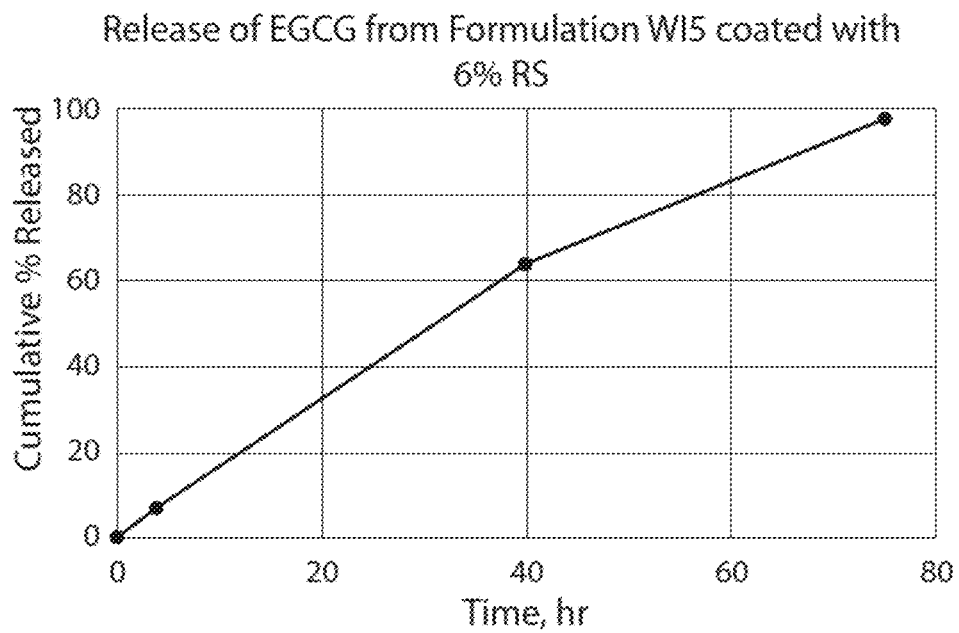
FIG. 44 depicts Release of EGCG from Formulation WI5 coated with 6% RS.

This is an example of a matrix-membrane type sustained release formulation, made with water insoluble polymer (in this case, both the matrix and membrane polymer were Eudragit RS). The coating was accomplished by dipping the core tablets in a 10% solution of Eudragit RS in solvent mixture of 6 parts of acetone and 4 parts of IPA. After each dip, the tablets were air dried. This process was repeated until 6% weigh gain was achieved. The coated tablets were further dried overnight at 37° C. The release profile from those coated tablets is shown in FIG. 44. The coating significantly decreased release of EGCG from the formulation. At the end of dissolution, the tablet was found to be only a shell coating that broke easily.

Formulation WI5 Coated with Eudragit RL at 8% Weight Gain: Core Tablet Formula the Same as Formulation WI5

Figure 45:
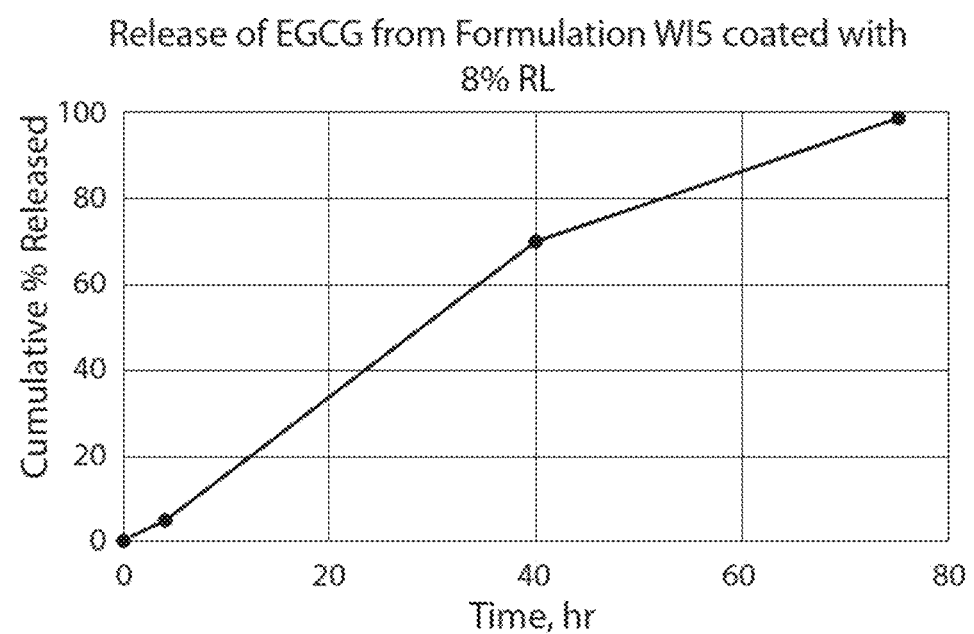
FIG. 45 depicts Release of EGCG from Formulation WI5 coated with 8% RL.

This is an example of a matrix-membrane type sustained release formulation, made with water insoluble polymer (in this case, both the matrix and membrane polymer are Eudragit RL). The coating was accomplished by dipping the core tablets in a 10% solution of Eudragit RL in solvent mixture of 6 parts of acetone and 4 parts of IPA. After each dip, the tablets were air dried. This process was repeated until 8% weight gain was achieved. The coated tablets were further dried overnight at 37° C. The release profile from those coated tablets is shown in FIG. 45. The coating significantly decreased release of EGCG from the formulation. At the end of dissolution, the tablet was found to be only a shell coating that broke easily.

Formulation WI7 Coated with Eudragit RL at 6% Weight Gain: Core Tablet Formula W17

| Ingredient | mg/tablet |
| --- | --- |
| EGCG | 200 |
| Eudragit RL PO | 80 |
| Talc | 3 |
| Magnesium stearate | 3 |

This is an example of a matrix-type sustained release formulation, made with water insoluble polymer (in this case, Eudragit RL PO). The powder blend was compressed to hardness between 10 and 15 Kg.

Figure 46:
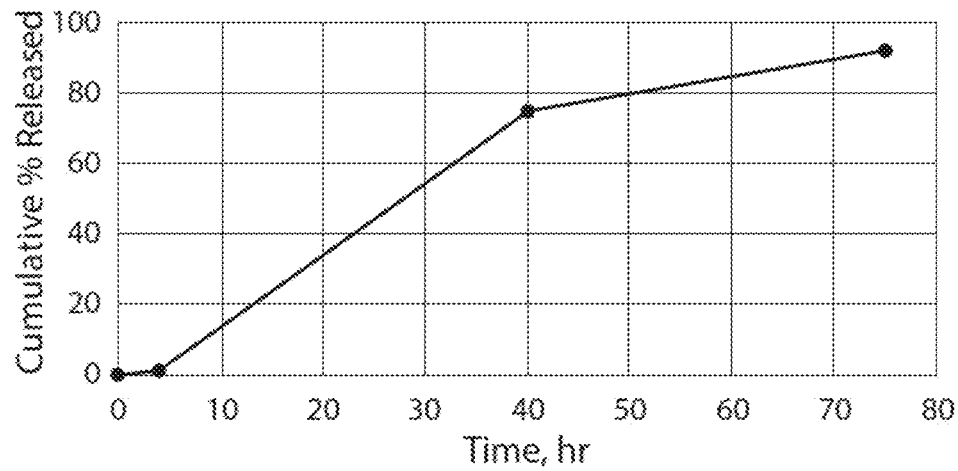
FIG. 46 depicts Release of EGCG from Formulation WI7 coated with 6% RL.

Coating: The tablets were coated with Eudragit RL polymer to 6% weight gain. The coating was accomplished by dipping the core tablets in a 10% solution of Eudragit RL in solvent mixture of 6 parts of acetone and 4 parts of IPA. After each dip, the tablets were air dried. This process was repeated until desired weigh gain was achieved. The coated tablets were further dried overnight at 37° C. The release profile from those coated tablets is shown in FIG. 46. At the end of the dissolution, the coated tablet appeared to be intact but was very fragile.

Formulation WI7 Coated with Eudragit RL/PEG at 6% Weight Gain: Core Tablet Formula the Same as Formulation WI7

Figure 47:
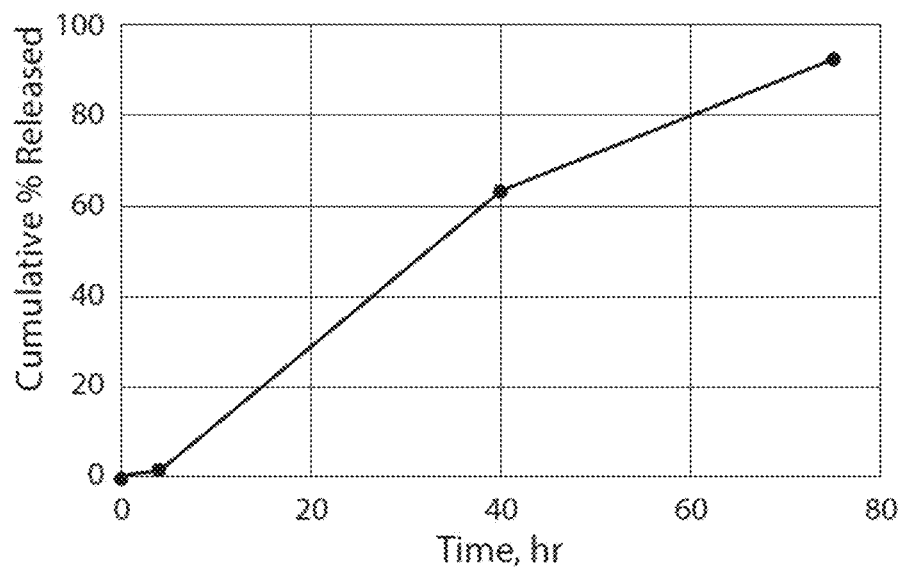
FIG. 47 depicts Release of EGCG from Formulation WI7 coated with 6% RL/PEG.

This is an example of a matrix-membrane type sustained release formulation, made with water insoluble polymer (in this case, both the matrix and membrane polymer are Eudragit RL). The WI7 tablets were coated with Eudragit RL polymer containing PEG 3350 to 6% weight gain. The coating was accomplished by dipping the core tablets in a solution containing 9% Eudragit RL and 1% PEG 3350 in solvent mixture of 6 parts of acetone and 4 parts of IPA. After each dip, the tablets were air dried. This process was repeated until desired weight gain was achieved. The coated tablets were further dried overnight at 37° C. The release profile from those coated tablets is shown in FIG. 47. At the end of the dissolution, the coated tablet appeared to be intact but was very fragile.

Formulation WI8 Coated with Eudragit RL at 6% Weight Gain: Core Tablet Formula WI8

| Ingredient | mg/tablet |
| --- | --- |
| EGCG | 250 |
| Eudragit RL PO | 50 |

-continued

| Ingredient | mg/tablet |
|---|---|
| Colloidal Silicon Dioxide | 3 |
| Magnesium stearate | 3 |

This is an example of a matrix-type sustained release formulation, made with water insoluble polymer (in this case, Eudragit RL PO). The powder blend was compressed to hardness between 10 and 15 Kg.

Figure 48:
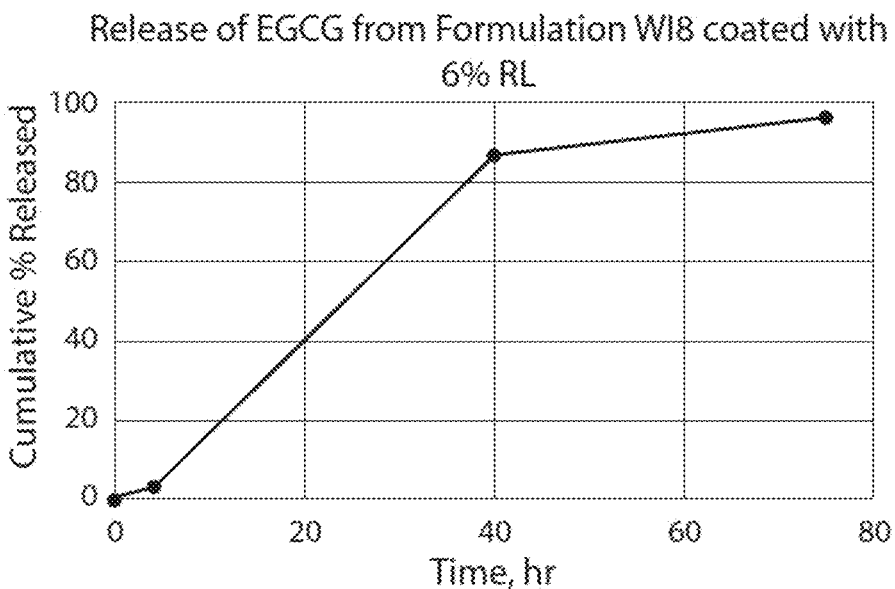
FIG. 48 depicts Release of EGCG from Formulation WI8 coated with 6% RL.

Coating: The tablets were coated with Eudragit RL polymer to 6% weight gain. The coating was accomplished by dipping the core tablets in a 10% solution of Eudragit RLS in solvent mixture of 6 parts of acetone and 4 parts of IPA. After each dip, the tablets were air dried. This process was repeated until desired weigh gain was achieved. The coated tablets were further dried overnight at 37° C. The release profile from those coated tablets is shown in FIG. 48. At the end of the dissolution, the coated tablet appeared to be intact but was very fragile.

Formulation WI8 Coated with Eudragit RL/PEG at 6% Weight Gain: Core Tablet Formula the Same as Formulation WI8

Figure 49:
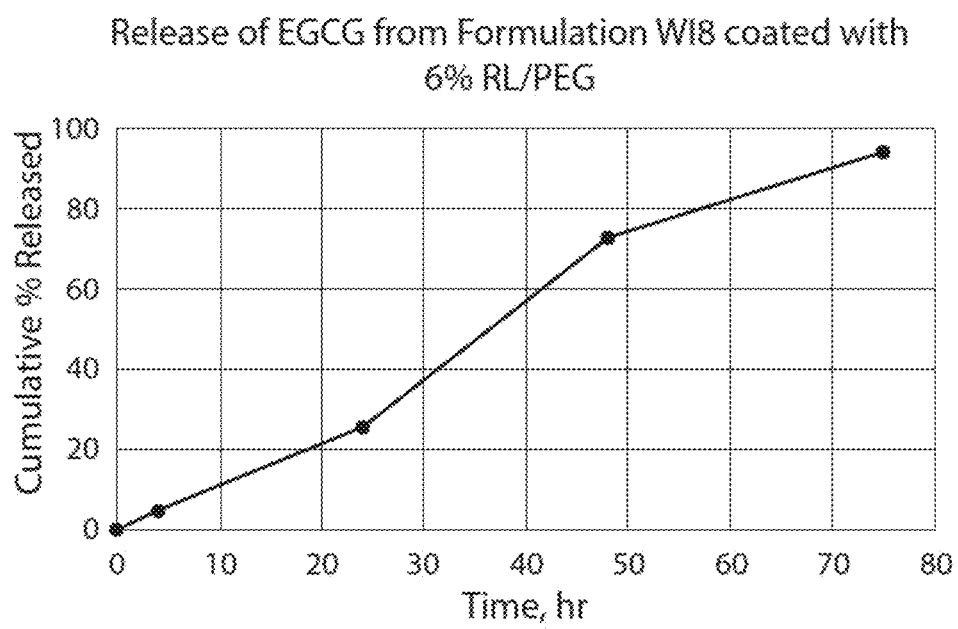
FIG. 49 depicts Release of EGCG from Formulation WI7 coated with 6% RL/PEG.

This is an example of a matrix-membrane type sustained release formulation, made with water insoluble polymer (in this case, both the matrix and membrane polymer are Eudragit RL). The tablets were coated with Eudragit RL polymer containing PEG 3350 to 6% weight gain. The coating was accomplished by dipping the core tablets in a solution containing 9% Eudragit RL and 1% PEG 3350 in solvent mixture of 6 parts of acetone and 4 parts of IPA. After each dip, the tablets were air dried. This process was repeated until desired weigh gain was achieved. The coated tablets were further dried overnight at 37° C. The release profile from those coated tablets is shown in FIG. 49. At the end of the dissolution, the coated tablet appeared to be intact but was very fragile.

Example 18. Hot Melt Extrusion Formulations

Formulation HME-4: Pellet Formula

| Ingredient | mg/capsule |
|---|---|
| EGCG | 46 |
| Ethyl cellulose | 46 |
| Dibutyl sebacate | 23 |

The powder blend is extruded through 3 mm die in a twin screw hot melt extruder to generate rods containing homogeneous dispersion of EGCG in plasticized polymer. The rods are cut in 3 mm length and about 115 mg of resultant pellets are filled in size 2 HPMC capsules.

Figure 50:
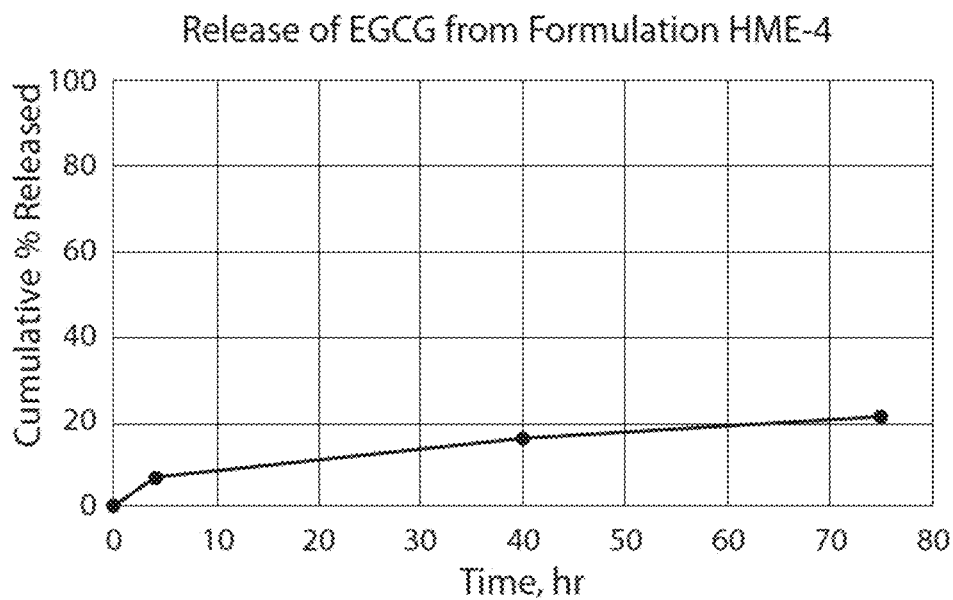
FIG. 50 depicts Release of EGCG from Formulation HME-4.

Two capsules are placed in each dissolution flask for release testing procedure described herein. The release profile from those hot melt extruded granules is shown in FIG. 50. At the end of dissolution, the pellets were intact and hard to crush.

Formulation HME-5: Pellet Formula

| Ingredient | mg/capsule |
|---|---|
| EGCG | 40.25 |
| Ethyl cellulose | 23 |
| HPMC CR | 17.25 |

-continued

| Ingredient | mg/capsule |
|---|---|
| Dibutyl sebacate | 11.5 |
| Propylene glycol | 23 |

The powder blend is extruded through 3 mm die in a twin screw hot melt extruder to generate rods containing homogeneous dispersion of EGCG in plasticized polymer. The rods are cut in 3 mm length and about 115 mg of resultant pellets are filled in size 2 HPMC capsules.

Figure 51:
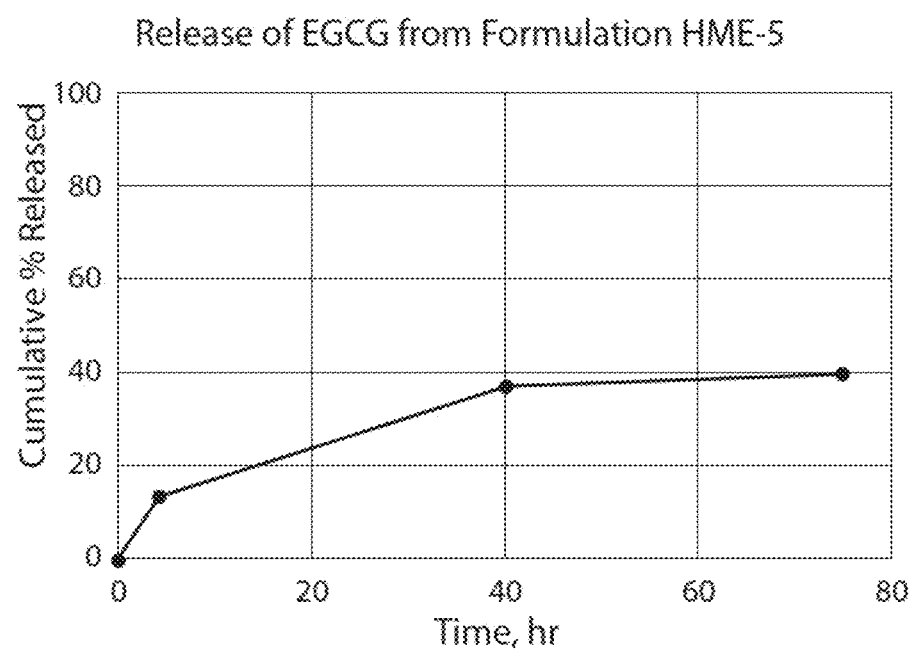
FIG. 51 depicts Release of EGCG from Formulation HME-5.

Two capsules are placed in each dissolution flask for release testing procedure described earlier. The release profile from those hot melt extruded granules is shown in FIG. 51. At the end of dissolution, the pellets were intact and hard to crush.

The HME-4 and HME-5 formulations show use of Hot Melt Extrusion technology to achieve sustained colonic release of the therapeutic agent. It is envisioned that increasing the proportion of therapeutic agent, decreasing proportion of rate controlling polymer and/or decreasing particle size will increase the release rate. Conversely, increasing particle size would likely further decrease release rate.

The formulation and procedures show many ways in which sustained colonic release of the therapeutic agent can be achieved as well as some of the factors that allow increasing or decreasing the release rate. These examples are not meant to suggest there are no other options to achieve sustained release in the colon.

Example 19. Ethyl Cellulose Coatings

Procedure: EGCG formulation described in Example 16 was compressed into 300 mg tablets as well as 50 mg minitablets. Both these were coated with ethyl cellulose (commercial Surelease formulation) and a plasticizer using parameters described in example 16. Dissolution studies were performed on the minitablets with 10, 20 and 30% weight gain as well as 300 mg tablets with 20% weight gain.

Description of the data: Increase in polymer weight gain resulted in a decrease in release rate—the minitablets with 10% coating released ~90% in ~2 h, minitablets with 20% coating released ~90% in ~12 h and minitablets with 30% coating released ~90% in 24 h. For the 20% weight gain, release profile from 300 mg tablets weren't significantly different from those for 50 mg minitablets.

Example 20: Curing Effect

Figure 9A:
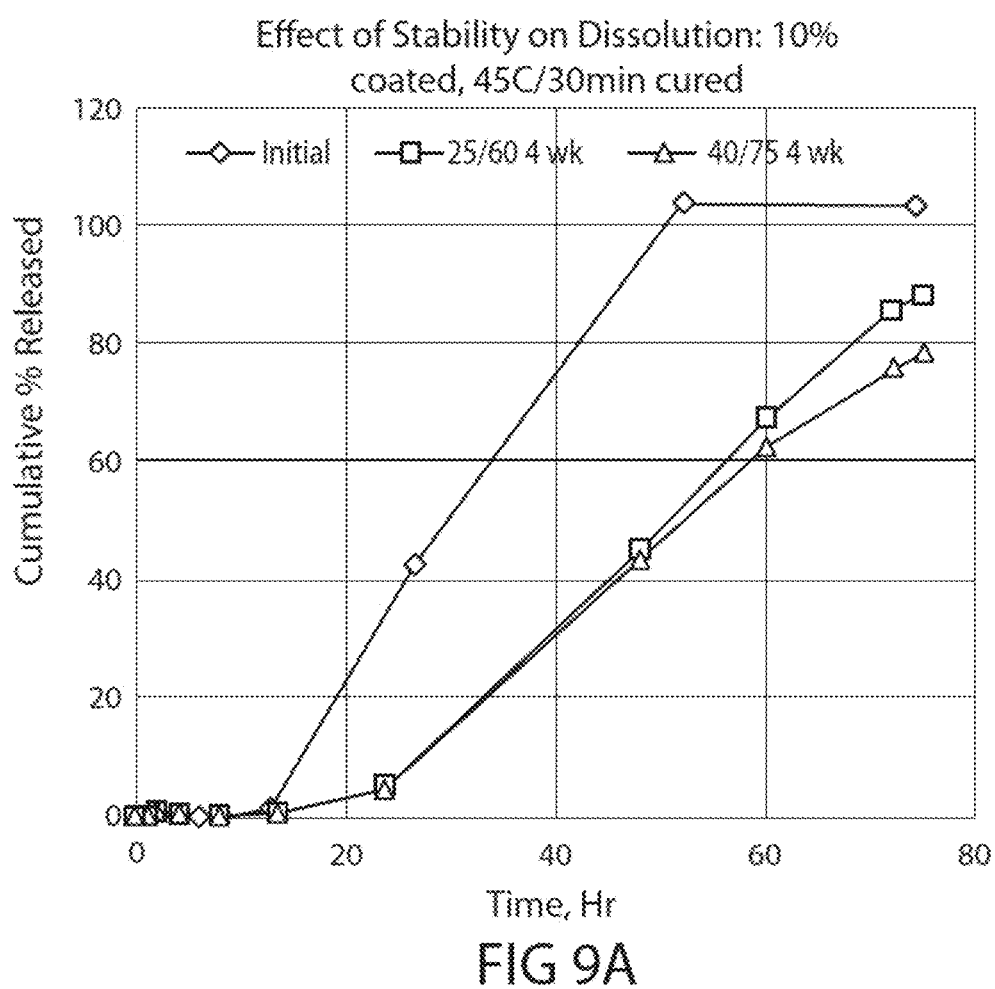
FIG. 9A depicts the dissolution rate of coated mini-tablets.
Figure 9B:
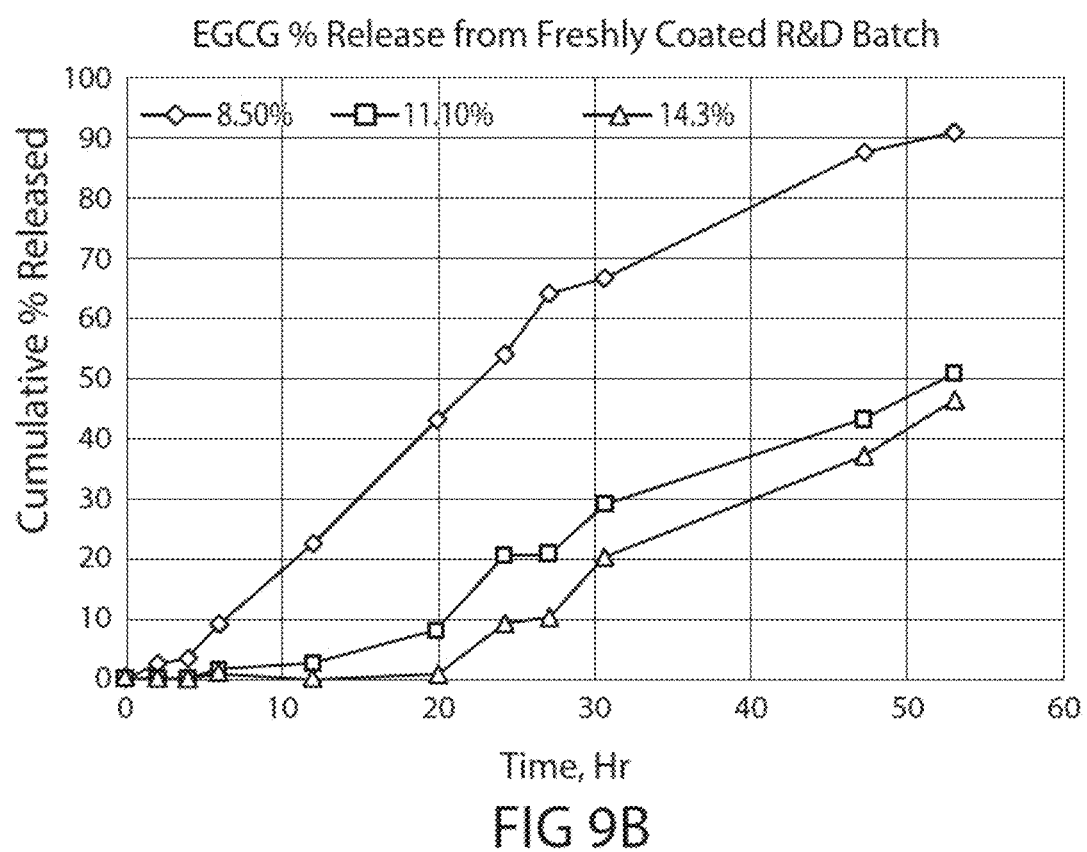
FIG. 9B depicts release rate of coated mini-tablets. See Example 19.

As shown in FIG. 9A, coated mini-tablets show a decrease in dissolution rate. This is called the curing effect, and is the result of the polymer droplets deposited during the coating operation coalesce to decrease the release rate from the film. In order to stabilize the release rate, the coated mini-tablets are cured at 60° C. for 4 h. As shown in FIG. 9B, mini-tablets cured in this manner show a significant decrease in release profile.

Example 21: Release Specifications

Colonic and whole gut transit times in human suffering from Parkinsons's Disease (PD) are much longer than those of healthy individuals. See, e.g., Rao, et al., Clinical Gastroenterology and Hepatology 2009; 7:537-544; and Knudsen, et al., Movement Disorders, Vol. 32, No. 1, 2017; 94-105. In certain embodiments, the solid dosage forms described herein release the active agent in the colon and/or lower gastrointestinal tract of a human subject as indicated in the following table:

| Time | Cumulative % Released | Cumulative % Released, Representative embodiment |
|---|---|---|
| 24 h | 10-50 | 20% |
| 48 h | 30-80 | 45% |
| 72 h | NLT 60% | 71% |
| 96 h | NLT 75% | 85% |

Example 22. Clinical Results

Figure 52:
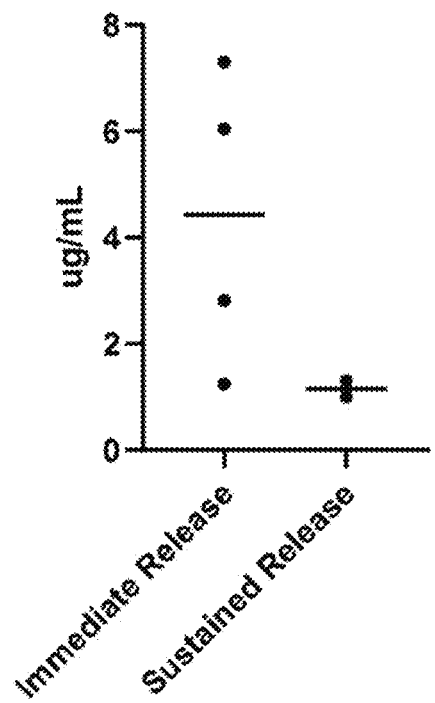
FIG. 52 depicts a Comparison of Plasma EGCG Concentration between IR (immediate release) and SR (sustained release) Formulations.
Figure 53:
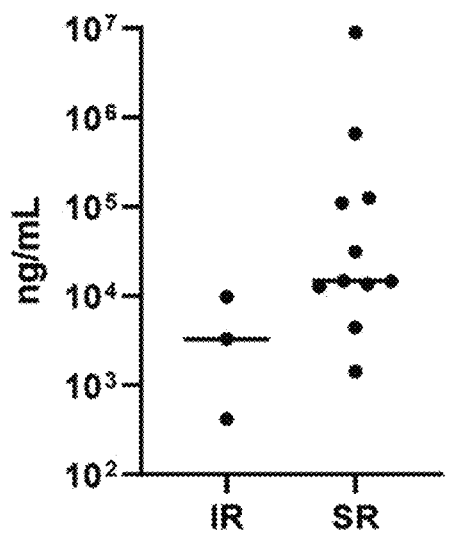
FIG. 53 depicts a Comparison of Fecal EGCG Concentration between IR and SR Formulations.

Plasma and Stool Samples:
Human subjects swallowed 300 mg EGCG per day in the form of immediate release capsule (150 mg BID) (see Example 13, Immediate Release Formulation) or sustained release (100 mg TID) formulations (see Example 13).
Collected before dosing (one to two baseline samples) and after 2 weeks of dosing
Analyzed for EGCG using a UPLC-MS/MS analytical method.
Plasma concentrations after 2 wk of dosing:
EGCG levels were quantifiable in all 4 subjects administered immediate release formulation. Peak EGCG concentration ranged from 1.2 ng/mL to 7.3 ng/mL, with average plasma concentration of 4.4 ng/mL.
In the sustained release group, only 2 out of 14 samples had quantifiable level of EGCG (1 ng/mL and 1.3 ng/mL), with average 1.15 ng/ml for the sustained release formulation.
These data show at least a 3.8-fold reduction in plasma-availability of EGCG for the Sustained Release formulation group. See FIG. 52.
Fecal concentrations after 2 wk of dosing:
In the immediate release group, EGCG levels were quantifiable in all 3 samples, ranging from 421 to 9,750 ng/g, average 4,480 ng/g.
In the sustained release group, EGCG levels were quantifiable in all samples and ranged from 1,430 ng/g to 8,930,000 ng/g (average of 901,597 ng/g).
These data show 201-fold increase in fecal-concentration of EGCG for the Sustained Release formulation group. See FIG. 53.

Example 23. Study on Gut Transit Time

Figure 54:
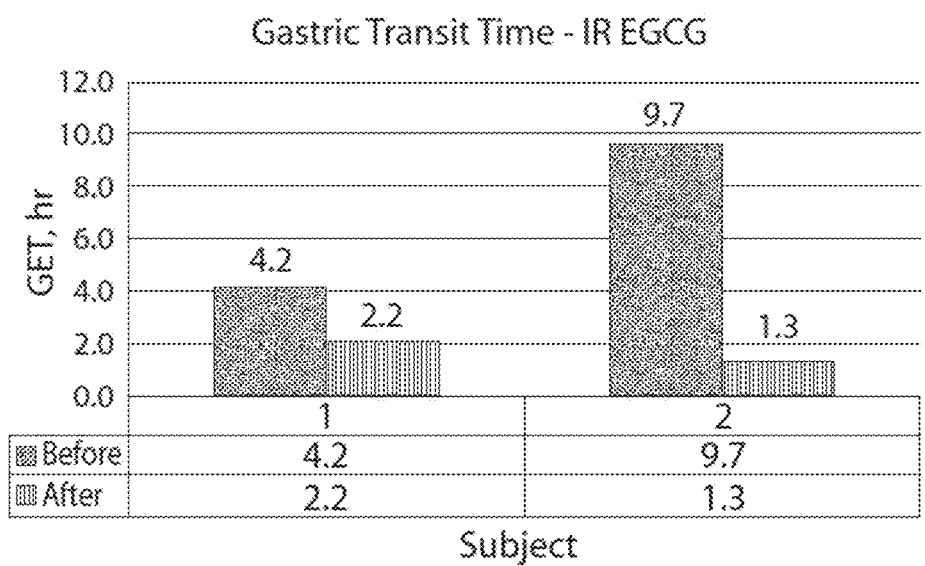
FIG. 54 depicts Gut Transit Time after administration of an IR EGCG Formulation.
Figure 55:
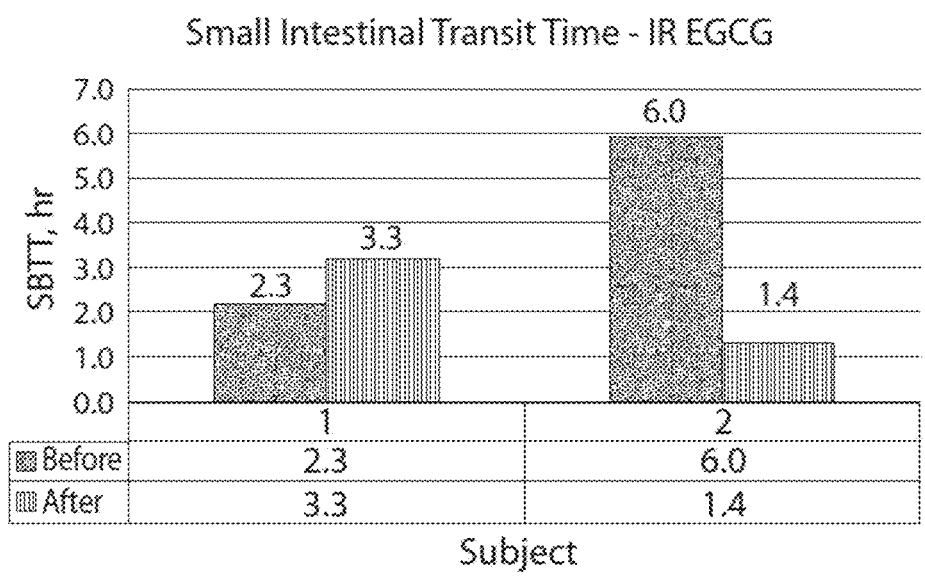
FIG. 55 depicts Small Intestinal Transit Time after administration of an IR EGCG Formulation.
Figure 56:
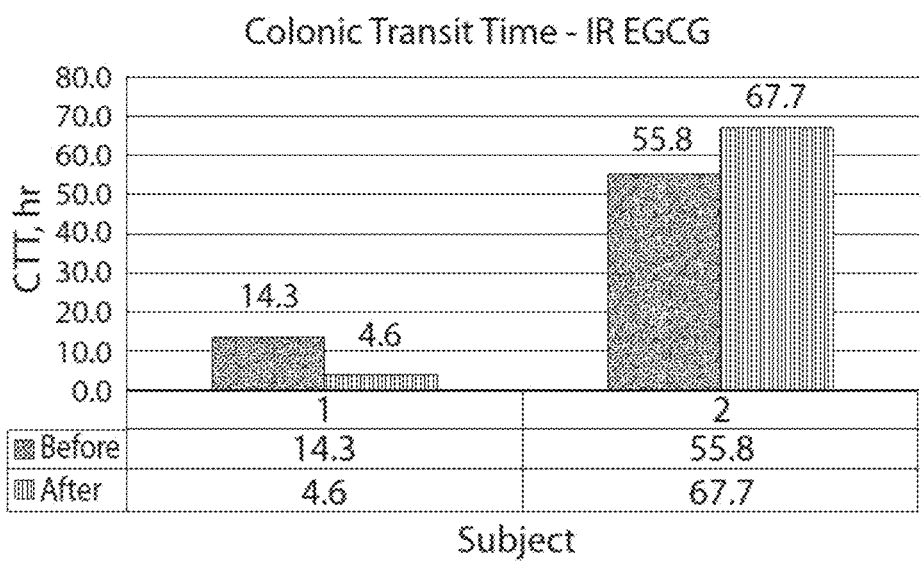
FIG. 56 depicts Colonic Transit Time after administration of an IR EGCG Formulation.
Figure 57:
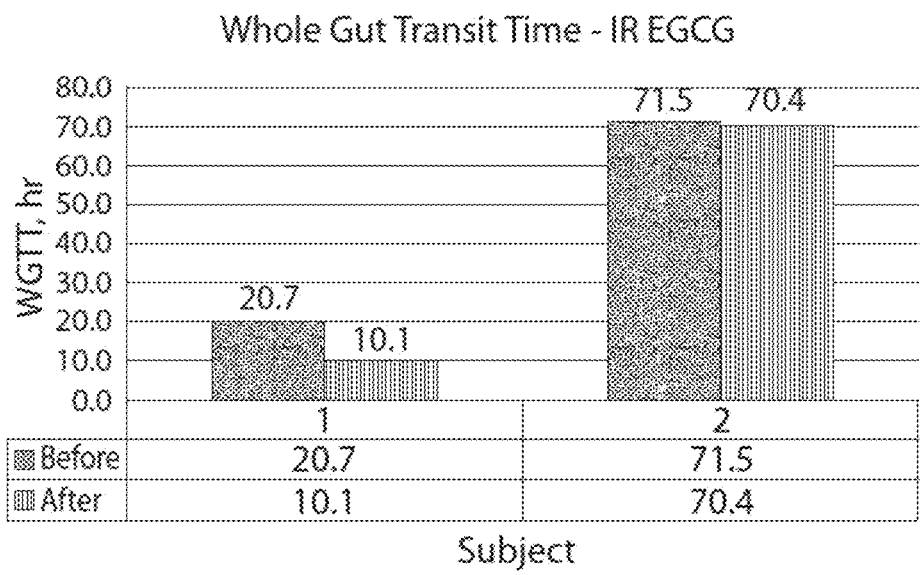
FIG. 57 depicts Whole Gut Transit Time after administration of an IR EGCG Formulation.
Figure 58:
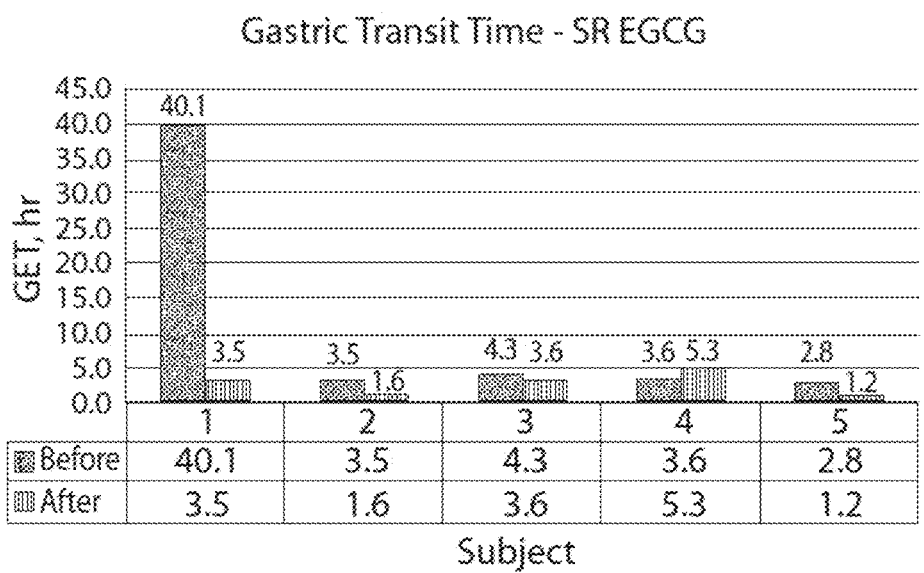
FIG. 58 depicts Gastric Transit Time after administration of an SR EGCG Formulation.
Figure 59:
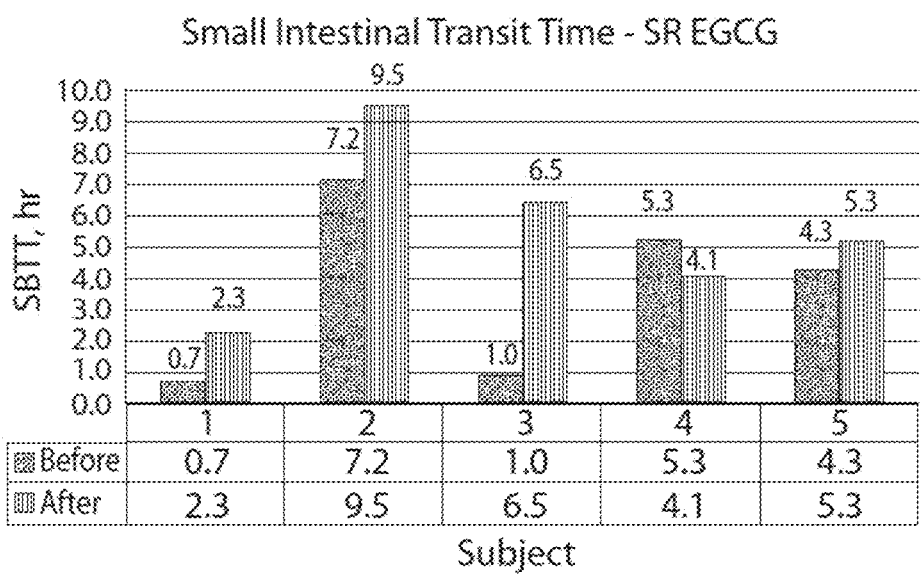
FIG. 59 depicts Small Intestinal Transit Time after administration of an SR EGCG Formulation.
Figure 60:
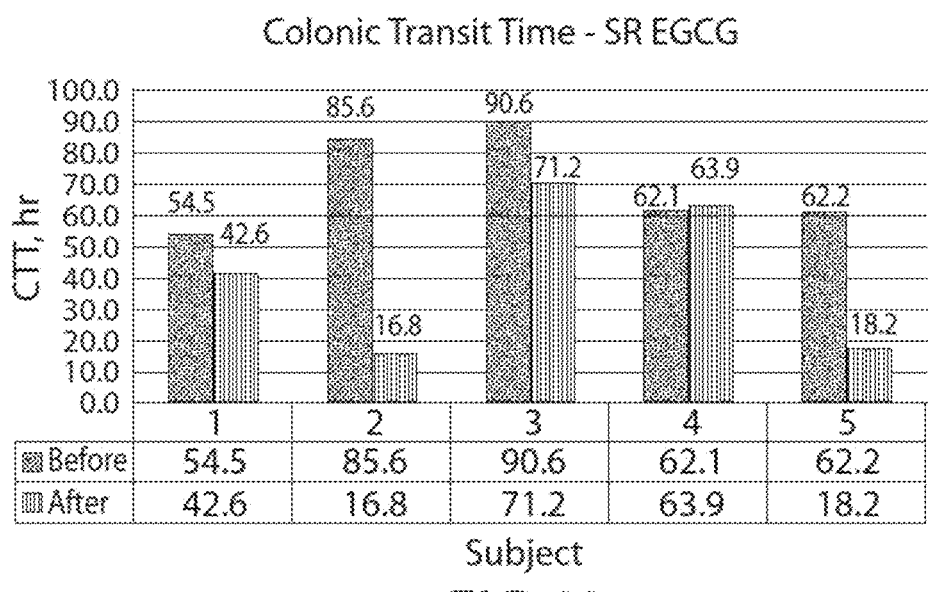
FIG. 60 depicts Colonic Transit Time after administration of an SR EGCG Formulation.
Figure 61:
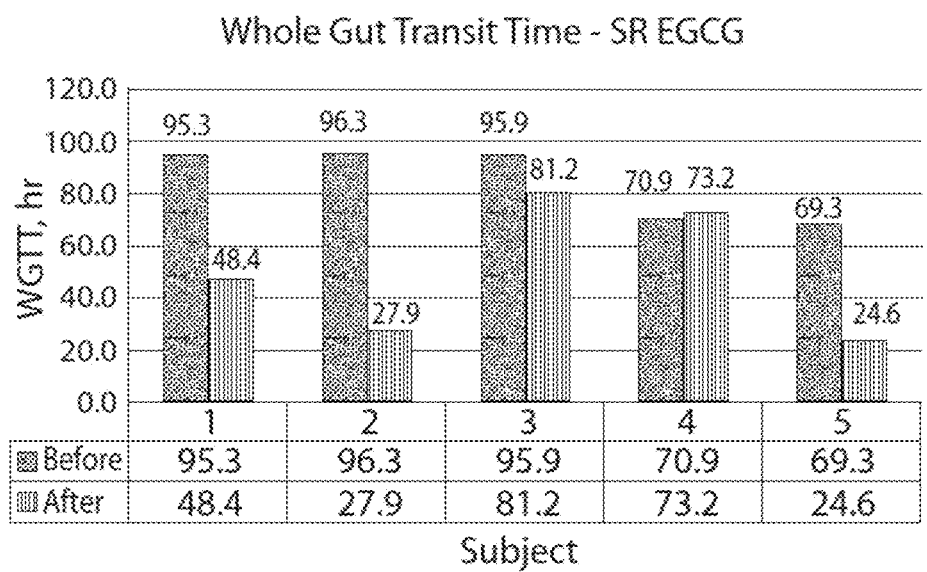
FIG. 61 depicts Whole Gut Transit Time after administration of an SR EGCG Formulation.

Determinations of gastrointestinal motility, GI pH and transit times have been reported. Mundie et. al. (Mol. Pharm. 2010, October 4; 7(5): pp 1388-1405. doi:10.1021/mp100149j) presented a summary of several studies. Among the biological variables, age, the presence of food, caloric intake, disease state, etc. make a difference in the residence time in the upper GI tract (GIT). The transit time in the lower GIT has been reported to be more significantly affected by disease state (e.g., GI disorders, Parkinson's disease, Journal of Parkinson's Disease 7 (2017) pp 471-479), fiber content of the meal (J. Nutr. Sci. Vitaminol., 1991, 37, pp 493-508), and the like.
Gastrointestinal motility, pH, and transit times were determined by Medtronic SmartPill™
Human subjects swallowed 300 mg EGCG per day in the form of an immediate release capsule (150 mg BID) or a sustained release formulation (100 mg TID), as described in Example 13, for 2 weeks and then double the dose for 16 weeks.
Gut Transit Time was determined before initiation of dosing (one to two baseline samples) and after completion of total 14 weeks of dosing.
For immediate release formulation (See Example 13, Immediate Release Formulation):
1. The therapy decreased mean Gastric Emptying Time (GET) by 75%. The biggest impact was in subject with abnormally long baseline GET of 9.7 h—decreased to 1.3 h. Individual subject results are shown in FIG. 54.
2. The therapy decreased Small Bowl Transit Time (SBTT) from a mean of 4.1 h to 2.3 h. The shorter transit time may have deleterious effect on digestion and absorption of nutrients. Individual subject results are shown in FIG. 55.
3. The therapy had no effect on Colonic Transit Time (CTT)—no significant change from mean baseline value of 35.0 h to end of therapy value of 36.2 h. Individual subject results are shown in FIG. 56.
4. Overall, whole gut transit time (WGTT) was decreased slightly from mean 46.1 h to 40.2 h. Individual subject results are shown in FIG. 57.
For the sustained release formulation (see Example 1):
1. The therapy decreased mean GET by 72%. By far, the biggest impact was in a subject with an abnormally long baseline GET of 40.1 h, which decreased to 3.5 h. Individual subject results are shown in FIG. 58.
2. The therapy increased SBTT in 4 out of 5 subjects, potentially improving digestion and absorption of nutrients. The mean SBTT from 5 subjects was improved from 3.7 h to the normal 5.5 h. The largest change was in subjects with abnormally low SBTT (0.7 h and 1.0 h). The SBTT was improved in those subjects to 2.3 h and 6.5 h, respectively. Individual subject results are shown in FIG. 59.
3. The therapy decreased CTT from mean baseline value of 71.0 h to 42.5 h. Individual subject results are shown in FIG. 60.
4. Overall, WGTT was decreased from mean 85.5 h to 51.0 h. Individual subject results are shown in FIG. 61.

Example 24

The data of FIGS. 4, 7, 8, 9A, 9B, 10-51, and 62 were obtained using the following procedure.
A mixture of 50 mM sodium phosphate buffer, adjusted to pH 6.8 with dilute hydrochloric acid and/or sodium hydroxide, was prepared with methanol [1:1 v/v] and was mixed or sonicated until homogenous. The mixture was labeled as a blank solution. The blank solution was stored at 4-8° C.
An aliquot of the blank solution was transferred to a clean 1 cm path length quartz cuvette and the UV-VIS spectrophotometer was obtained ("blanked") at 297 nm using the blank sample.
10 mg of EGCG standard was weighed out and transferred to a 100 mL volumetric flask. The flask was filled to volume using the blank solution and was then mixed or sonicated until the EGCG was fully dissolved. This solution was labeled as stock and stored at 4-8° C.
An aliquot of the stock solution was transferred to a clean 1 cm path length quartz cuvette. The absorbance of the stock solution was measured at 297 nm.
A USP Dissolution Apparatus 2 with paddles was assembled (USP Apparatus 2 configuration). Each vessel was filled with 600 mL dionized water containing 50 mM sodium phosphate buffer, adjusted to pH 6.8 with dilute hydrochloric acid and/or sodium hydroxide. The temperature was set to 37° C.±0.5° C. and the vessels were allowed to come to temperature. Upon reaching temperature, one sustained-release solid dosage form that is secured in a sinker was dropped into each vessel (N=6), the paddles were set to 50 rpm (rotation per minute) and the vessels were covered.

3 mL aliquots were sampled at the specified time intervals, e.g., 4, 40, and 75 hours. 3 mL of methanol was added to each sample. The samples were homogenized and filtered through a 0.45 μm membrane into a clean 1 cm path length quartz cuvette. The absorbance of each sample was determined at 297 nm and the percentage of EGCG released was calculated according to the equation: % EGCG released= [12*mg EGCG standard*EGCG standard potency*$Abs_{sample}$]/$Abs_{standard}$.

Following sampling of the terminal time point, the dosage form remains were transferred from each vessel to a mortar and were ground using a pestle. The ground material was transferred to a 100 mL volumetric flask and the mortar and pestle were rinsed with MeOH. The volumetric flask and brought to volume with MeOH and sonicated for 5 min. The sample was diluted with an equal volume of 50 mM sodium phosphate buffer, adjusted to pH 6.8 with dilute hydrochloric acid and/or sodium hydroxide, and the solution was filtered through a 0.45 μm membrane into a clean 1 cm path length quartz cuvette. The absorbance of each sample was measured at 297 nm and the percentage of EGCG remaining in the tablet was calculated using the following equation: % EGCG remaining=2*[mg EGCG standard*EGCG standard potency*$Abs_{sample}$]/$Abs_{standard}$. The normalized % EGCG released at each time point was calculated using the following equation: Normalized % EGCG released$_{(t)}$=(100−% EGCG remaining)/% EGCG released$_{(terminal\ time\ point)}$*% EGCG release$_{(t)}$.

Those of ordinary skill in the art will recognize, or be able to ascertain using no more than routine experimentation, many equivalents to the specific embodiments of the invention described herein.

The invention claimed is:

1. A sustained-release solid dosage form of epigallocatechin gallate (EGCG), comprising a plurality of solid particulates selected from the group consisting of mini-tablets, beads, granules, and pellets, or being in a form of a single solid dosage form, and wherein the solid particulates or the single solid dosage form each comprise(s):
   a core comprising EGCG and a
   release rate controlling material selected from the group consisting of polyethylene oxide, poly(acrylic acid), methacrylic ester copolymer, alkylammonium methacrylate copolymer, and hydroxypropyl methyl cellulose;
   wherein the sustained-release solid dosage form releases 10-50% of the EGCG within 24 hours, 30-80% of the EGCG within 48 hours, and at least 60% of the EGCG within 72 hours of administration of said dosage form to a human subject;
   wherein the sustained-release solid dosage form comprises a total amount of EGCG in the range of about 50 mg to about 1,000 mg; and
   wherein the EGCG has a purity of at least 98%.

2. The sustained-release solid dosage form of claim 1, wherein the core comprises: (a) EGCG, (b) poly(acrylic acid), (c) colloidal silicon dioxide, and (d) magnesium stearate.

3. The sustained-release solid dosage form of claim 2, wherein the weight ratio of (a):(b):(c):(d) in the core is about 58.6:39:1.2:1.

4. The sustained-release solid dosage form of claim 1, wherein the core comprises: (a) EGCG, (b) polyethylene oxide, (c) colloidal silicon dioxide, and (d) sodium stearyl fumarate.

5. The sustained-release solid dosage form of claim 4, wherein the weight ratio of (a):(b):(c):(d) in the core is about 19.3:77.2:1.2:2.3.

6. The sustained-release solid dosage form of claim 1, wherein the core comprises: (a) EGCG, (b) poly(acrylic acid), (c) talc, and (d) magnesium stearate.

7. The sustained-release solid dosage form of claim 6, wherein the weight ratio of (a):(b):(c):(d) in the core is about 65.3:32.7:1:1.

8. The sustained-release solid dosage form of claim 1, wherein the core comprises: (a) EGCG, (b) methacrylic ester copolymer, alkylammonium methacrylate copolymer, or a combination thereof, (c) colloidal silicon dioxide, and (d) magnesium stearate.

9. The sustained-release solid dosage form of claim 8, wherein the weight ratio of (a):(b):(c):(d) in the core is about 32.7:65.3:1:1.

10. The sustained-release solid dosage form of claim 8, comprising a coating on the solid particulates, wherein the coating comprises methacrylic ester copolymer, alkylammonium methacrylate copolymer, or a combination thereof.

11. The sustained-release solid dosage form of claim 10, wherein the weight ratio of the coating to the core is about 8:100 to about 10:100.

12. The sustained-release solid dosage form of claim 1, wherein the core comprises: (a) EGCG, (b) methacrylic ester copolymer, alkylammonium methacrylate copolymer, or a combination thereof, (c) colloidal silicon dioxide, and (d) sodium stearyl fumarate.

13. The sustained-release solid dosage form of claim 12, wherein the weight ratio of (a):(b):(c):(d) in the core is about 32:64.1:1.3:2.6.

14. The sustained-release solid dosage form of claim 1, wherein the administration is oral administration.

15. The sustained-release solid dosage form of claim 1, wherein the total amount of EGCG is in the range of about 50 mg to about 200 mg.

16. The sustained-release solid dosage form of claim 1, wherein the total amount of EGCG is in the range of about 100 mg to about 300 mg.

* * * * *